US011925101B2

(12) United States Patent
Li et al.

(10) Patent No.: US 11,925,101 B2
(45) Date of Patent: Mar. 5, 2024

(54) ORGANIC SEMICONDUCTING COMPOUND AND THE ORGANIC PHOTOELECTRIC COMPONENTS USING THE SAME

(71) Applicant: RAYNERGY TEK INCORPORATION, Hsinchu (TW)

(72) Inventors: Wei-Long Li, Hsinchu (TW); Yu-Tang Hsiao, Hsinchu (TW); Chia-Hua Tsai, Hsinchu (TW); Chuang-Yi Liao, Hsinchu (TW)

(73) Assignee: RAYNERGY TEK INCORPORATION, Hsinchu (TW)

( * ) Notice: Subject to any disclaimer, the term of this patent is extended or adjusted under 35 U.S.C. 154(b) by 0 days.

(21) Appl. No.: 17/930,868

(22) Filed: Sep. 9, 2022

(65) Prior Publication Data
US 2023/0126747 A1    Apr. 27, 2023

Related U.S. Application Data

(60) Provisional application No. 63/244,362, filed on Sep. 15, 2021.

(51) Int. Cl.
*H10K 30/00* (2023.01)
*C08G 61/12* (2006.01)
(Continued)

(52) U.S. Cl.
CPC ......... *H10K 85/113* (2023.02); *C08G 61/126* (2013.01); *H10K 30/451* (2023.02);
(Continued)

(58) Field of Classification Search
CPC .... H10K 85/113; H10K 30/451; H10K 30/82; H10K 85/151; H10K 85/40; H10K 85/657; H10K 85/6576; H10K 30/30; H10K 85/215; C08G 61/126; C08G 2261/124; C08G 2261/1412; C08G 2261/1424;
(Continued)

(56) References Cited

FOREIGN PATENT DOCUMENTS

CN    109790176 A    5/2019
CN    112920204 A    6/2021
(Continued)

OTHER PUBLICATIONS

Jinfeng Han "Low-Bandgap Polymers for High-Performance Photodiodes with Maximal EQE near 1200 nm and Broad Spectral Response from 300 to 1700 nm" Adv. Optical Mater. 2018, 6, 1800038 (Year: 2018).*

(Continued)

*Primary Examiner* — Michael Y Sun
(74) *Attorney, Agent, or Firm* — WPAT, P.C

(57) ABSTRACT

An organic semiconducting compound and an organic photoelectric component containing the same are provided. The organic semiconducting compound has a novel chemical structure to make the organic semiconducting compound have good response to the infrared light. The organic semiconducting compound can be applied to the organic photoelectric components such as organic photodetector (OPD), organic photovoltaic (OPV) cell, and organic field-effect transistor (OFET). Thus, the organic photoelectric components have better light absorption range and photoelectric response while in use.

12 Claims, 6 Drawing Sheets

(51) Int. Cl.
*H10K 30/82* (2023.01)
*H10K 85/10* (2023.01)
*H10K 85/40* (2023.01)

(52) U.S. Cl.
CPC ........... *H10K 30/82* (2023.02); *H10K 85/151* (2023.02); *H10K 85/40* (2023.02); *C08G 2261/124* (2013.01); *C08G 2261/1412* (2013.01); *C08G 2261/1424* (2013.01); *C08G 2261/146* (2013.01); *C08G 2261/148* (2013.01); *C08G 2261/149* (2013.01); *C08G 2261/18* (2013.01); *C08G 2261/228* (2013.01); *C08G 2261/3223* (2013.01); *C08G 2261/3241* (2013.01); *C08G 2261/3246* (2013.01); *C08G 2261/3247* (2013.01); *C08G 2261/91* (2013.01)

(58) Field of Classification Search
CPC ........ C08G 2261/146; C08G 2261/148; C08G 2261/149; C08G 2261/18; C08G 2261/228; C08G 2261/3223; C08G 2261/3241; C08G 2261/3246; C08G 2261/3247; C08G 2261/91; C08G 2261/1432; C08G 2261/16; C08G 2261/164; C08G 2261/1642; C08G 2261/1646; C08G 2261/224; C08G 2261/226; C08G 2261/3243; C08G 2261/334; C08G 2261/414; C07D 519/00; C08L 65/00; C09D 165/00; C09K 11/06; Y02E 10/549
See application file for complete search history.

(56) References Cited

FOREIGN PATENT DOCUMENTS

| | | |
|---|---|---|
| JP | 2013-199590 | 10/2013 |
| JP | 2016-524010 | 8/2016 |
| JP | 2018-521151 | 8/2018 |
| JP | 2019-502001 | 1/2019 |
| JP | 2019-536744 | 12/2019 |
| JP | 2023-24300 | 2/2023 |
| JP | 2023-024349 | 2/2023 |
| JP | 2023-033222 | 3/2023 |
| TW | 201111411 A | 4/2011 |
| TW | 201509983 A | 3/2015 |
| TW | 201736430 A | 10/2017 |
| TW | 201808964 A | 3/2018 |
| WO | WO201125454 | 3/2011 |
| WO | WO2017157782 | 9/2017 |

OTHER PUBLICATIONS

Qiang Peng "Donor-d-Acceptor Conjugated Copolymers for Photovoltaic Applications: Tuning the Open-Circuit Voltage by Adjusting the Donor/Acceptor Ratio" J. Phys. Chem. B 2008, 112, 2801-2808 (Year: 2008).*
Yunpeng Qin "Highly Efficient Fullerene-Free Polymer Solar Cells Fabricated with Polythiophene Derivative" Adv. Mater. 2016, 28, 9416-9422 (Year: 2016).*
Richard Hildner "π-Conjugated Donor Polymers: Structure Formation and Morphology in Solution, Bulk and Photovoltaic Blends" Adv. Energy Mater. 2017, 7, 1700314 (Year: 2017).*
Frederick Verstraeten, et al., Efficient and Readily Tuneable Near-Infrared Photodetection Up to 1500 NM Enabled by Thiadiazoloquinoxaline-Based Push-Pull Type Conjugated Polymers, J. Mater. Chem. C, 2020, 8, 10098.
Yoonkyoo Lee, et al., Fine-Tuning of Molecular Energy Level of Alternating Copolymers on the Basis of [1,2,5] Thiadiazolo [3,4-g] Quinoxaline Derivatives for Polymer Photovoltaics, J. Phys. Chem. C, 2012, 116, 8379-8386.
Jinfeng Han et al., "1. Low-Bandgap Terpolymers for High-Gain Photodiodes with High Detectivity and Responsivity from 300 nm to 1600 nm", 2018, Wiley-VCH Verlag Gmbh & Co. KGaA, Weinheim.
Japan Patent Office Official action, dated Oct. 24, 2023.
Taiwan Intellectual Property Office official action, dated Nov. 16, 2023.

* cited by examiner

ORGANIC SEMICONDUCTING COMPOUND AND THE ORGANIC PHOTOELECTRIC COMPONENTS USING THE SAME

BACKGROUND OF THE INVENTION

Field of the Invention

The present invention relates to a compound and a photoelectric component containing the same, especially to an organic semiconducting compound with good physical and chemical properties and an organic photoelectric component containing the same. The organic semiconducting compound is able to be processed by environmentally friendly organic solvents, more convenient in production, and having less impact on the environment while the organic photoelectric component containing the same has excellent response in the infrared region and low dark current density.

Description of Related Art

In recent years, demands for organic semiconducting compounds are increasing in order to produce more general electronics with lower cost. Compared with conventional semiconducting materials, organic semiconducting compounds have wider absorption range, larger absorption coefficient, and adjustable structure. Their absorption range, energy gap and solubility can also be adjusted according to user's requirements. Moreover, organic materials have advantages of low cost, flexibility, lower toxicity, and large-area fabrication while being applied to production of the components. Thus, the organic optoelectronic materials have good competitiveness on the respective fields and wide applications including organic field-effect transistor (OFET), organic light-emitting diode (OLED), organic photodetector (OPD), organic photovoltaic (OPV) cells, transducers, respective components and assemblies of memory components and logic circuit, etc. In the respective components or assemblies of the above applications, the organic semiconducting materials are usually in the form of a thin-film with a thickness ranging from 50 nm to 1 µm.

Organic photodetectors are one of the new and developing fields of the organic optoelectronics recently. They can be used to detect various light sources in the environment and applied to different fields such as medical care, health management, intelligent drive, drones, and digital home. The respective fields have different requirements for materials. The devices produced by organic materials have good flexibility. Due to fast development of modern materials science, OPD not only can be produced into a thin-film layer but also used for absorption of specific wavelengths. The products available on the market now have different absorption wavelength ranges due to different light sources. The organic materials have adjustable light absorption range so that they can be designed to absorb at specific wavelengths required for reducing interference. The high extinction coefficient of the organic materials can improve the detection efficiency effectively. The recent development of the OPD is shifted from ultraviolet and visible light gradually to near-infrared (NIR) light.

Materials for active layers in the OPD play an important role since they have direct impact on the component performance. The materials are divided into donors and acceptors. The most common donor materials include organic polymers, oligomers, and low molecule unit while development of D-A type conjugate polymers is the mainstream nowadays. The energy levels and energy gaps of the polymer can be adjusted by push-pull electronic effects caused by interaction between electron-rich units and electron-deficient units of the polymer. The acceptor materials used in combination with the donor materials include fullerene derivatives with high conductivity and absorption range between 400-600 nm, graphene, metal oxides, quantum dots, non-fullerene organic compounds just emerged in recent years, etc.

In order to avoid strong visible light interference in the fields of intelligent drive and drones, organic photodetectors which absorb near-infrared light have been developed. For better transmittance and long distance detection, the wavelength should be over 1000 nm. The photoelectric components used need to have higher responsivity and lower dark current density ($J_d$) to meet more requirements for the fields. During manufacturing of the materials, environmentally friendly solvents should be used as much as possible for environmental compliance in different countries and good processability. The organic semiconducting materials with potentials available now such as donor acceptor conjugated polymers or small molecules only have good performance in the absorption range below 1000 nm while components made from materials with the absorption range beyond 1000 nm have poor performance. Now certain competitive organic semiconducting polymer such as the one revealed by J. Mater. Chem. C, 2020, 8, 10098-10103 can be applied to the absorption range beyond 1000 nm. But there is a serious gap caused by lower optoelectronic response at the wavelength of 700 nm. Thereby it is difficult to achieve good response in the whole wavelength range. Moreover, P3HT polymer molecules commonly used in the field are easy to stack and thus additives are used to avoid the stacking and reduce dark current density of the organic photoelectric components prepared. Yet the use of the additives leads to reduced stability of the components and this further affects the lifetime of the organic photoelectric components. Furthermore, solvents used during wet processing of the organic semiconducting materials are mainly organic solvents containing halogens which have negative effects on the environment. Thus, there is room for improvement and there is a need to provide a novel organic semiconducting compound with excellent infrared light response, better electrical performance, having low stacking effect, and able to be processed without using organic solvents containing halogens.

SUMMARY OF THE INVENTION

Therefore, it is a primary object of the present invention to provide a new organic semiconducting compound, especially to a p-type organic semiconducting compound which not only overcomes the shortcomings of the conventional organic semiconducting compounds, but also provides at least one of the good properties mentioned above. Moreover, the organic semiconducting compound can be synthesized by methods suitable for mass production, having whole wavelength light response in the wavelength range larger than 1000 nm, providing good component efficiency, without easy stacking of the molecules during production processes, and having good processability and solubility in environmentally friendly solvents which are beneficial to mass production by solution processing.

It is another object of the present invention to provide a new organic photoelectric component containing an organic semiconducting compound, which has light response in wide wavelengths ranging from ultraviolet light, visible light, to near-infrared (NIR), lower dark current density, and excellent detectivity.

In order to achieve the above object, an organic semiconducting compound according to the present invention is represented by the following chemical formula:

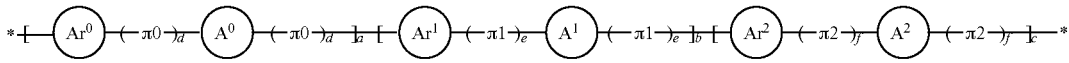

wherein $A^0$ is an electron withdrawing group; $A^1$ and $A^2$ are electron withdrawing groups which are different from $A^0$ while $A^1$ and $A^2$ are the same or different from each other; $Ar^0$, $Ar^1$, $Ar^2$, $\pi 0$, $\pi 1$, $\pi 2$ are electron donating groups independent from one another, the same or different from one another; d, e, and f are integers independent from one another and selected from 0 to 5; a, b, and c are real numbers, wherein a+b+c=1, $0<a\leq 1$, $0<b\leq 1$ and $0<c\leq 1$.

In order to achieve the above object, an organic photoelectric component according to the present invention includes a substrate, an electrode module disposed on the substrate, and an active layer. The electrode module consists of a first electrode and a second electrode while the active layer is arranged between the first electrode and the second electrode. The active layer is made of materials including at least one organic semiconducting compound according to the present invention. At least one of the first electrode and the second electrode is transparent or semi-transparent.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Figure 1A:
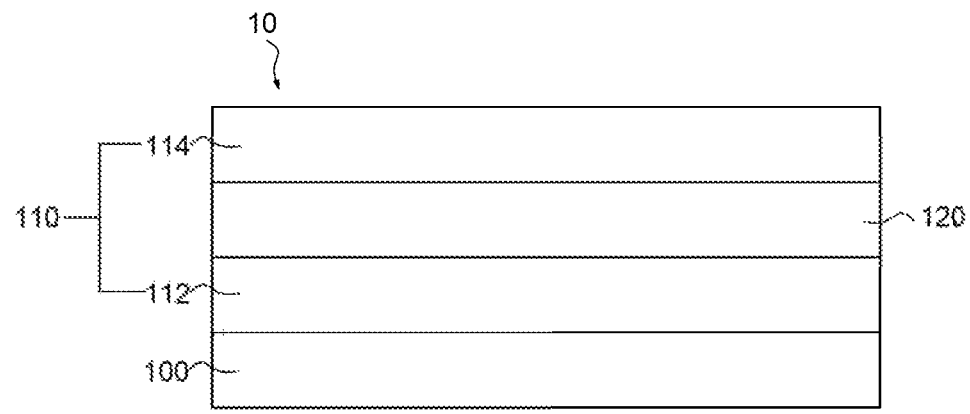
FIG. 1A-1F are schematic drawings showing structure of an embodiment of an organic photoelectric component according to the present invention.

Organic semiconducting compounds of the present invention are easy to synthesis and have good processability and solubility in solvents during manufacturing process. These properties are beneficial to solution processing which enables mass production of the organic semiconducting compounds.

The preparation of the organic semiconducting compounds of the present invention which is based on the methods learned by people skilled in the art and mentioned in prior arts is going to be described in the following embodiments.

An embodiment of an organic photoelectric component according to the present invention is shown by the following chemical formula:

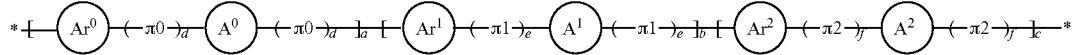

wherein $A^0$ is an electron withdrawing group; $A^1$ and $A^2$ are electron withdrawing groups which are different from $A^0$ while $A^1$ and $A^2$ are the same or different from each other; $Ar^0$, $Ar^1$, $Ar^2$, $\pi 0$, $\pi 1$, and $\pi 2$ are electron donating groups independent from one another, the same or different from one another; d, e, and f are integers independent from one another and selected from 0 to 5; and a, b, and c are real numbers, wherein a+b+c=1, $0<a\leq 1<b\leq 1$ and $0<c\leq 1$.

In an organic semiconducting compound of the present invention, $Ar^0$, $Ar^1$, $Ar^2$, $\pi 0$, $\pi 1$, and $\pi 2$ are selected from the following groups:

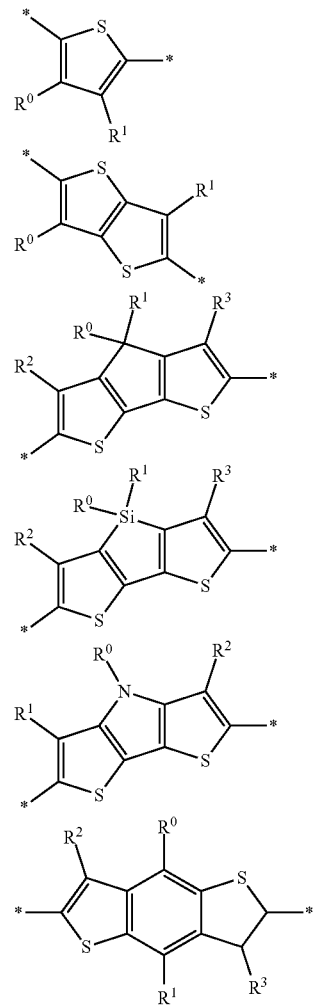

-continued

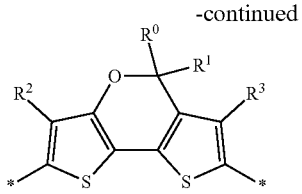

wherein R⁰-R³ are selected from the group consisting of hydrogen atom, halogens, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, C3-C30 keto-substituted alkyl, unsubstituted aromatic group, unsubstituted heterocyclic group, unsubstituted fused ring group, unsubstituted fused heterocyclic group, aromatic group substituted with at least one R$^a$, heterocyclic group substituted with at least one R$^a$, fused ring group substituted with at least one R$^a$, and fused heterocyclic group substituted with at least one R$^a$; and wherein R$^a$ is selected from the group consisting of hydrogen atom, halogen, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl.

In an organic semiconducting compound of the present invention, A⁰ is selected from the following groups:

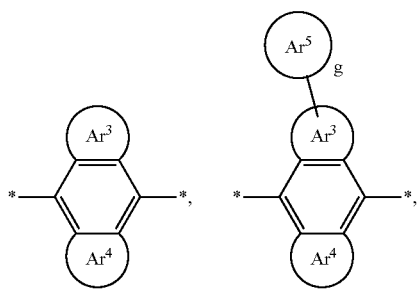

wherein Ar³ and Ar⁴ are selected from the group consisting of unsubstituted aromatic group, unsubstituted heterocyclic group, unsubstituted fused ring group, unsubstituted fused heterocyclic group, aromatic group substituted with at least one R$^a$, heterocyclic group substituted with at least one R$^a$, fused ring group substituted with at least one R$^a$, and fused heterocyclic group substituted with at least one R$^a$; wherein Ar⁵ is selected from the group consisting of hydrogen atom, halogen, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, C3-C30 keto-substituted alkyl, unsubstituted aromatic group, unsubstituted heterocyclic group, unsubstituted fused ring group, unsubstituted fused heterocyclic group, aromatic group substituted with at least one R$^b$, heterocyclic group substituted with at least one R$^b$, fused ring group substituted with at least one R$^b$, and fused heterocyclic group substituted with at least one R$^b$; wherein R$^a$ and R$^b$ are selected from the group consisting of hydrogen atom, halogen, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl; wherein g is a positive integer selected from 1 to 8.

In an organic semiconducting compound of the present invention, A¹ is selected from the following groups:

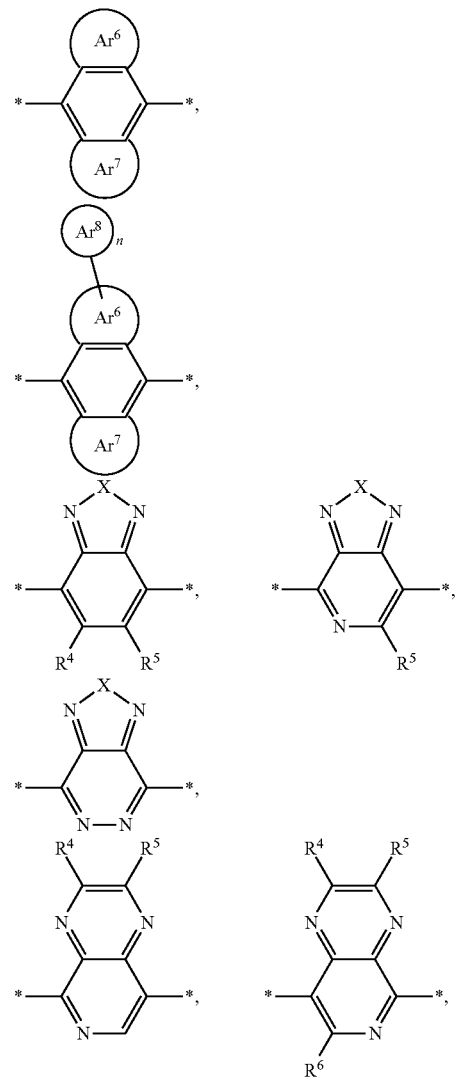

wherein R⁴-R⁶ are selected from the group consisting of the following groups: hydrogen atom, halogen, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, C3-C30 keto-substituted alkyl, unsubstituted aromatic group, unsubstituted heterocyclic group, unsubstituted fused ring group, unsubstituted fused heterocyclic group, aromatic group substituted with at least one R$^a$, heterocyclic group substituted with at least one R$^a$, fused ring group substituted with at least one R$^a$, and fused heterocyclic group substituted with at least one R$^a$; wherein X is selected from the group consisting of O, S, or Se; wherein Ar⁶ and Ar⁷ are selected from the group consisting of unsubstituted aromatic group, unsubstituted heterocyclic group, unsubstituted fused ring group, unsubstituted fused heterocyclic group, aromatic group substituted with at least one $R^a$, heterocyclic group substituted with at least one $R^a$, fused ring group substituted with at least one $R^a$, and fused heterocyclic group substituted with at least one $R^a$; wherein $Ar^8$ is selected from the group consisting of hydrogen atom, halogen, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, C3-C30 keto-substituted alkyl, unsubstituted aromatic group, unsubstituted heterocyclic group, unsubstituted fused ring group, unsubstituted fused heterocyclic group, aromatic group substituted with at least one $R^b$, heterocyclic group substituted with at least one $R^b$, fused ring group substituted with at least one $R^b$, and fused heterocyclic group substituted with at least one $R^b$; wherein $R^a$ and $R^b$ are selected from the group consisting of hydrogen atom, halogen, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl; wherein h is a positive integer selected from 1 to 8.

In an organic semiconducting compound of the present invention, $A^2$ is selected from the following groups:

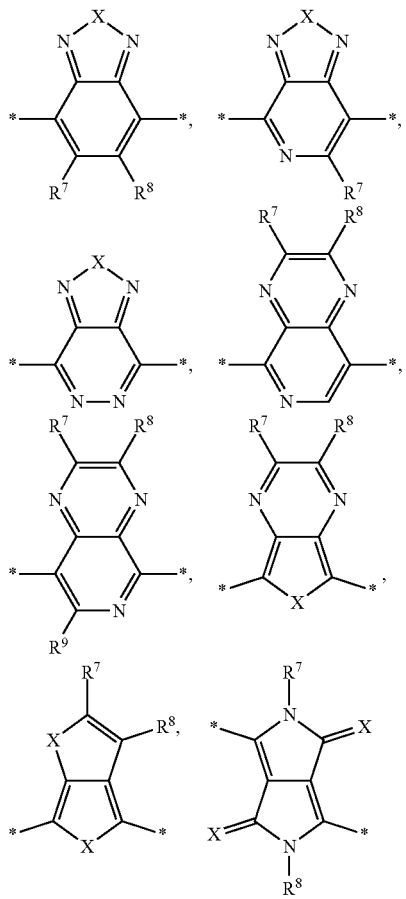

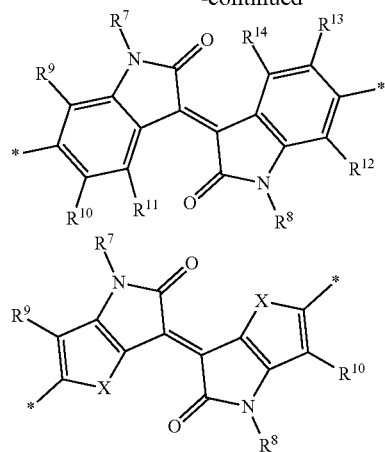

wherein $R^7$-$R^{14}$ are selected from the group consisting of hydrogen atom, halogen, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, C3-C30 keto-substituted alkyl, unsubstituted aromatic group, unsubstituted heterocyclic group, unsubstituted fused ring group, unsubstituted fused heterocyclic group, aromatic group substituted with at least one $R^b$, heterocyclic group substituted with at least one $R^b$, fused ring group substituted with at least one $R^b$, and fused heterocyclic group substituted with at least one $R^b$; wherein $R^b$ is selected from the group consisting of hydrogen atom, halogen, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituent alkyl, C1-C30 nitro-substituent alkyl, C1-C30 hydroxy-substituent alkyl, and C3-C30 keto-substituent alkyl; and wherein X is selected from the group consisting of O, S, and Se.

How an organic semiconducting compound according to the present invention is prepared is described in the following embodiments.

Preparation of Organic Compound C10:

chemical reaction 1

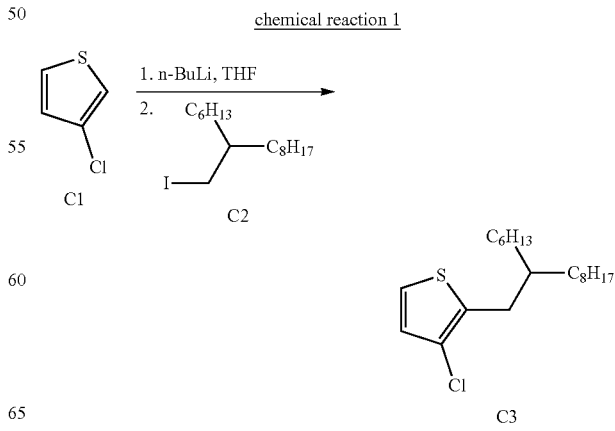

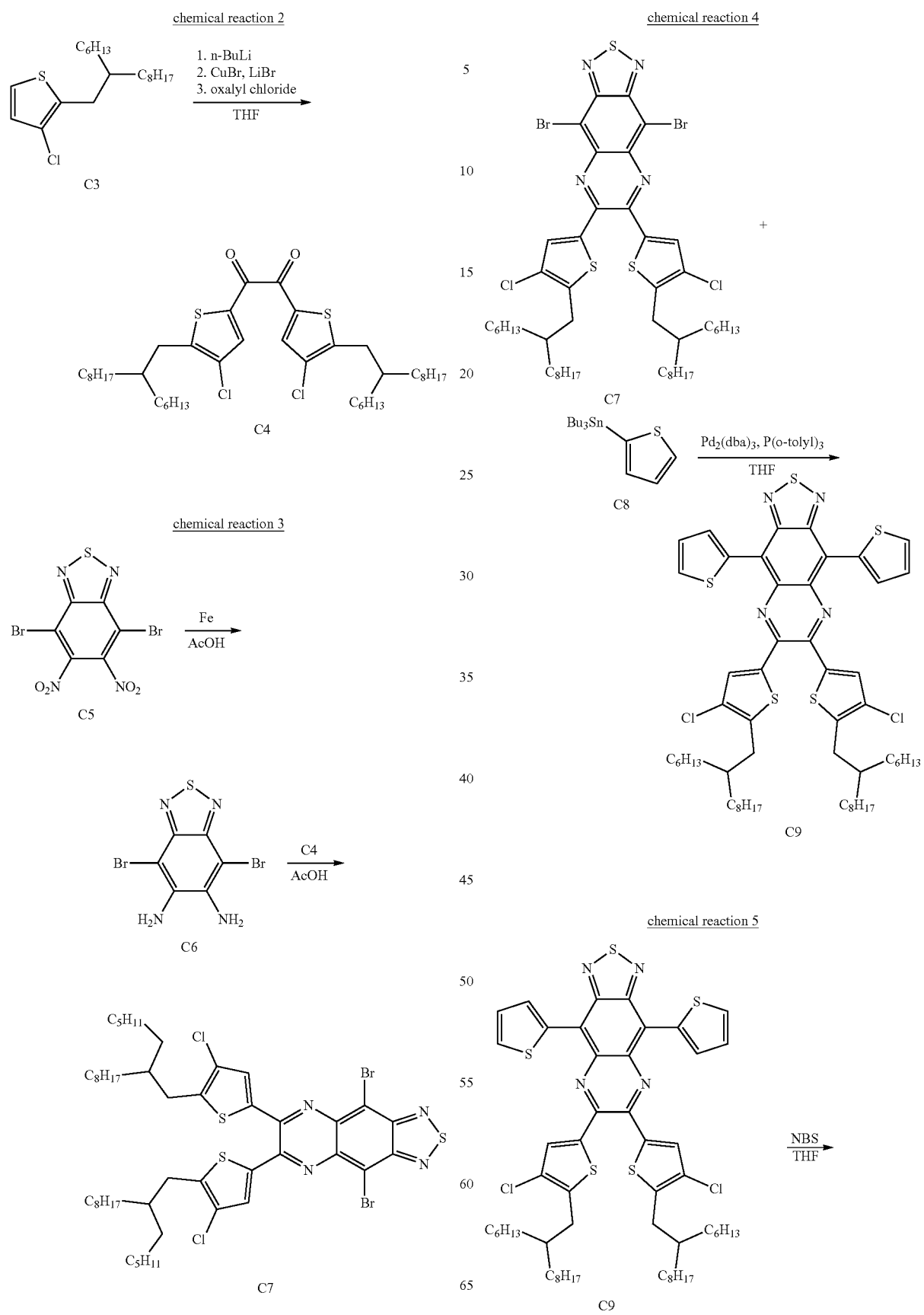

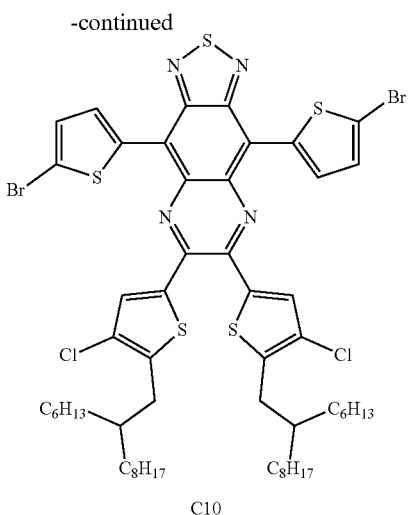

C10

In the beginning, refer to chemical reaction 1. Put 10 g (86.3 mmol) compound C1 into a 500 mL four neck reaction flask and add 50 mL anhydrous tetrahydrofuran (THF) into the flask. Then stir mixture for dissolution and cool the obtained solution down to 15 degrees Celsius (° C.). Slowly drop 34.5 mL n-butyllithium (n-BuLi) into the solution until the color becomes light orange. Allow the solution to reach room temperature and stir the solution for 1 hour. At 15° C., drop 19.81 g (5.62 mmol) compound C2 to the solution until the solution becomes light yellow and clear. Reactants are allowed to reach the room temperature and stir for 20 hours and then add 5 mL water to stop reaction. After rotary evaporation for removal of organic solvents, add 100 mL heptane for dissolution and extract with 20 mL of water three times (3×20 mL). Collect the organic layer, remove water with magnesium sulfate ($MgSO_4$), and remove the organic solvents with rotary evaporation to get a crude product. Use vacuum evaporation for removal of starting materials and impurities (0.25 torr, 80-100° C.). The residue left in the flask is then purified by silica gel column with heptane as eluant. Then collect the main portion of the fraction, remove organic solvents by rotary evaporation, and dry in vacuum at 50° C. to get 9.3 g compound C3 which is oily product in light yellow color (yield rate=51%). $^1$H NMR spectrum (500 MHz, $CDCl_3$) of the compound C3: δ 7.09 (d, J=6.5 Hz, 1H), 6.85 (d, J=6.5 Hz, 1H), 2.72 (d, J=7.0 Hz, 2H), 1.68 (m, 1H), 1.27 (m, 24H), 0.88 (m, 6H).

Refer to chemical reaction 2, put 20 g (58.31 mmol) compound C3 into a 250 mL three neck reaction flask and add 160 mL tetrahydrofuran (THF) into the flask. Then place the flask in an ice bath (<10° C.) and stir a solution in the flask for one hour after adding 23.32 mL (58.31 mmol) n-butyllithium (n-BuLi) into the flask. Put 8.36 g (58.31 mmol) copper(I) bromide (CuBr) and 5.06 g (58.31 mmol) lithium bromide (LiBr) into another 500 mL three neck reaction flask, put the flask into an ice bath, and add 160 mL tetrahydrofuran (THF) into the flask. Next the reactants in the 250 mL three neck reaction flask is transferred into the 500 mL three neck reaction flask in the ice bath and stir a solution obtained for one hour. Then add 3.36 g (2.27 mL, 26.5 mmol) oxalyl chloride into the flask in the ice bath, allow the solution to reach the room temperature and stir the solution for 18 hours. Add 100 mL water to stop reaction, add 200 mL heptane, and extract with 100 mL of water three times (3×100 mL). Collect the organic layer and remove water with magnesium sulfate ($MgSO_4$). After removal of the solvents, silica gel column is used for purification and a mixture of heptane and dichloromethane ($CHCl_2$) in a ratio of 4:1 is used as eluent. Lastly collect the main portion of the fraction and get 12 g yellow orange oily liquid compound C4 after concentration and drying (yield is 61.2%). $^1$H NMR spectrum (500 MHz, $CDCl_3$) of the compound C4: δ 7.88 (s, 2H), 2.80 (d, J=7.0 Hz, 4H), 1.76 (m, 2H), 1.29 (m, 48H), 0.88 (m, 12H).

Refer to chemical reaction 3, put 2 g (5.21 mmol) compound C5 into a 100 mL three neck reaction flask and add 60 mL glacial acetic acid into the flask. With a magnetic stirrer providing vigorous stirring, add 5.83 g (104.4 mmol) iron powder into a solution in the flask and heat mixture up to 80° C. to react for 16 hours. Cool the reacted mixture to room temperature, pour the reacted mixture into 200 mL water with ice, and collect solid after filtration. Wash the solid with distilled water and dry the solid under vacuum. Then dissolve crude product obtained in 200 mL tetrahydrofuran (THF) and filter the solution for removal of the iron powder. Remove organic solutions by rotary evaporation and dry in a vacuum to get 1.35 g compound C6 with yield of 80%. Next put compound C6, 2.7 g (3.65 mmol) C4, and 40 mL acetic acid ($CH_3COOH$) into another reaction flask. With a vigorously stirring magnetic stirrer, heat mixture up to 120° C., react for 16 hours, and cool down to room temperature. Pour reacted mixture into 50 mL water with ice, extract with dichloromethane (DCM), and wash the organic layer with 50 mL distilled water three times (3×50 mL). Remove water in the organic layer with magnesium sulfate ($MgSO_4$) and remove solvent by rotary evaporation to get a crude product. Next the crude product is purified by silica gel column and a mixture of heptane and DCM in a ratio of 4:1 is used as eluent. Lastly collect the main portion of the fractions and get 2.4 g dark red solid, compound C7 with yield of 61.6% after vacuum drying. $^1$H NMR spectrum (500 MHz, $CDCl_3$) of the compound C7: δ 7.45 (s, 2H), 2.83 (d, J=7.0 Hz, 4H), 1.83 (m, 2H), 1.30 (m, 48H), 0.89 (m, 12H).

Refer to chemical reaction 4, put 2 g (1.942 mmol) compound C7 and 1.60 g (4.287 mmol) compound C8 into a 100 mL three neck reaction flask and add 40 mL tetrahydrofuran (THF) into the flask. Introduce argon to purge out oxygen for 15 mins. Add 0.071 g (0.078 mmol) Tris(dibenzylideneacetone)dipalladium ($Pd_2(dba)_3$) and 0.095 g (0.311 mmol) tri(o-tolyl)phosphine into the flask, heat up to 66° C., and stir reactants for 2 hours. After cooled down, filter the reactants with celite, and wash the reactants with heptane. Remove organic solvents by rotary evaporation, use silica gel column for purification, and use a mixture of DCM and heptane in a radio of 1:4 as eluent. Then collect the main portion of the fractions to get 1.81 g brown viscous liquid, compound C9 with yield of 90.1% after concentration. $^1$H NMR spectrum (600 MHz, $CDCl_3$) of the compound C9: δ 8.88 (d, J=4.8 Hz, 2H), 7.71 (d, J=4.8 Hz, 2H), 7.43 (s, 2H), 7.34 (t, J=6.0 Hz, 2H), 2.85 (d, J=8.4 Hz, 4H), 1.83 (m, 2H), 1.30 (m, 48H), 0.88 (m, 12H).

Refer to chemical reaction 5, put 1.81 g (1.75 mmol) compound C9 into a 100 mL three neck reaction flask and add 107 mL tetrahydrofuran (THF) into the flask under nitrogen atmosphere. Add 0.716 g (4.023 mmol) N-bromosuccinimide (NBS) into the flask placed in an ice bath, allow the reaction mixture to reach the room temperature slowly, and stir the mixture for 18 hours. Then remove organic solvents by rotary evaporation to obtain a crude product. Use silica gel column chromopatograpy for purification with a mixture of DCM and heptane in a radio of 1:4 as eluent. Then the main portion of the fractions is collected and concentrated to get 1.88 g deep brown viscous liquid, compound C10 with yield of 89.8%. $^1$H NMR spectrum (600 MHz, CDCl$_3$) of the compound C10: δ 8.73 (d, J=5.4 Hz, 2H), 7.38 (s, 2H), 7.21 (t, J=4.8 Hz, 2H), 2.88 (d, J=8.4 Hz, 4H), 1.87 (m, 2H), 1.29 (m, 48H), 0.85 (m, 12H).
Preparation of Organic Compound C16
chemical reaction 6
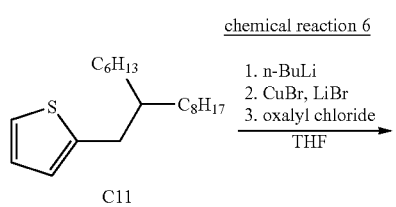
C11
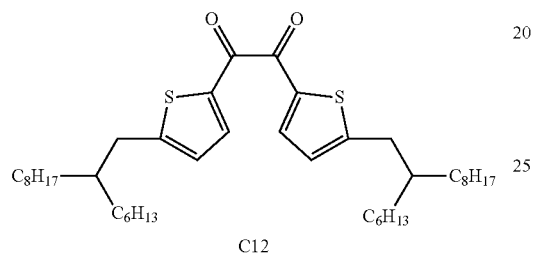
C12
chemical reaction 7
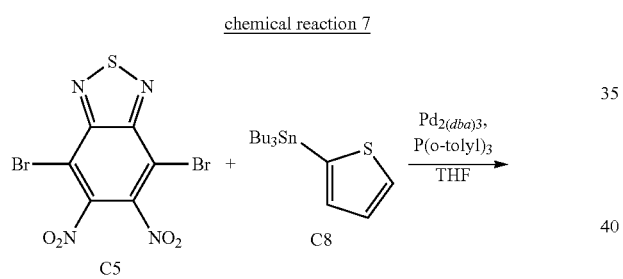
C5  C8
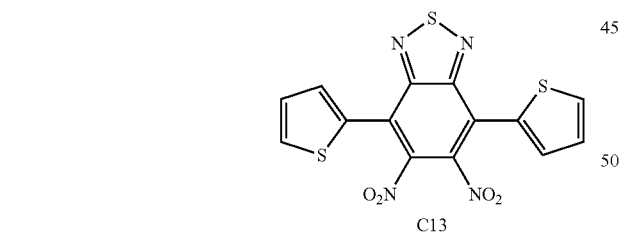
C13
chemical reaction 8
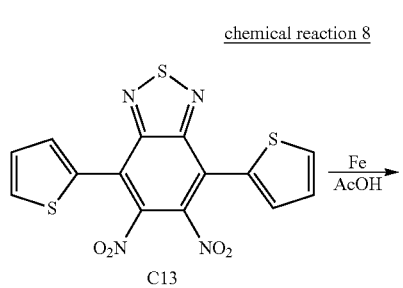
C13
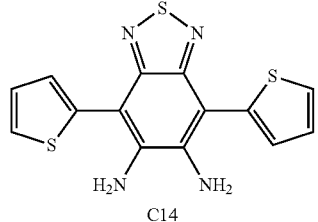
C14
chemical reaction 9
$$C14 \xrightarrow{C12}{AcOH}$$
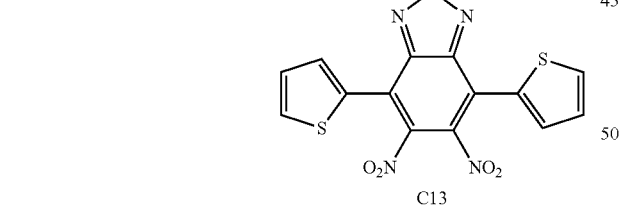
C15
chemical reaction 10
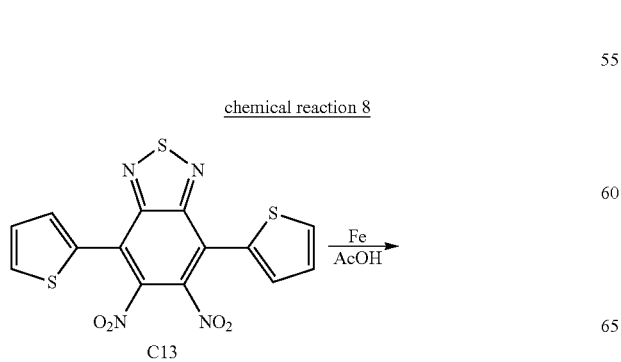
C15

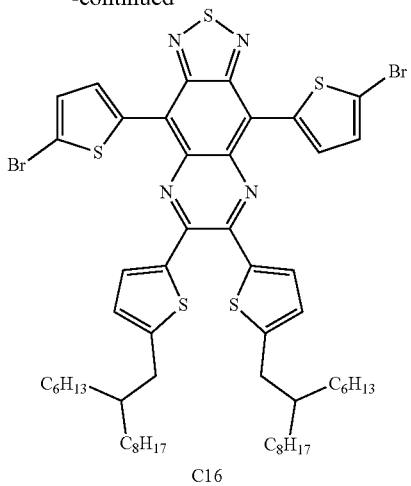

C16

Refer to chemical reaction 6, put 20 g (64.83 mmol) compound C11 into a 250 mL three neck reaction flask and add 160 mL tetrahydrofuran (THF) into the flask. Then place the flask in an ice bath and stir a mixture in the flask for one hour after adding 25.93 mL (64.83 mmol) n-butyllithium (n-BuLi) into the flask. Put 9.30 g (64.83 mmol) copper(I) bromide (CuBr) and 5.63 g (64.83 mmol) lithium bromide (LiBr) into another 500 mL three neck reaction flask, put the flask into the ice bath, and add 160 mL tetrahydrofuran (THF) into the flask. Next the reactants in the 250 mL three neck reaction flask is transferred into the 500 mL three neck reaction flask in the ice bath and is stirred for one hour. Then add 2.65 g (30.87 mmol) oxalyl chloride into the flask in the ice bath, allow the solution to reach the room temperature and stir for 18 hours. Add 100 mL water to quench reaction. After removal of THF by rotary evaporation, add 200 mL heptane, and extract with 100 mL of water three times (3×100 mL). Collect the organic layer and dry with magnesium sulfate (MgSO$_4$). After removing solvents, silica gel column is used for purification and a mixture of heptane and dichloromethane (CH$_2$Cl$_2$) in a ratio of 4:1 is used as eluent. Lastly the main portion of the fractions is collected and concentrated to obtain 9.3 g yellow orange oily liquid compound C12 with 66.6% yield $^1$H NMR spectrum (500 MHz, CDCl$_3$) of the compound C12: δ 7.87 (d, J=4.2 Hz, 2H), 7.86 (d, J=4.2 Hz, 2H), 2.82 (d, J=7.0 Hz, 4H), 1.69 (m, 2H), 1.29 (m, 48H), 0.87 (m, 12H).

Refer to chemical reaction 7, put 1 g (2.60 mmol) compound C5 and 2.33 g (6.25 mmol) compound C8 into a 100 mL three neck reaction flask and add 30 mL tetrahydrofuran (THF) into the flask. Purge out oxygen from the mixture with argon for 15 mins. Add 0.095 g (0.104 mmol) tris (dibenzylideneacetone)dipalladium and 0.126 g (0.416 mmol) tri(o-tolyl)phosphine into the flask, heat up to 66° C., and stir a mixture for 2 hours. After cooled down, filter the mixture with celite and wash with THF. Remove organic solvents by rotary evaporation and recrystallize with a mixture of isopropanol and THF. Then filter and collect solid to obtain 0.87 g compound C13 with 85.6% yield after vacuum drying. $^1$H NMR spectrum (600 MHz, CDCl$_3$) of the compound C13: δ 7.75 (dd, 2H, J=5.1 Hz, J=0.7 Hz), 7.52 (dd, 2H, J=4.7 Hz, J=1.1 Hz), 7.25 (m, 2H)

Refer to chemical reaction 8, put 0.86 g (2.20 mmol) compound C13 into a 100 mL three neck reaction flask and add 30 mL glacial acetic acid into the flask. Add 1.73 g (30.8 mmol) iron powder into a solution in the flask and heat the solution up to 80° C. to react for 5 hours with vigorous stir. Cool the reacted mixture to the room temperature, pour the reacted mixture into 200 mL water with ice, and collect solid after filtration. Wash the solid with distilled water and dry the solid by vacuum drying. Then dissolve crude product with ethyl acetate and filter the solution for removal of the iron powder. The organic solvent is removed by rotary evaporation and the residue is dried under vacuum to get 0.69 g compound C14 with 95% yield. $^1$H NMR spectrum (500 MHz, CDCl$_3$) of the compound C14: δ 7.57 (dd, 2H, J=5.5 Hz, J=1.1 Hz), 7.37 (dd, 2H, J=3.3 Hz, J=1.1 Hz), 7.26 (t, 2H, J=4.7 Hz), 4.39 (br, 4H).

Refer to chemical reaction 9, put 0.5 g (1.52 mmol) compound C14 and 1.02 g (1.52 mmol) C12 into a 100 mL three neck reaction flask. Add 15 mL glacial acetic acid in the flask. The reaction mixture is heated to 120° C. for 3 hours with vigorous stir and is cooled down to the room temperature. Pour the reacted mixture into 50 mL water with ice, extract with dichloromethane (DCM), and wash the organic layer with 50 mL distilled water three times (3×50 mL). The organic layer is dried with magnesium sulfate (MgSO$_4$) to obtain a crude product after vacuum concentration. Next the crude product is purified using silica gel column and a mixture of heptane and DCM in a ratio of 4:1 is used as eluent. Lastly the main portion of the fractions is collected and concentrated to obtain 0.75 g dark red solid compound C15 with 51.3% yield after vacuum drying. $^1$H NMR spectrum (500 MHz, CDCl$_3$) of the compound C15: δ 8.90 (d, J=7.0 Hz, 2H), 7.70 (d, J=5.0 Hz, 2H), 7.49 (d, J=3.5 Hz, 2H), 7.32 (t, J=4.5 Hz, 2H), 6.73 (d, J=3.5 Hz, 2H), 2.86 (d, J=6.5 Hz, 4H), 1.75 (m, 2H), 1.32 (m, 48H), 0.88 (m, 12H).

Refer to chemical reaction 10, put 0.75 g (0.777 mmol) compound C15 into a 100 mL three neck reaction flask and add 23 mL tetrahydrofuran (THF) into the flask under nitrogen atmosphere. Add 0.318 g (1.787 mmol) N-bromosuccinimide into the flask under ice bath, then allow a mixture to be warmed to room temperature and stirred for 18 hours. Then remove organic solvents by rotary evaporation. Next use silica gel column chromopatogrphy for purification with a mixture of DCM and heptane in a radio of 1:4 as eluent. Then the main portion of the fractions is collected and concentration to get 0.81 g deep brown viscous liquid compound C16 with 92.8% yield. $^1$H NMR spectrum (600 MHz, CDCl$_3$) of the compound C16: δ 8.77 (d, J=4.0 Hz, 2H), 7.47 (d, J=3.5 Hz, 2H), 7.22 (d, J=4.0 Hz, 2H), 6.75 (d, J=3.5 Hz, 2H), 2.88 (d, J=6.5 Hz, 4H), 1.87 (m, 2H), 1.29 (m, 48H), 0.87 (m, 12H).

Preparation of Organic Compound C21

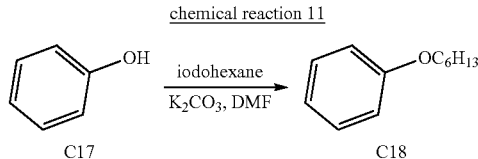

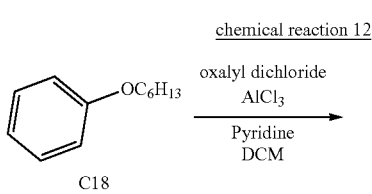

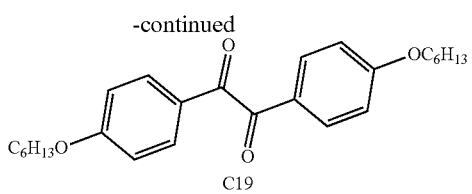

C19 chemical reaction 13

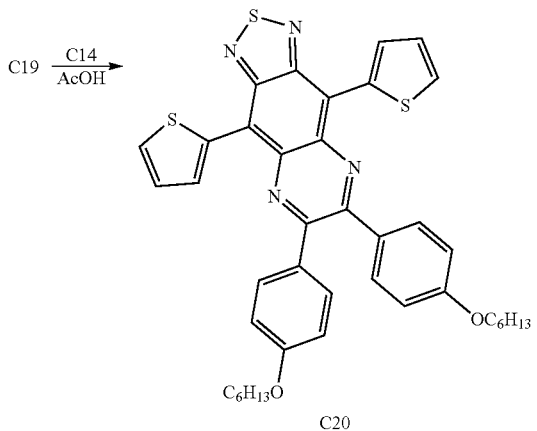

chemical reaction 14

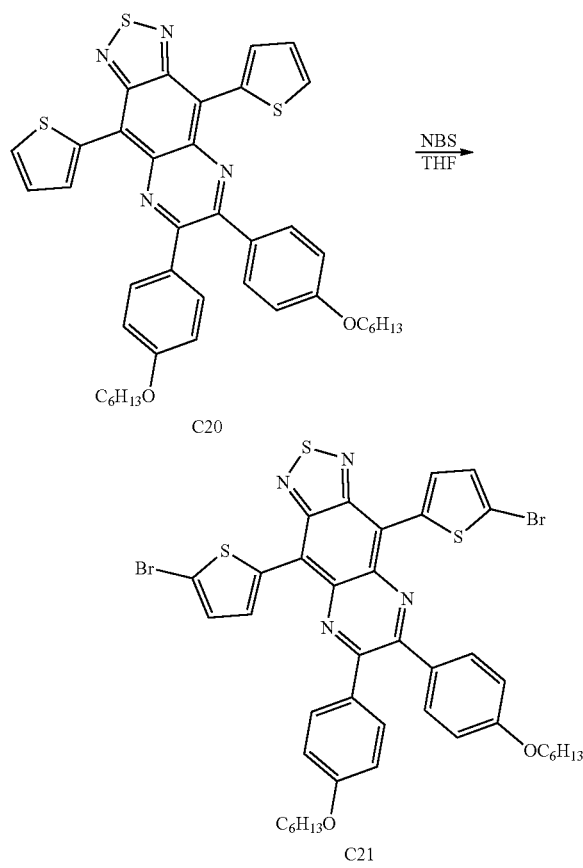

Refer to chemical reaction 11, put 2.00 g (21.25 mmol) compound C17, 2.82 mL (19.13 mmol) 1-iodohexane, and 2.94 g (21.25 mmol) sodium carbonate into a 100 mL two neck reaction flask and add 40 mL dimethylformamide (DMF) into the flask. Heat mixture up to 90° C. and react for 18 hours. After reaction and cooling down, add water and ethyl acetate for extraction. Take the organic layer and dry with magnesium sulfate ($MgSO_4$), and remove organic solvents by rotary evaporation. Next use silica gel column for purification with a mixture of heptane and DCM in a radio of 1:5 as eluent. Then the main portion of the fractions is collected and concentrated to get 2.70 g transparent liquid compound C18 with 71.2% yield. $^1$H NMR spectrum (600 MHz, $CDCl_3$) of the compound C18: δ 7.28 (m, 1H), 6.91 (m, 4H), 3.96 (t, J=7.8 Hz, 2H), 1.79 (m, 2H), 1.49 (m, 6H), 0.92 (m, 3H).

Refer to chemical reaction 12, put 1.17 g (8.8 mmol) aluminum chloride, ($AlCl_3$) into a 100 mL three neck flask and add 25 mL anhydrous DCM into the flask. Under argon atmosphere, the flask is cooled down to −20° C. and add 0.254 g (2.0 mmol) oxalyl chloride into the flask. Then allow the reaction mixture to reach 0° C. and add 0.783 g (4.4 mmol) compound C18 and 0.16 mL (2.0 mmol) anhydrous pyridine which are dissolved in 5 mL anhydrous DCM into the three neck flask. Allow the reaction mixture to reach the room temperature slowly and react for 18 hours. Then add 100 mL water to quench reaction and extract with DCM and water. Take the organic layer and dry with magnesium sulfate. Remove organic solvents by rotary evaporation. Next use silica gel column for purification with a mixture of ethyl acetate and heptane in a radio of 1:2 as eluent. Then the main portion of the fractions is collected and concentrated to obtain 0.36 g white solid product, compound C19 with 43.6% yield. $^1$H NMR spectrum (500 MHz, $CDCl_3$) of the compound C19: δ 7.22 (d, J=8.5 Hz, 4H), 6.94 (d, J=8.5 Hz, 4H), 4.03 (t, J=6.5 Hz, 4H), 1.81 (m, 4H), 1.38 (m, 12H), 0.91 (m, 6H).

Refer to chemical reaction 13, put 0.202 g (0.492 mmol) compound C19 and 0.17 g (0.517 mmol) compound C14 into a 100 mL two neck reaction flask and then add 20 mL acetic acid into the flask under nitrogen atmosphere. Heat the reaction mixture up to 120° C. and react for 18 hours. Pour mixture into water to quench reaction and extract with DCM and water. Take the organic layer and dry with magnesium sulfate. Remove organic solvents by rotary evaporation. Next use silica gel column for purification with a mixture of DCM and heptane in a radio of 1:2 as eluent. Then the main portion of the fractions is collected and concentrated to obtain 0.31 g dark green solid, compound C20 with 89.0% yield. $^1$H NMR spectrum (500 MHz, $CDCl_3$) of the compound C20: δ 8.99 (d, J=3.5 Hz, 2H), 7.80 (d, J=9.0 Hz, 4H), 7.68 (d, J=5.5 Hz, 2H), 7.32 (m, 2H), 6.94 (d, J=9.0 Hz, 4H), 4.03 (t, J=6.5 Hz, 4H), 1.83 (m, 4H), 1.38 (m, 12H), 0.91 (m, 6H).

Refer to chemical reaction 14, put 0.30 g (0.426 mmol) compound C20 and 9 mL THF into a 100 mL two neck flask. With an ice bath and under nitrogen atmosphere, slowly add 0.167 g (0.937 mmol, 2.2 equiv.) N-bromosuccinimide into the flask. Then react at the room temperature for 18 hours. Add water to quench reaction and extract with DCM and water. Take the organic layer and dry with magnesium sulfate. Remove organic solvents by rotary evaporation. Next use silica gel column for purification with a mixture of DCM and heptane in a radio of 2:3 as eluent. Then the main portion of the fractions is collected and concentrated to obtain 0.296 g dark green solid, compound C21 with 80.6% yield. $^1$H NMR spectrum (500 MHz, CDCl$_3$) of the compound C21: δ 8.87 (d, J=4.0 Hz, 2H), 7.20 (d, J=8.5 Hz, 4H), 7.23 (d, J=4.0 Hz, 2H), 6.95 (d, J=8.5 Hz, 4H), 4.05 (t, J=6.5 Hz, 4H), 1.83 (m, 4H), 1.38 (m, 12H), 0.91 (m, 6H)

Preparation of Organic Compound C25 chemical reaction 15

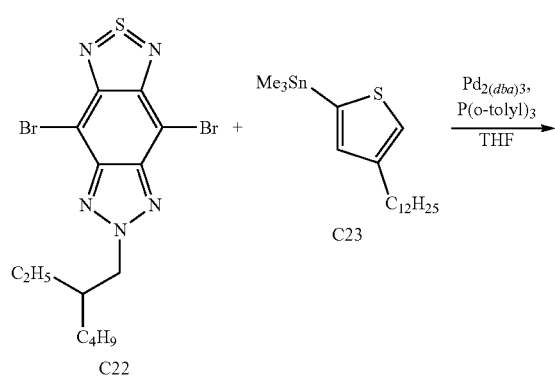

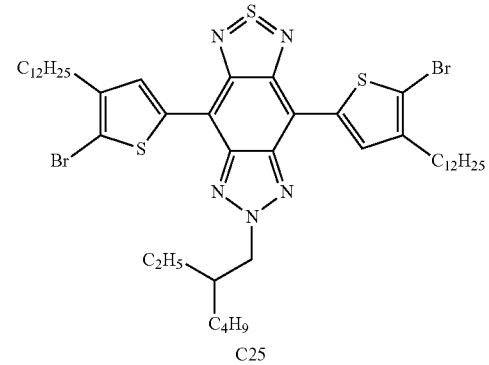

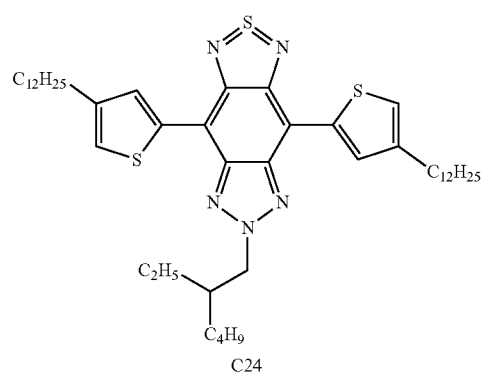

chemical reaction 16

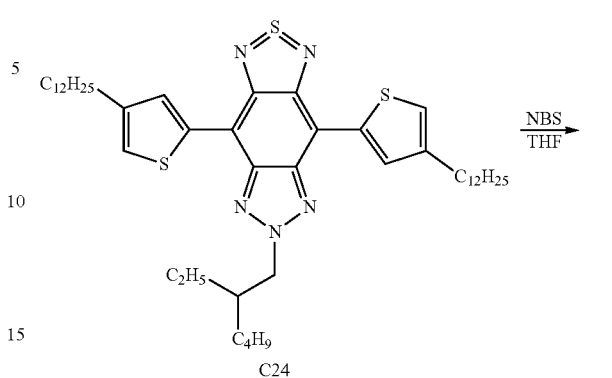

Refer to chemical reaction 15, put 1.0 g (2.226 mmol) compound C22 and 2.4 g (5.779 mmol) compound C23 into a 100 mL three neck reaction flask and add 45 mL tetrahydrofuran (THF) into the flask. The reaction mixture is purged with argon for 15 mins. Add 0.082 g (0.090 mmol) tris(dibenzylideneacetone)dipalladium and 0.108 g (0.355 mmol) tri(o-tolyl)phosphine into the flask, heat up to 66° C., and stir for 2 hours. After being cooled down, filter the mixture with celite and wash the mixture with heptane. Remove organic solvents by rotary evaporation. Next use silica gel column chromatography for purification with a mixture of DCM and heptane in a radio of 1:4 as eluent. Then the main portion of the fractions is collect and concentrated to obtain 1.64 g brown viscous liquid, compound C24 with 93.2% yield. $^1$H NMR spectrum (600 MHz, CDCl$_3$) of the compound C24: δ 8.69 (s, 2H), 7.23 (s, 2H), 4.91 (d, J=7.2 Hz, 2H), 2.76 (m, 4H), 2.38 (s, 1H), 1.74 (m, 4H), 1.38 (m, 2H), 1.07 (m, 42H), 0.89 (in, 12H)

Refer to chemical reaction 16, put 1.0 g (1.265 mmol) compound C24 into a 100 mL three neck reaction flask and add 45 mL THF into the flask under nitrogen atmosphere. Put the flask into an ice bath, add 0.450 g (2.528 mmol) N-bromosuccinimide (NBS), and stir at room temperature for 18 hours. Remove organic solvents by rotary evaporation. Next use column chromatography for purification with a mixture of DCM and heptane in a radio of 1:4 as eluent. Then the main portion of the fractions is collected and concentrated to obtain 1.15 g dark brown viscous liquid, compound C25 with 95.6% yield. $^1$H NMR spectrum (600 MHz, CDCl$_3$) of the compound C25: δ 8.54 (s, 2H), 4.95 (m, 2H), 2.70 (m, 4H), 2.38 (s, 1H), 1.74 (m, 4H), 1.38 (m, 2H), 1.07 (m, 42H), 0.88 (m, 12H).

Preparation of Organic Semiconducting Compound DP1

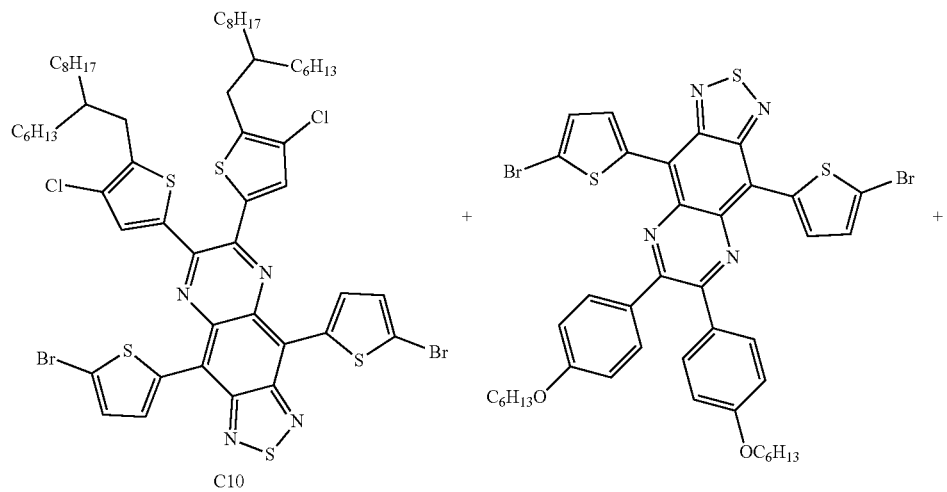

C10

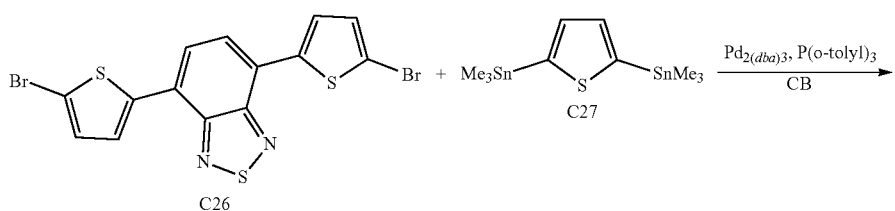

C26, C27

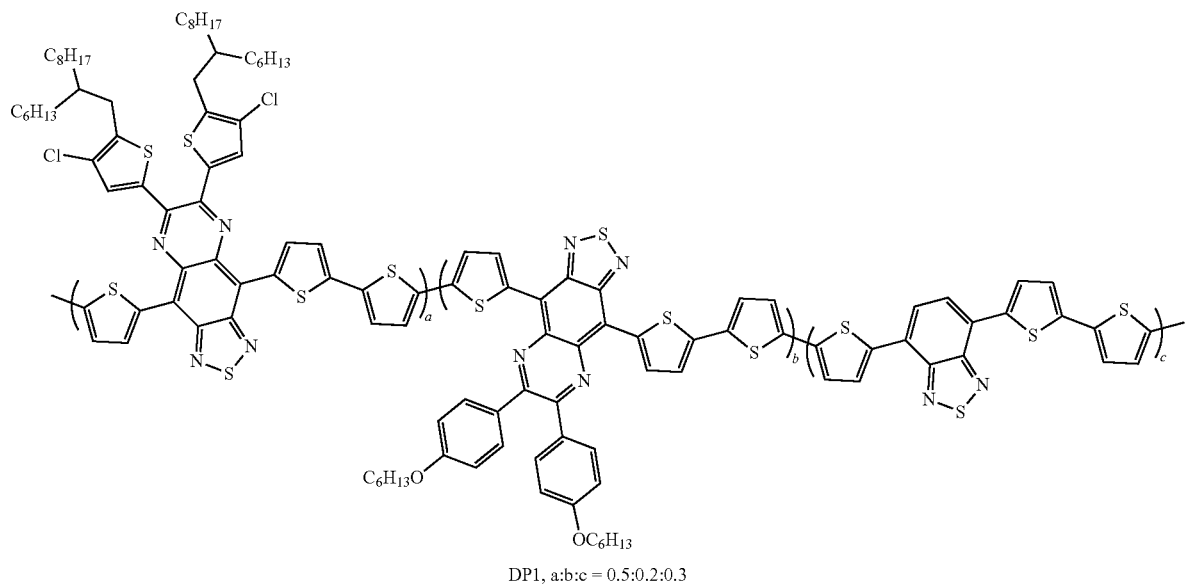

DP1, a:b:c = 0.5:0.2:0.3

Put 0.15 g (0.366 mmol) compound C27, 0.218 g (0.183 mmol) compound C10, 0.063 g, (0.073 mmol) compound C21, and 0.050 g (0.109 mmol) compound C26 into a 100 mL three neck reaction flask and add 36.6 mL chlorobenzene into the flask. The reaction mixture is purged with argon for 15 mins. Add 3.35 mg (0.0037 mmol) tris(dibenzylideneacetone)dipalladium and 4.46 mg (0.0147 mmol) tri(o-tolyl)phosphine into the flask, heat up to 130° C., and react for 0.5 hour. Pour the mixture into 70 mL methanol and then filter and collect solid. Soxhlet extraction with methanol and ethyl acetate. The residual solid is dried under vacuum to get 0.258 g DP1 with 85.0% yield.

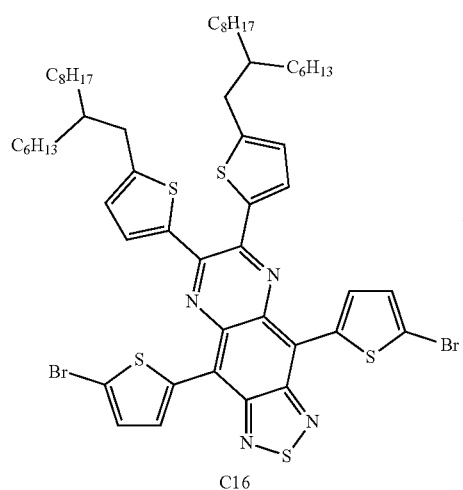

C16

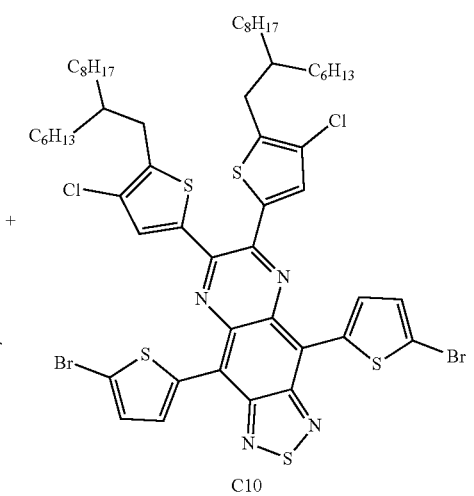

C10

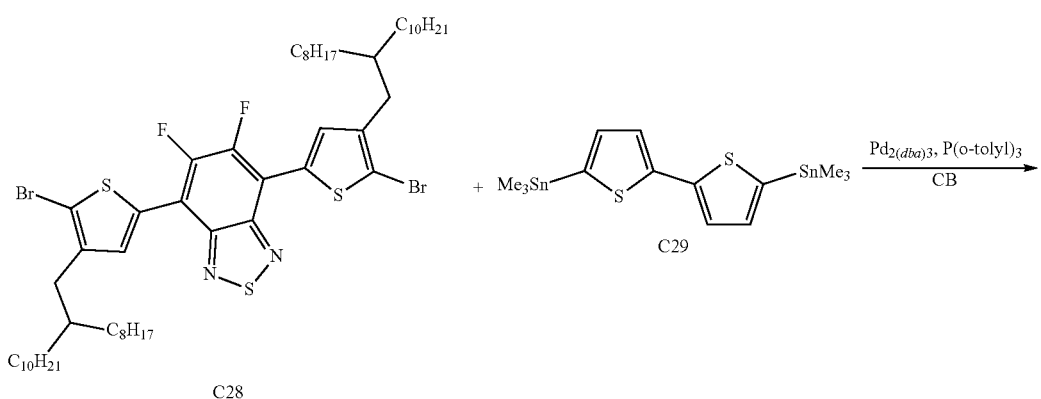

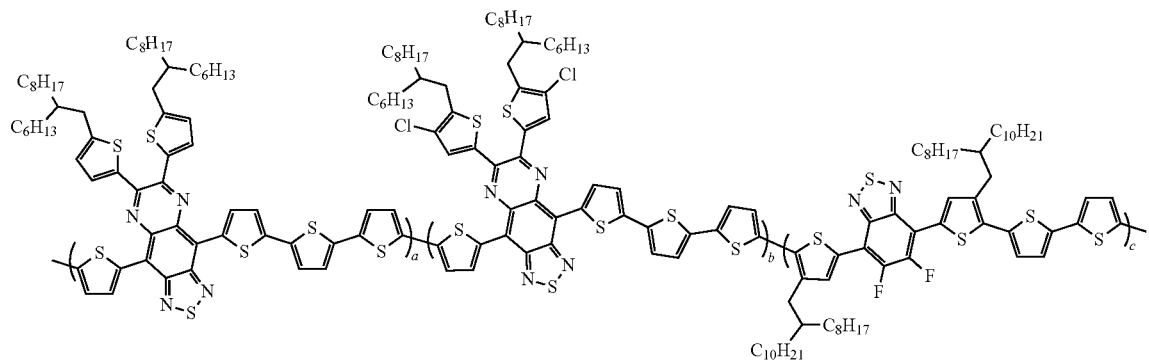

DP2, a:b:c = 0.3:0.5:0.2

Put 0.1234 g (0.110 mmol) compound C16, 0.218 g (0.183 mmol) compound C10, 0.0773 g (0.073 mmol) compound C28, and 0.180 g (0.366 mmol) compound C29 into a 100 mL three neck reaction flask and add 36.6 mL chlorobenzene into the flask. The reaction mixture is purged with argon for 15 mins. Add 3.35 mg (0.0037 mmol) tris(dibenzylideneacetone)dipalladium and 4.46 mg (0.0147 mmol) tri(o-tolyl)phosphine into the flask, heat up to 130° C., and stir mixture for 1 hour. Pour the mixture into 70 mL methanol and then filter and collect solid. Soxhlet extraction of the solid with methanol and ethyl acetate. The residual solid is dried under vacuum to get 0.20 g DP2 with 95.0% yield.

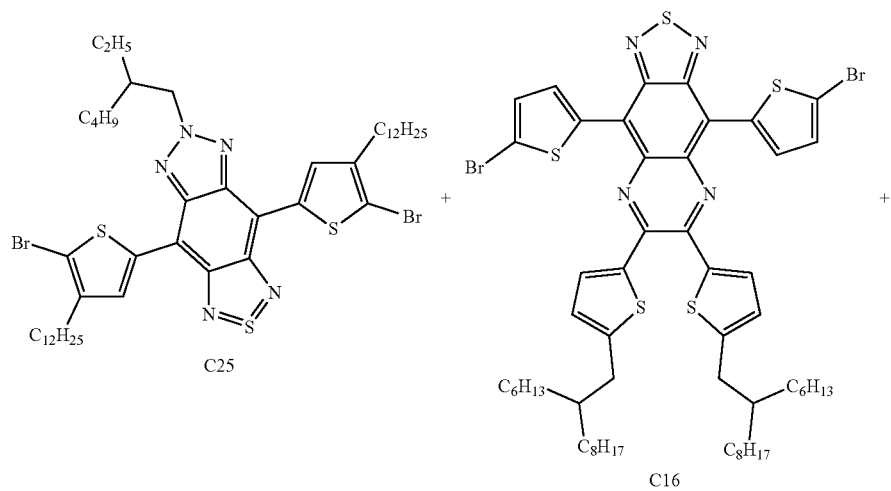

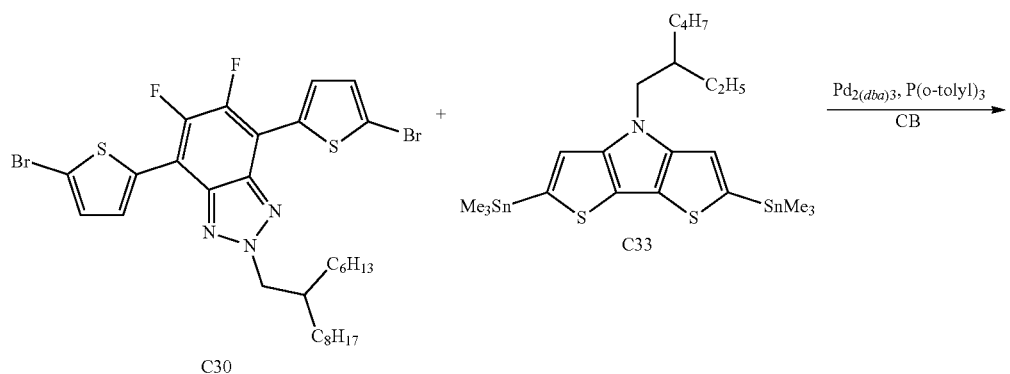

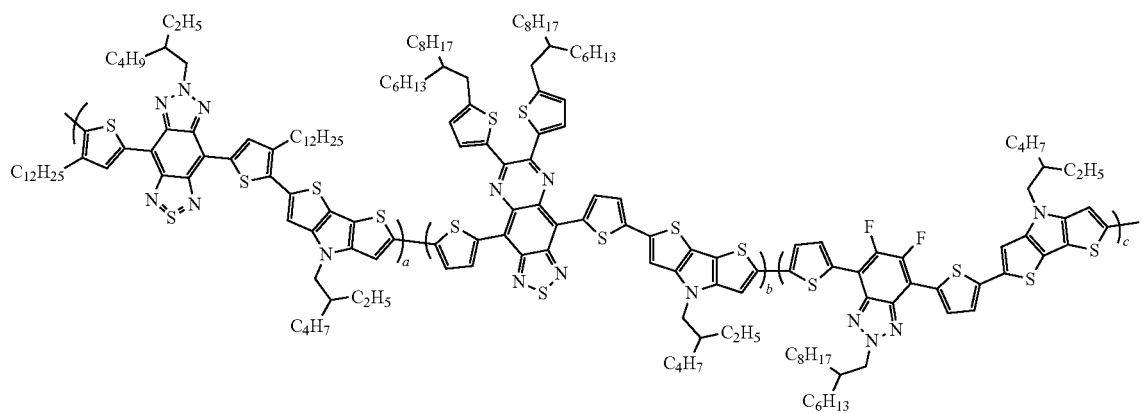

DP5, a:b:c = 0.4:0.4:0.2

Put 0.0355 g (0.0374 mmol) compound C25, 0.042 g (0.0374 mmol) compound C16, 0.0131 g (0.0187 mmol) C30, and 0.0576 g (0.0935 mmol) compound C33 into a 100 mL three neck reaction flask and add 20 mL chlorobenzene into the flask. The reaction mixture is purged with argon for 15 mins. Add 0.86 mg (0.0009 mmol) tris(dibenzylideneacetone)dipalladium and 1.14 mg (0.0004 mmol) tri(o-tolyl)phosphine into the flask, heat up to 130° C., and stir mixture for 1 hour. Pour the mixture into 40 mL methanol to have precipitate and then filter and collect solid. Soxhlet extraction of the solid with methanol and ethyl acetate. The residual solid is dried under vacuum to get 0.091 g DP5 with 88.6% yield.

A plurality of embodiments of organic semiconducting compounds according to the present invention is shown in table 1.

TABLE 1
embodiments of organic semiconducting compounds
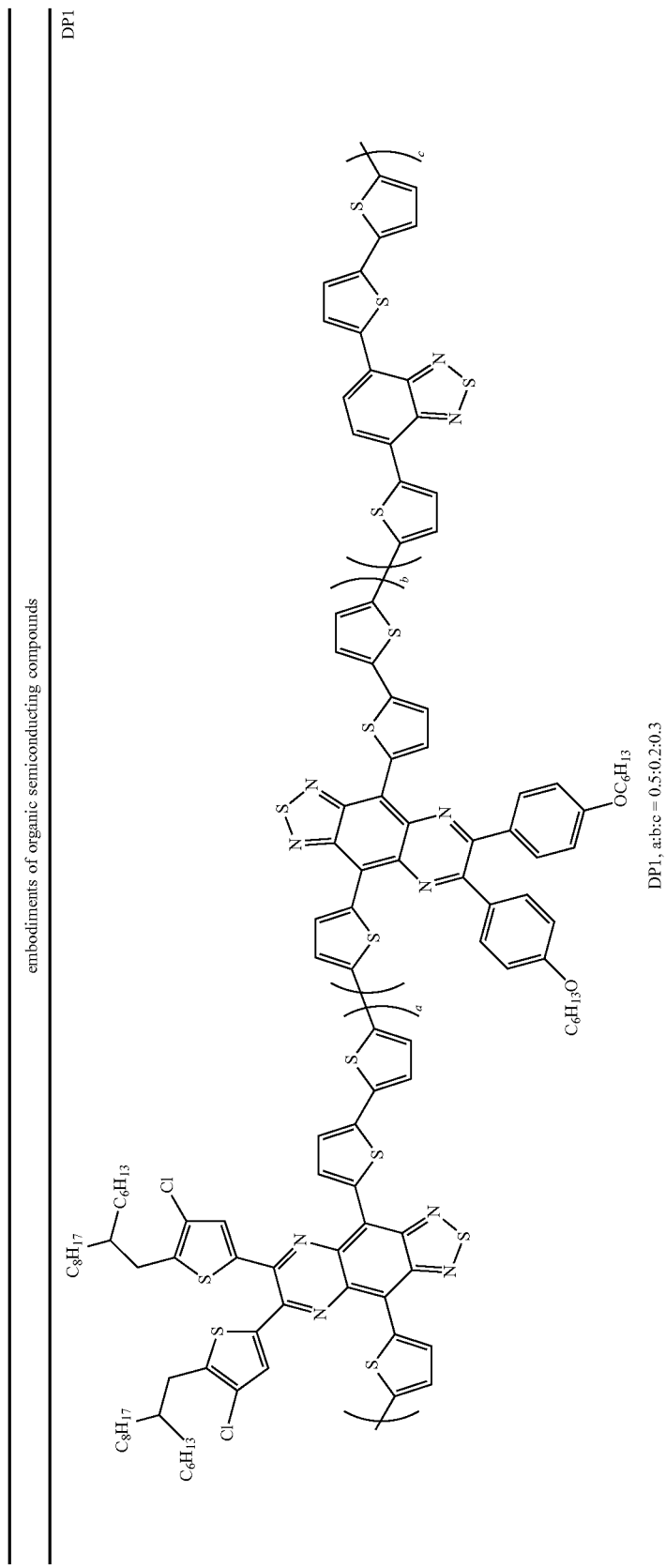
DP1, a:b:c = 0.5:0.2:0.3

TABLE 1-continued
embodiments of organic semiconducting compounds
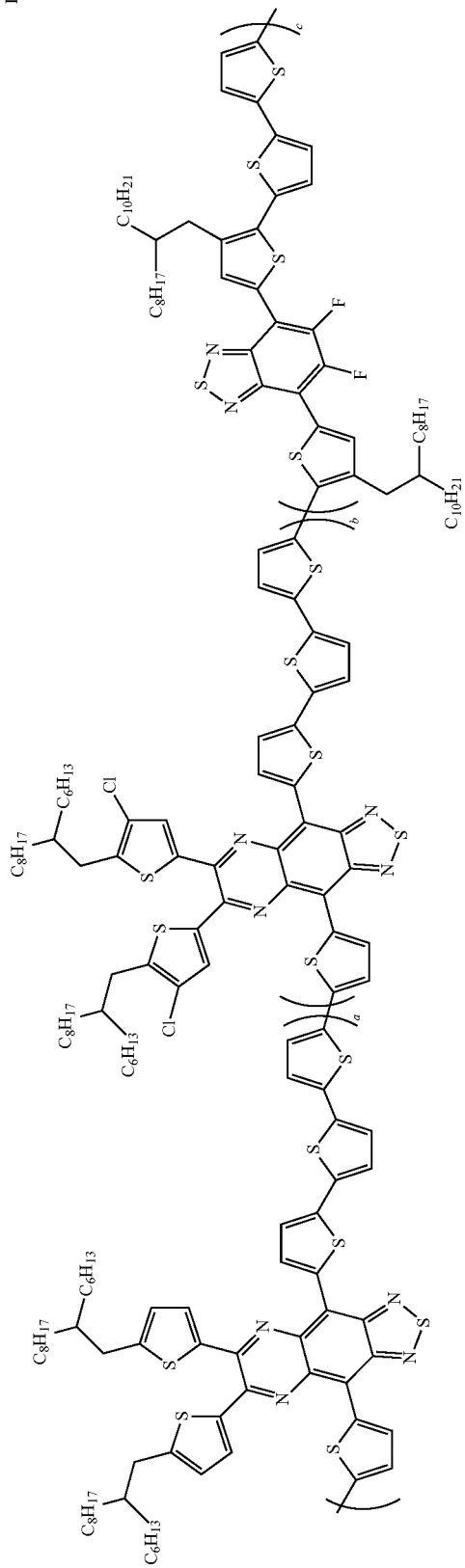
DP2, a:b:c = 0.3:0.5:0.2
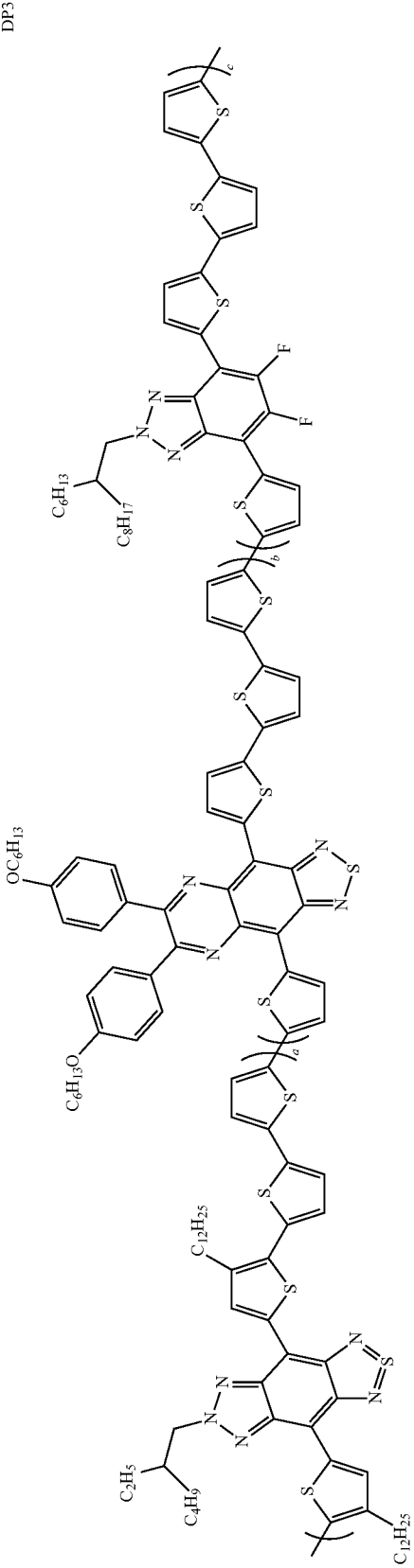
DP3, a:b:c = 0.6:0.2:0.2

TABLE 1-continued
embodiments of organic semiconducting compounds
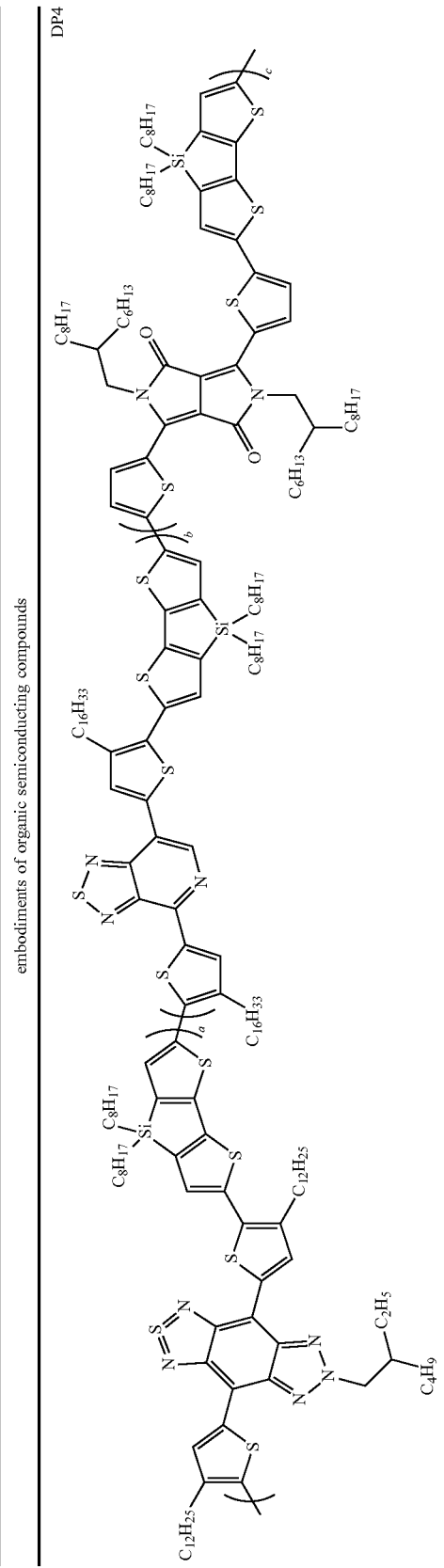
DP4, a:b:c = 0.6:0.2:0.3    DP4

TABLE 1-continued
embodiments of organic semiconducting compounds
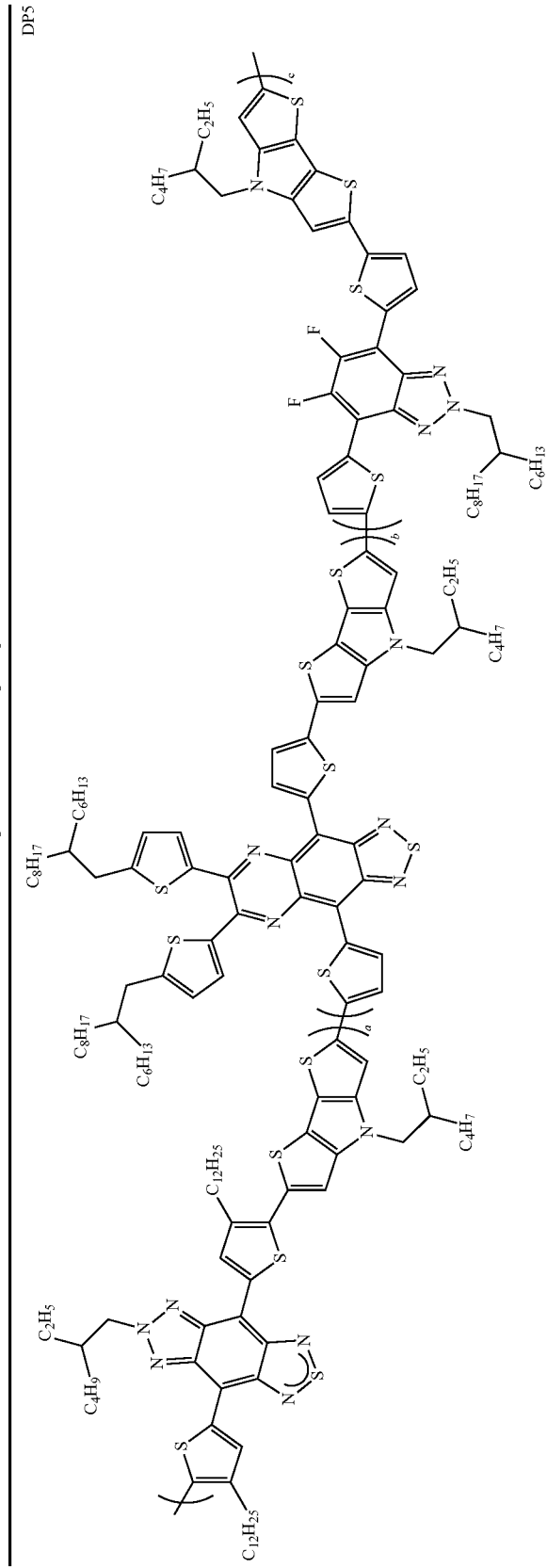
DP5, a:b:c = 0.4:0.4:0.2    DP5

TABLE 1-continued
embodiments of organic semiconducting compounds
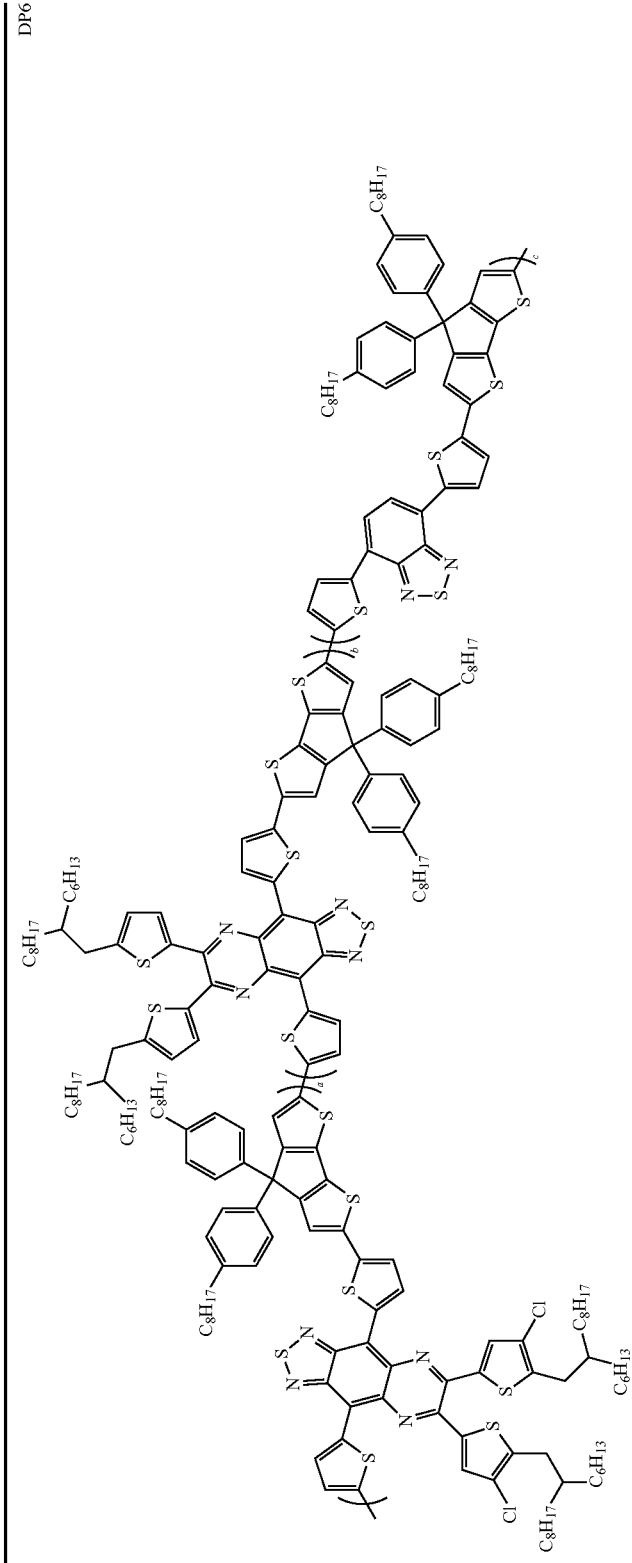
DP6, a:b:c = 0.6:0.1:0.3 | DP6

TABLE 1-continued
embodiments of organic semiconducting compounds
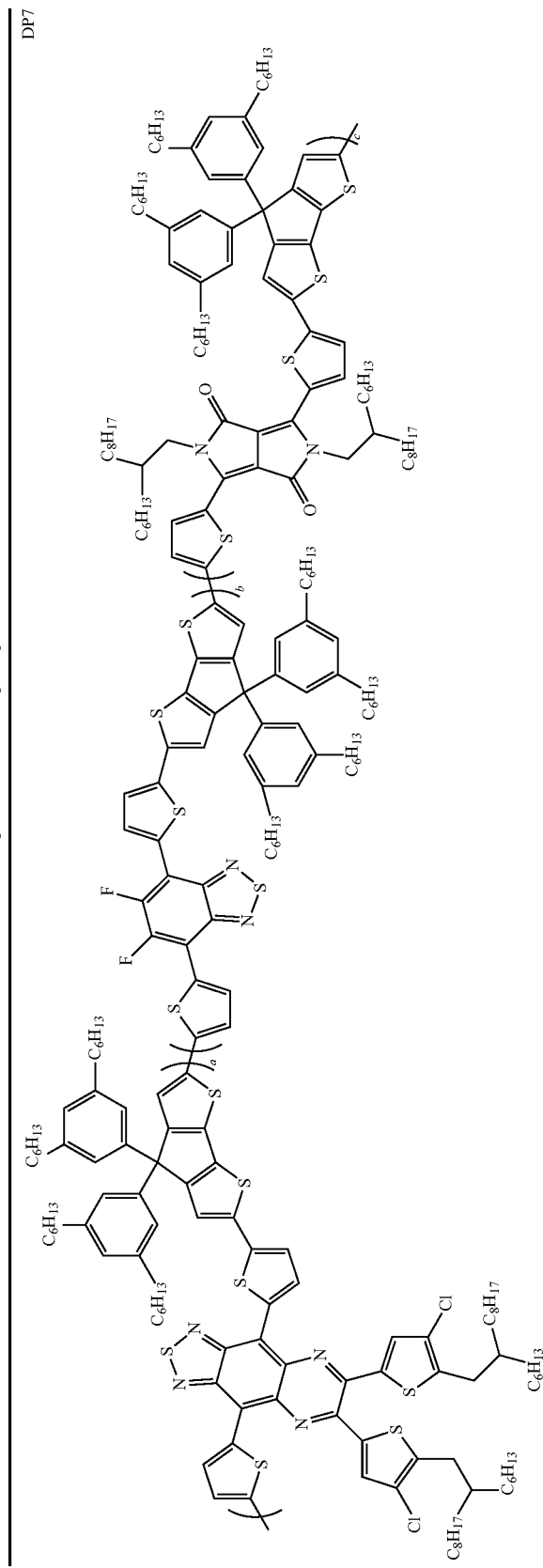
DP7, a:b:c = 0.4:0.2:0.4

TABLE 1-continued
embodiments of organic semiconducting compounds
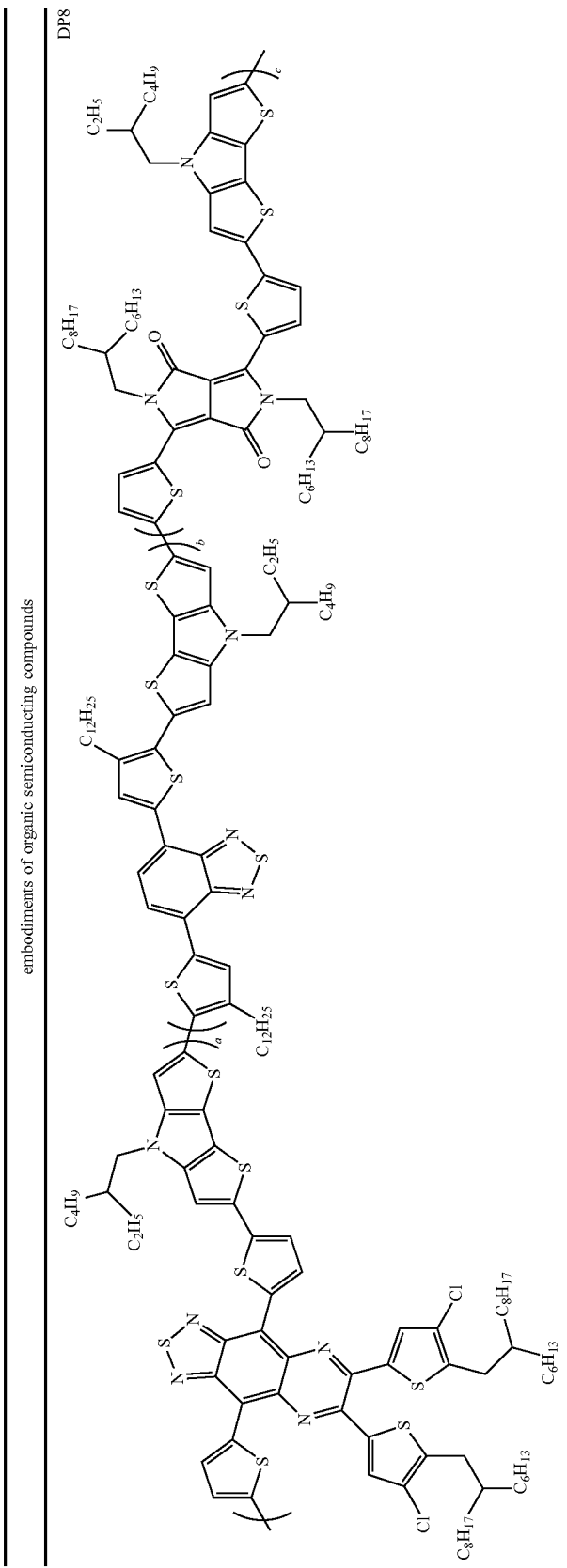
DP8, a:b:c = 0.4:0.2:0.4

TABLE 1-continued
embodiments of organic semiconducting compounds
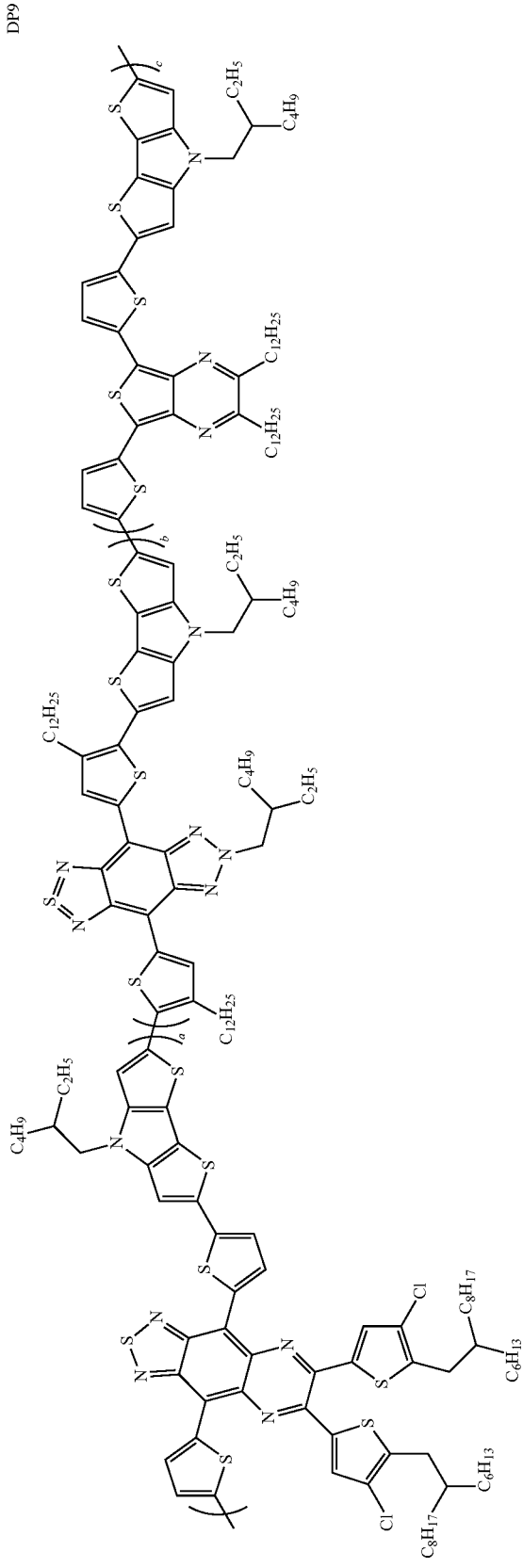
DP9, a:b:c = 0.6:0.3:0.1

TABLE 1-continued
embodiments of organic semiconducting compounds
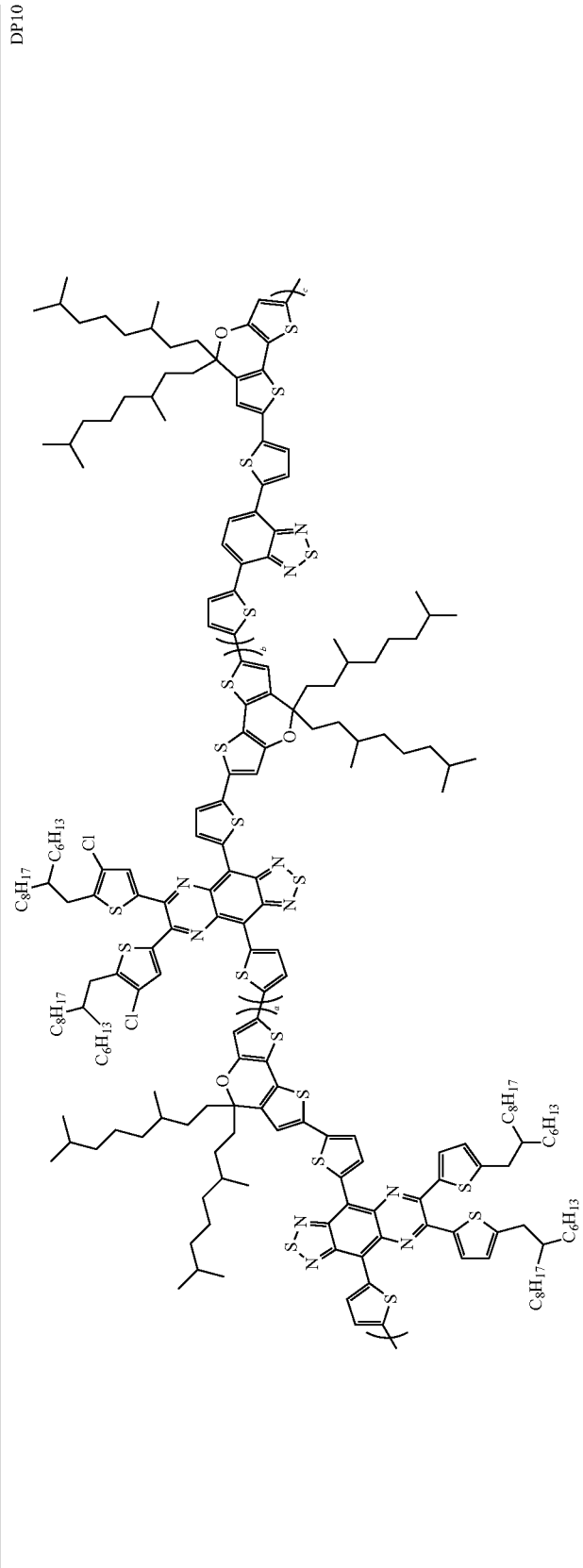
DP10
DP10, a:b:c = 0.4:0.4:0.2

TABLE 1-continued
embodiments of organic semiconducting compounds
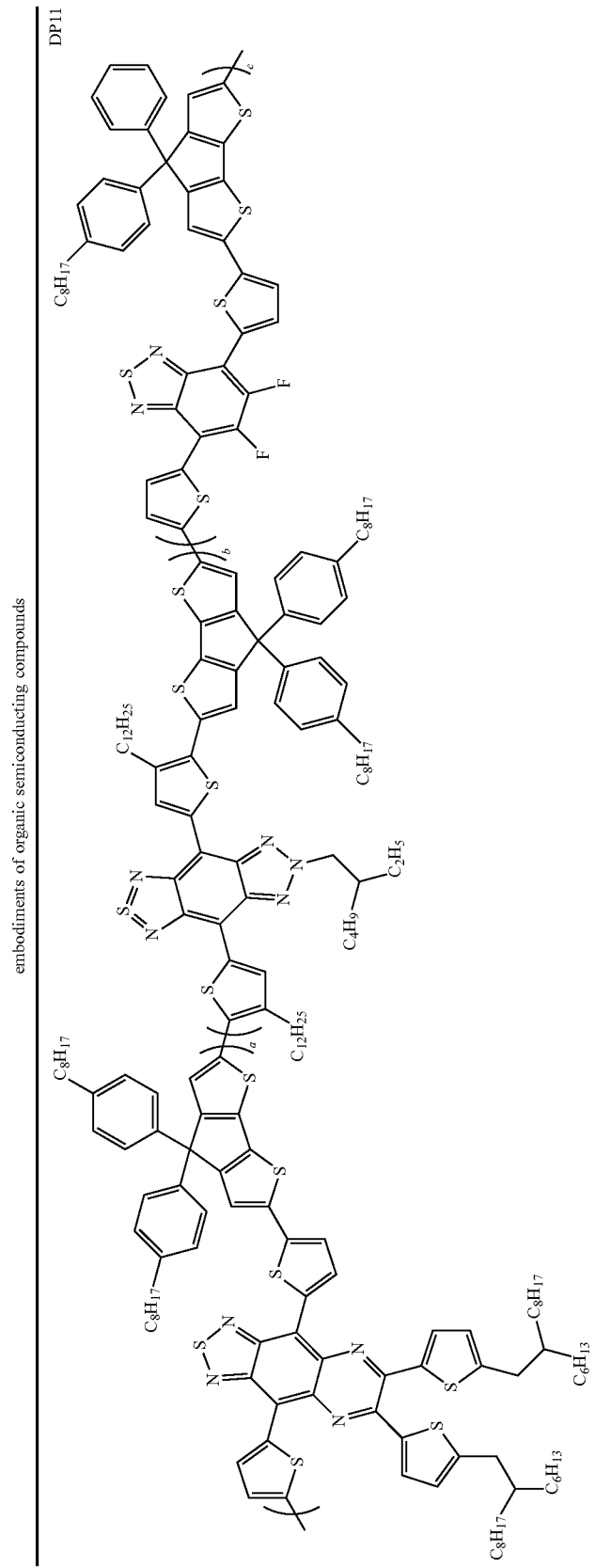
DP11
DP11, a:b:c = 0.5:0.3:0.2

TABLE 1-continued
embodiments of organic semiconducting compounds
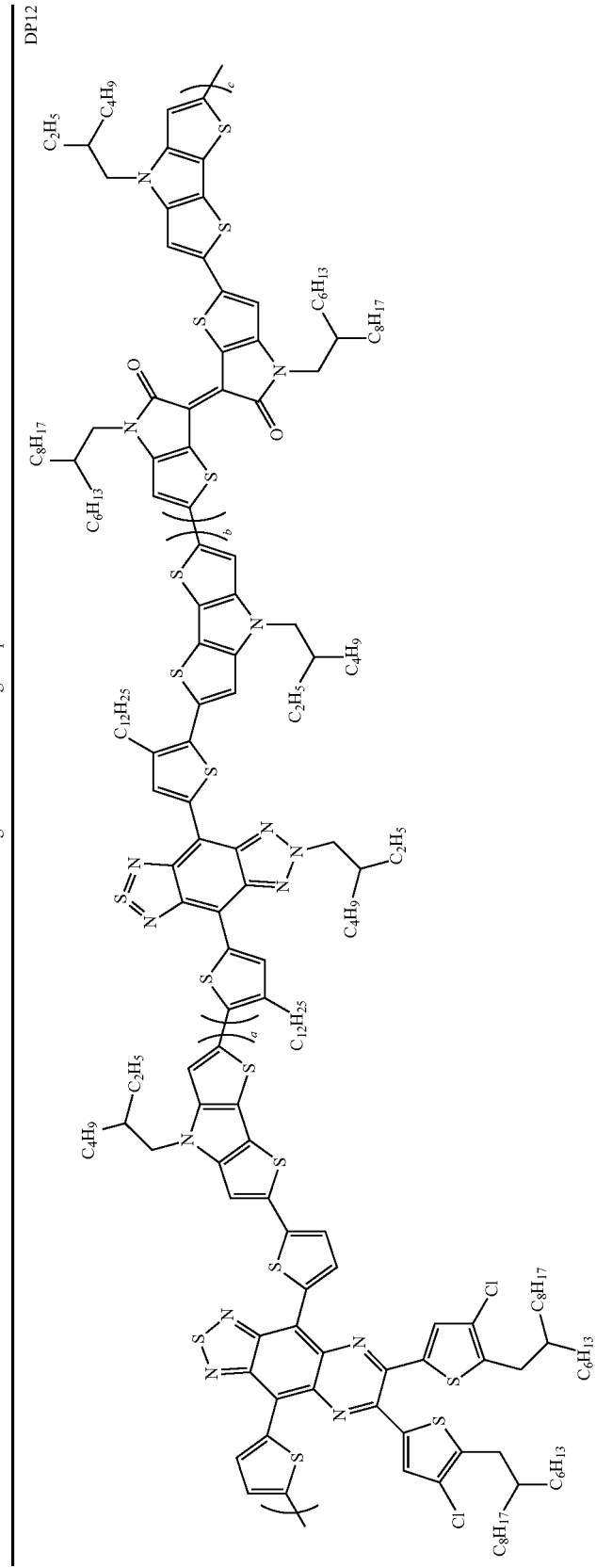
DP12
DP12, a:b:c = 0.5:0.3:0.2

TABLE 1-continued
embodiments of organic semiconducting compounds
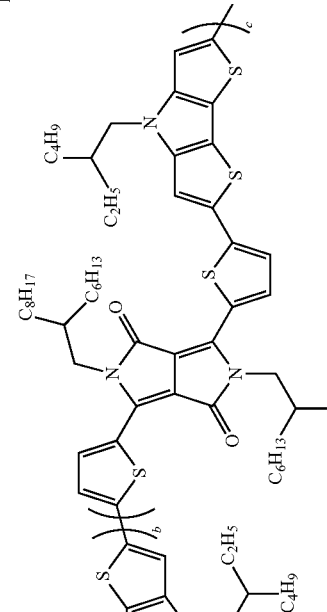
DP13, a:b:c = 0.7:0.1:0.2

The organic semiconducting compounds according to the present invention can be used as electron donors or p-type semiconductors of organic photoelectric components and suitable for preparing blends of n-type and p-type semiconductors applied to fields such as organic photodetector components. The terms n-type or n-type semiconductors are to be understood as extrinsic semiconductors which have a larger electron concentration than hole concentration while the terms p-type or p-type semiconductors are to be understood as extrinsic semiconductors which have a larger hole concentration than electron concentration (also shown in J. Thewlis, *Concise Dictionary of Physics*, Pergamon Press, Oxford, 1973).

In order to process the organic semiconducting compound of the present invention, at least one small molecule compound and/or polymer with at least one of the following features including charge transfer, semiconductivity, electrical conductivity, photoconductivity, hole blocking, and electron blocking is added and blended for preparation of a first component.

Moreover, the organic semiconducting compound can be mixed with at least one of the following organic solvents including aliphatic hydrocarbons, chlorinated hydrocarbon, aromatic hydrocarbons, ketones, ethers, and combinations thereof such as toluene, o-xylene, p-xylene, 1,3, 5- or 1, 2, 4-trimethylbenzene, tetrahydrofuran, and 2-methyltetrahydrofuran for preparing a second component.

The organic semiconducting compound can be used in a patterned organic semiconductor layer in a device. As to modern microcomputer applications, patterning of the thin organic semiconductor layer for production of small structure or patterns can be achieved by photolithography, electron-beam lithography, or laser patterning. Thus, the cost is reduced (more devices per unit area) and power consumption is reduced.

In order to form thin layers in electronics or optoelectronic devices, the first or second component formed by the present organic semiconducting compound can be deposited by suitable ways. For example, liquid coating is better than vacuum deposition. The second component formed by the present organic semiconducting compound can make a plurality of liquid coating techniques become feasible.

Preferred deposition ways include but not limited to dip coating, spin coating, ink-jet printing, nozzle-printing, relief printing, screen printing, gravure printing, blade coating, roller printing, reverse roll coating, planographic printing, dry offset printing, flexographic printing, web printing, spray coating, curtain coating, brush coating, slot-dye coating or pad printing.

An organic photoelectric component containing the present organic semiconducting compounds, the first component formed by the organic semiconducting compounds, or the second component formed by the organic semiconducting compounds is also provided. The organic photoelectric component includes a substrate, an electrode module disposed on the substrate and provided with a first electrode and a second electrode, and an active layer arranged between the first electrode and the second electrode and made from materials containing at least one organic compound. At least one of the two electrodes, the first electrode and the second electrode, is transparent or semi-transparent.

In a preferred embodiment shown in FIG. 1A, an organic photoelectric component 10 includes a substrate 100, an electrode module 110, and an active layer 120. The electrode module 110 which consists of a first electrode 112 and a second electrode 114 is disposed over the substrate 100 while the active layer 120 is arranged between the first electrode 112 and the second electrode 114. The first electrode 112 is located between the substrate 100 and the active layer 120 while the second electrode 114 is located above the active layer 120.

In this embodiment, the active layer 120 includes at least one of organic semiconducting compounds of the present invention. At least one of the two electrodes, the first electrode 112 and the second electrode 114, is transparent or semi-transparent.

Figure 1B:

In another embodiment, refer to FIG. 1B, an organic photoelectric component 10 includes a substrate 100, an electrode module 110, and an active layer 120. The electrode module 110 is disposed over the substrate 100 and provided with a first electrode 112 and a second electrode 114 while the active layer 120 is arranged between the first electrode 112 and the second electrode 114. The second electrode 114 is located between the substrate 100 and the active layer 120 while the first electrode 112 is located above the active layer 120.

The substrate 100 is preferred to be a glass substrate or a transparent soft substrate with mechanical strength, hot strength, and transparency. Materials for the transparent soft substrate include polyethylene, ethylene vinyl acetate copolymer, ethylene-vinyl alcohol copolymer, polypropylene, polystyrene, poly (methyl methacrylate), polyvinyl chloride, polyvinyl alcohol, polyvinyl butyral, nylon, polyetheretherketone, polysulfone, polyethersulfone, tetrafluoroethylene perfluoroalkyl vinyl ether copolymer, polyvinyl fluoride, ethylene-tetrafluoroethylene copolymer, tetrafluoroethylene-hexafluoropropylene copolymer, polychlorotrifluoroethylene, polyvinylidene difluoride, polyester, polycarbonate, polyurethane, polyimide, etc.

The first electrode 112 is made of metal oxides and their fluorine-doped derivatives such as transparent indium oxides, tin oxides, fluorine-doped tin oxide (FTO) or complex metal oxides including indium tin oxide (ITO), indium zinc oxide (IZO), etc.

The second electrode 114 can be made of metal oxides, metals (silver, aluminum, gold), conductive polymer, carbon-based conductors, metal compounds, or conductive films formed by combinations of the above materials.

In a preferred embodiment, the active layer 120 of the organic photoelectric component 10 includes at least one p-type organic semiconducting compound such as the organic semiconducting compounds of the present invention mentioned above and at least one n-type organic semiconducting compound.

In a preferred embodiment, the n-type organic semiconducting compound of the organic photoelectric component 10 has the following chemical formula:

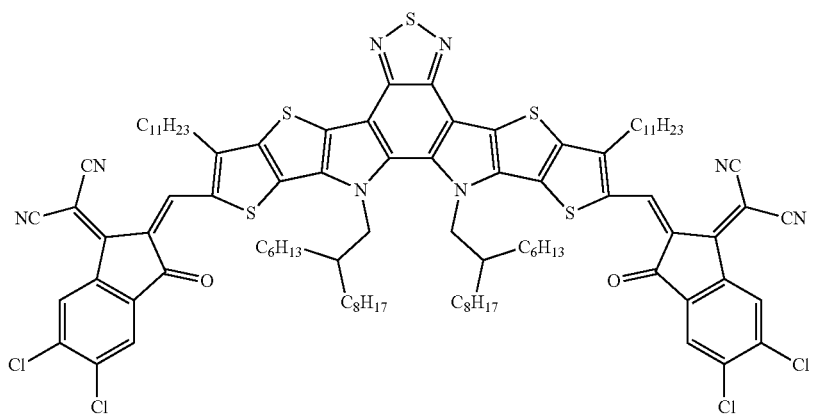
N1
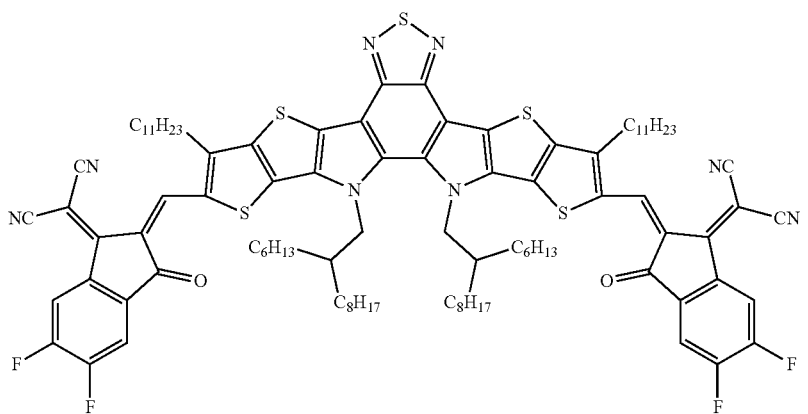
N2
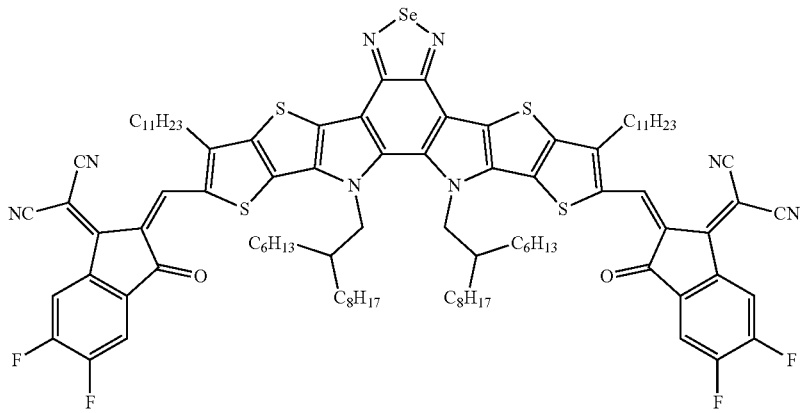
N3
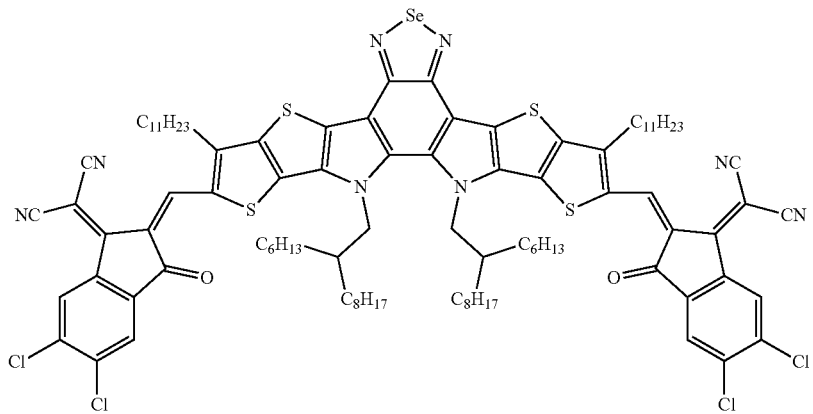
N4

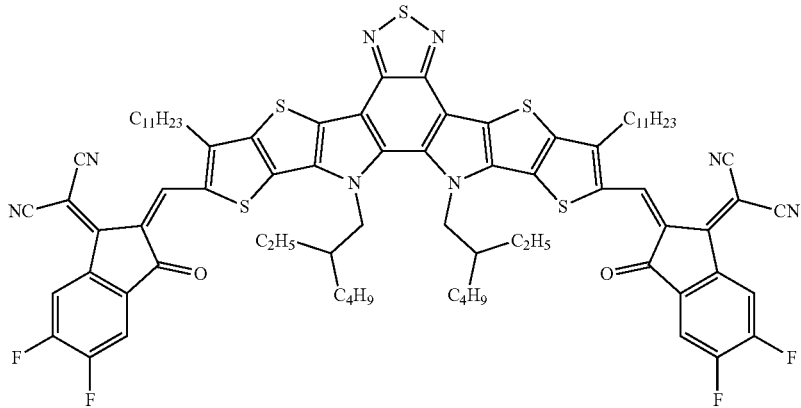
N5
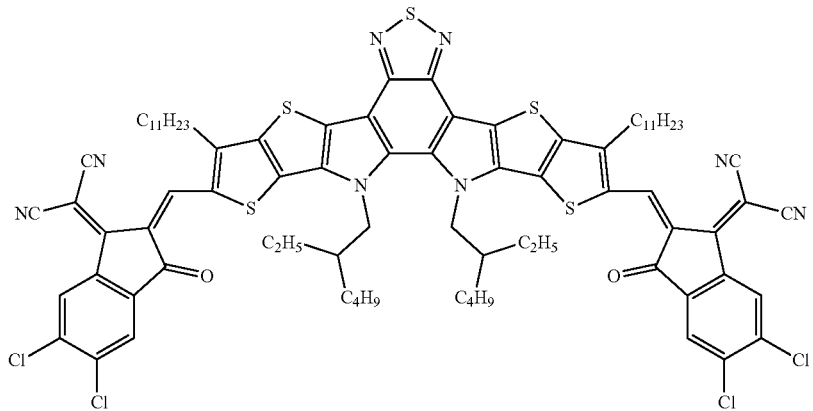
N6
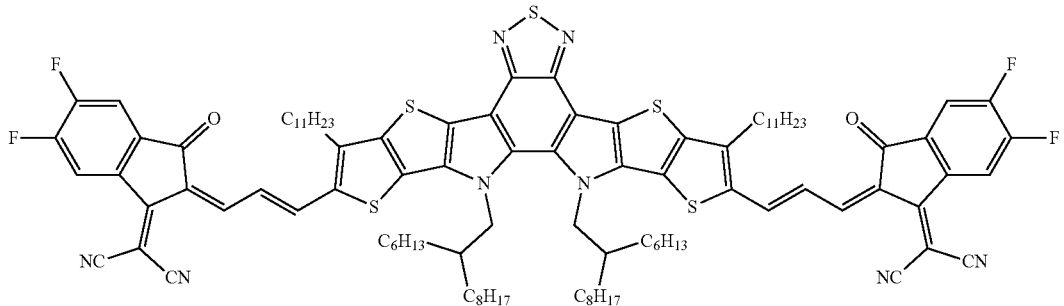
N7
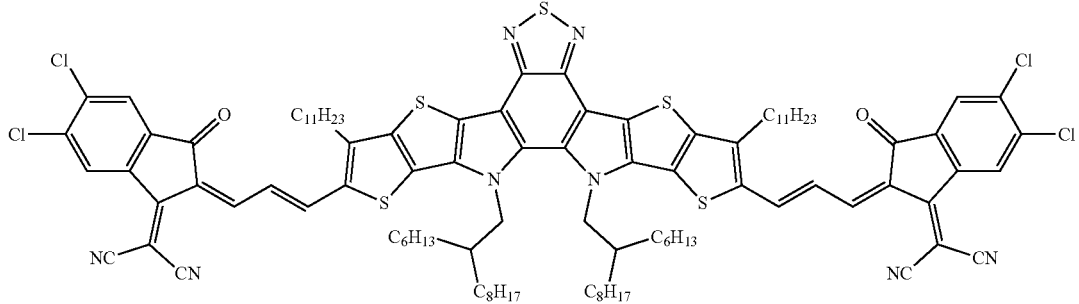
N8

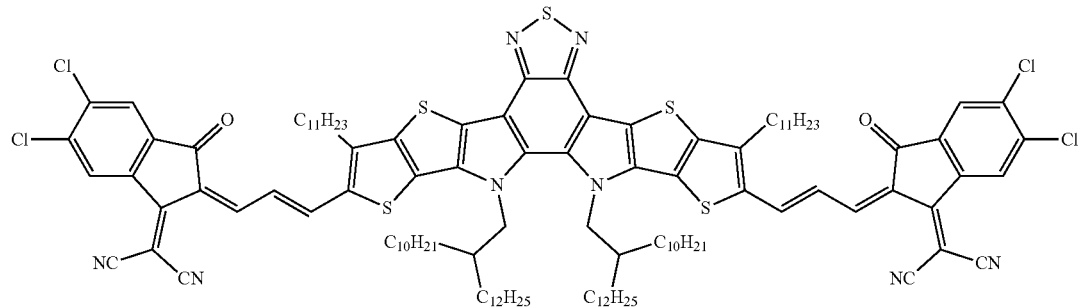
N9
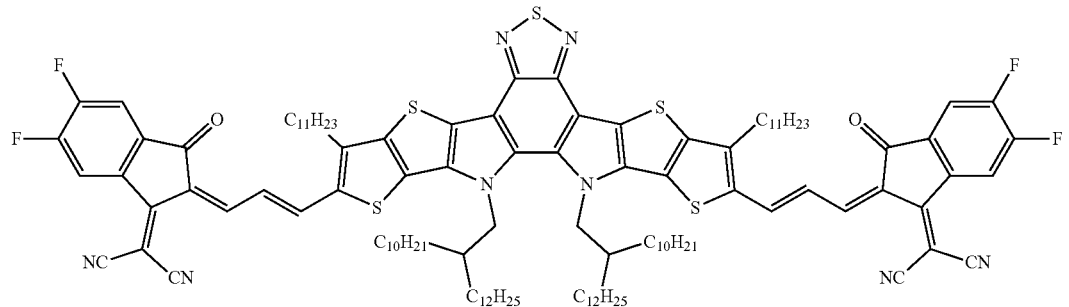
N10
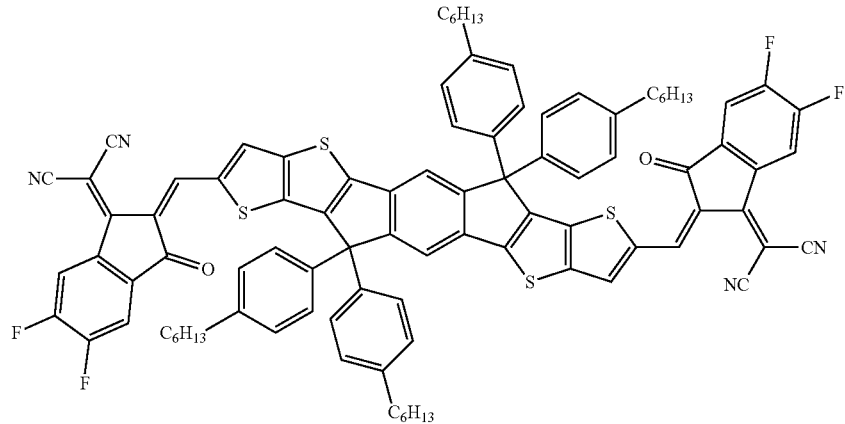
N11
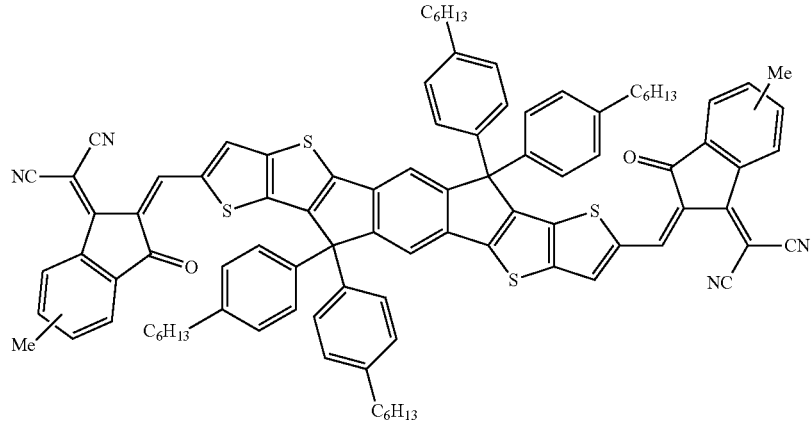
N12

-continued
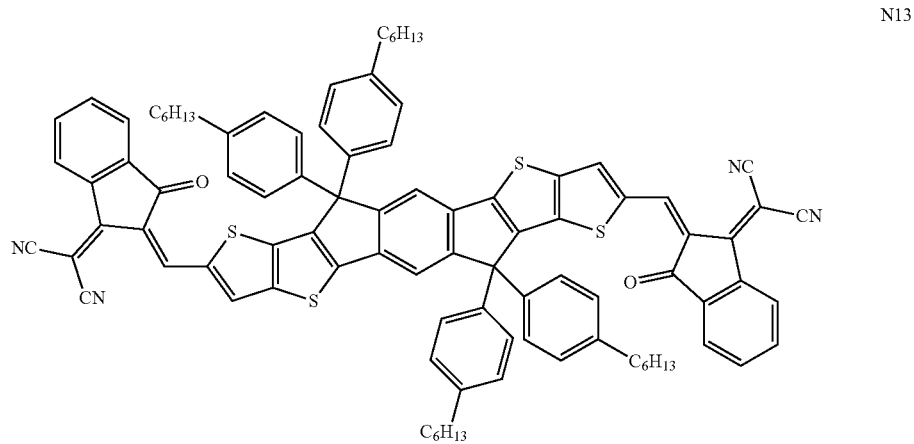
N13
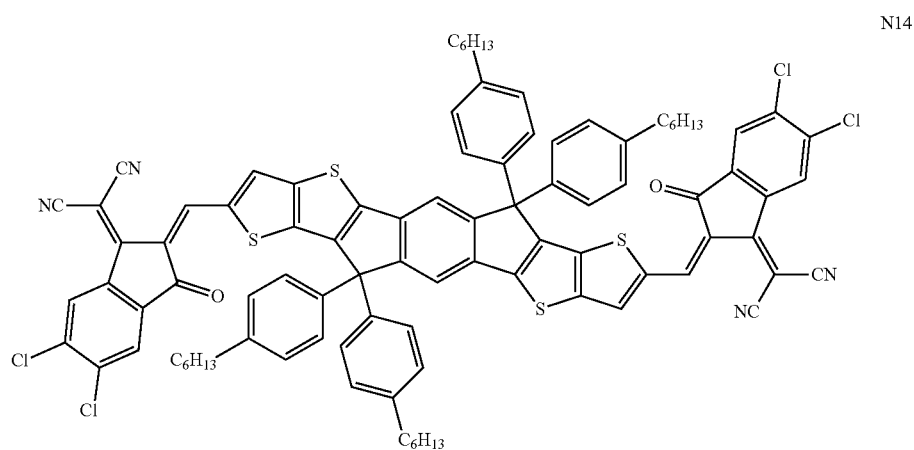
N14
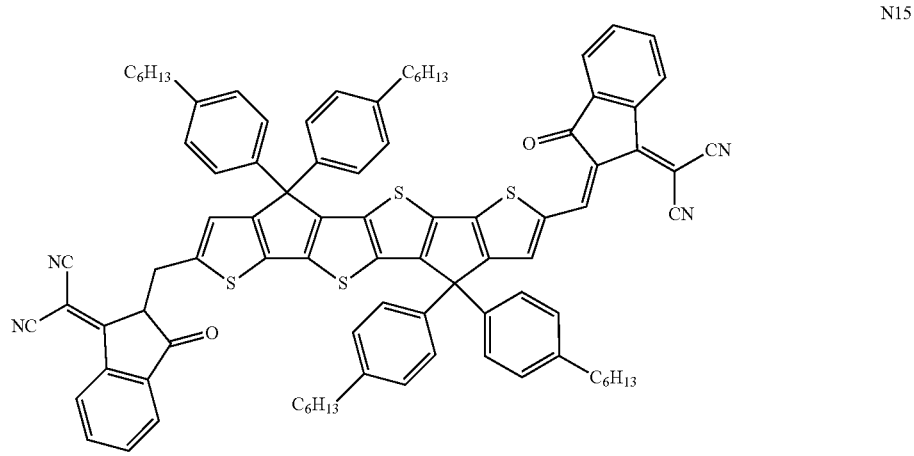
N15

-continued
N16
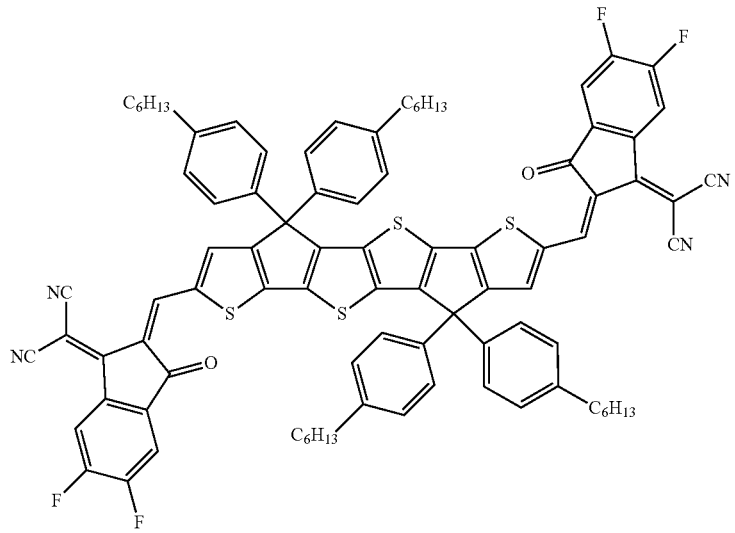
N17
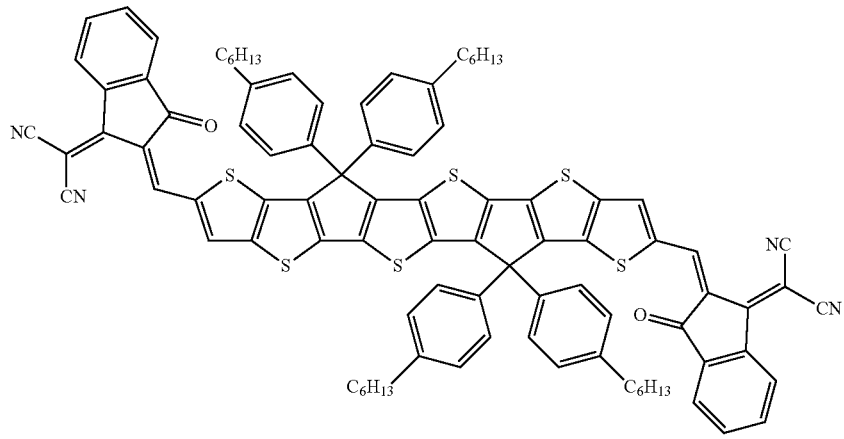
N18
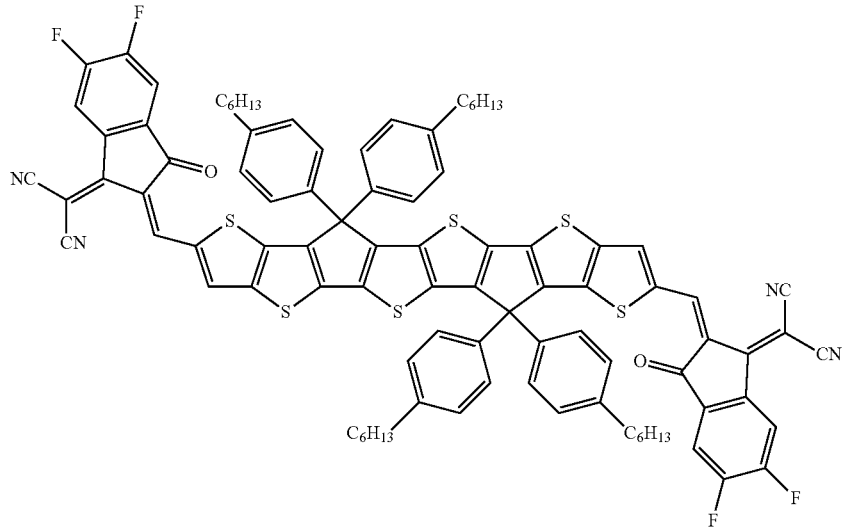

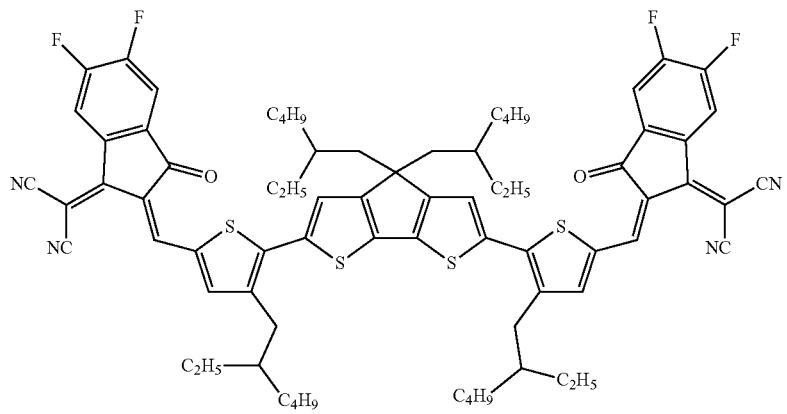
N19
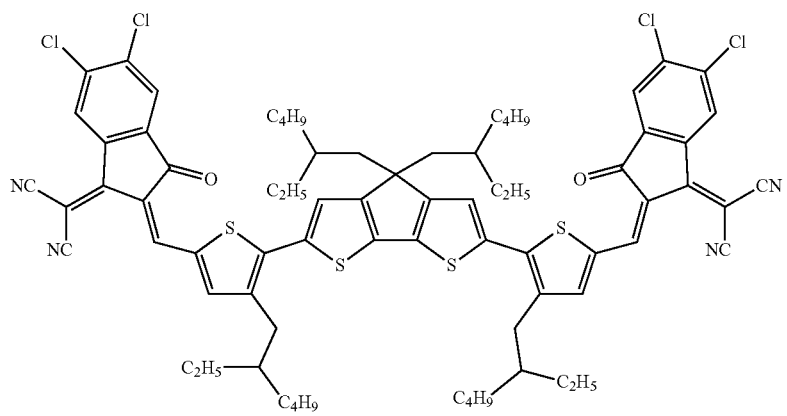
N20
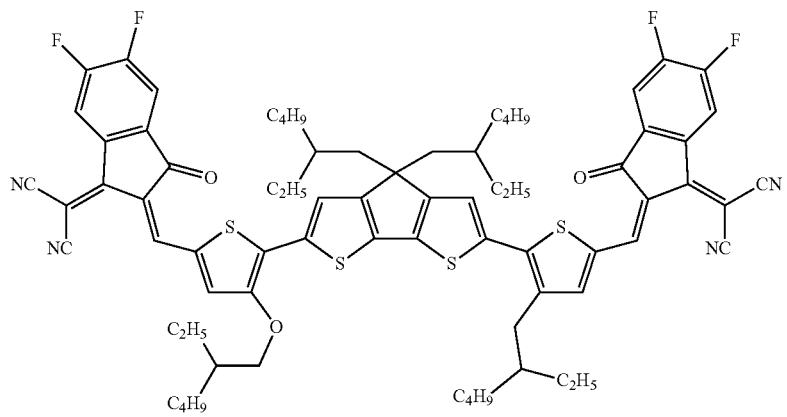
N21
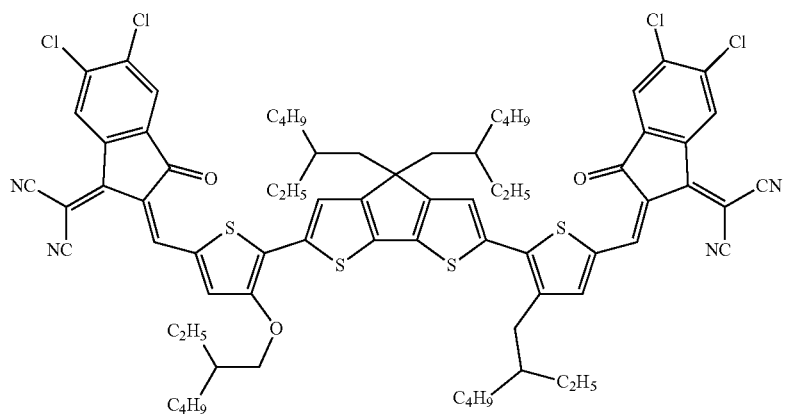
N22

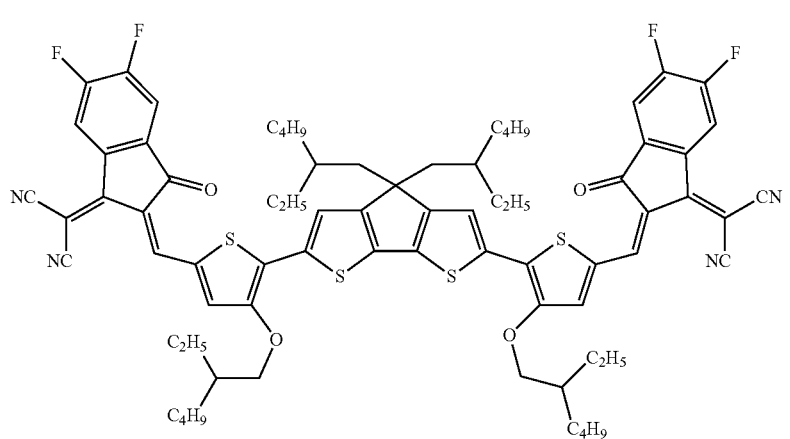
N23
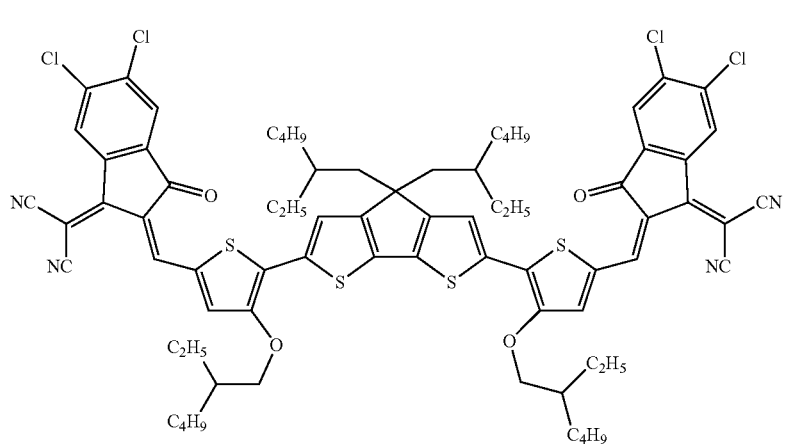
N24
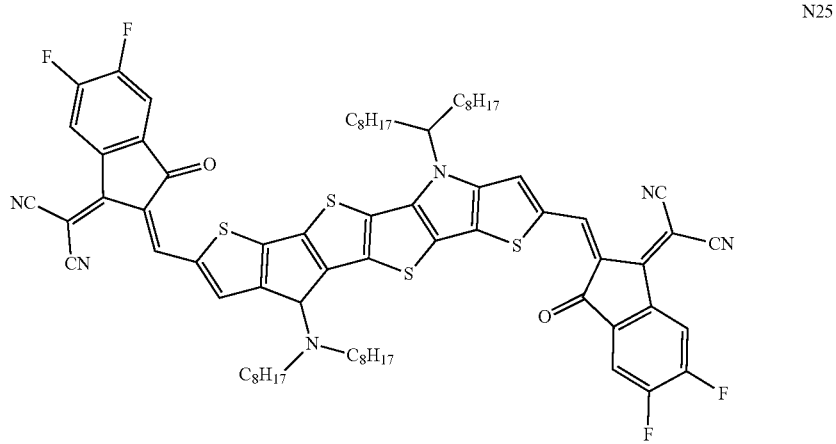
N25

N26
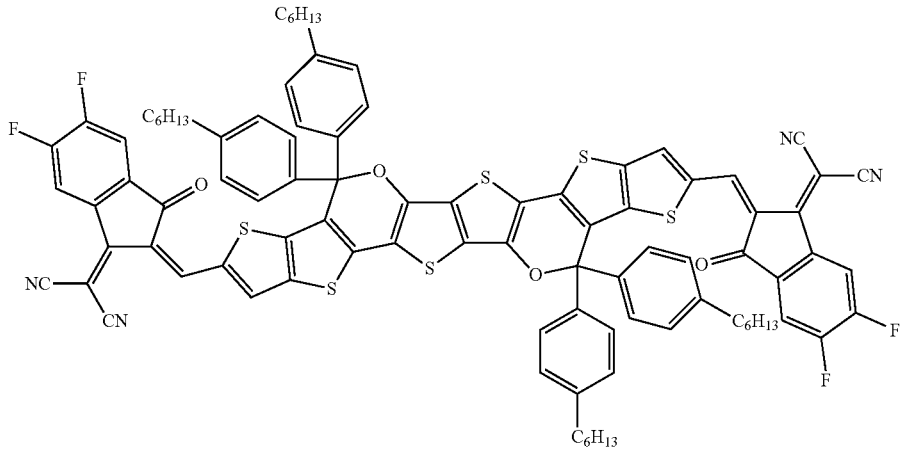
N27
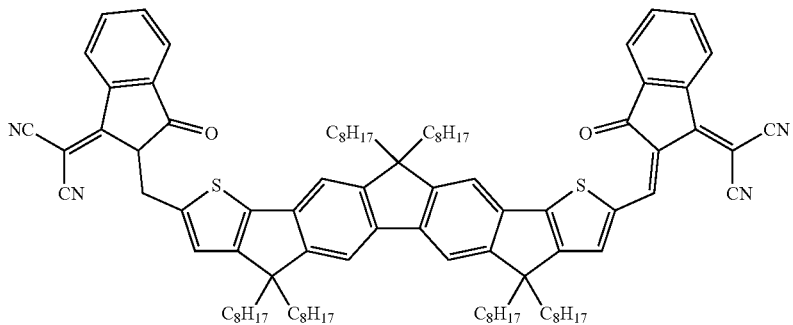
N28
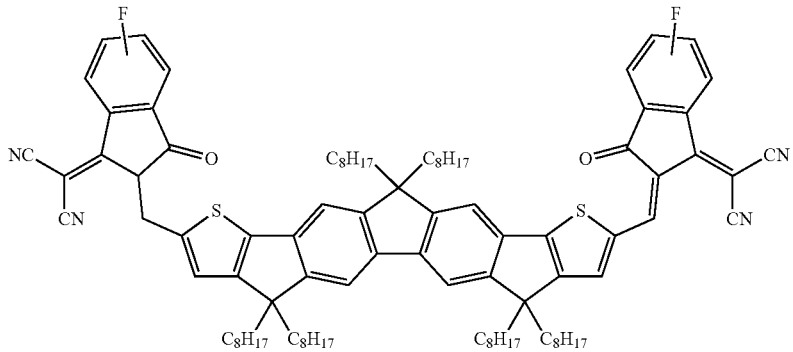
N29
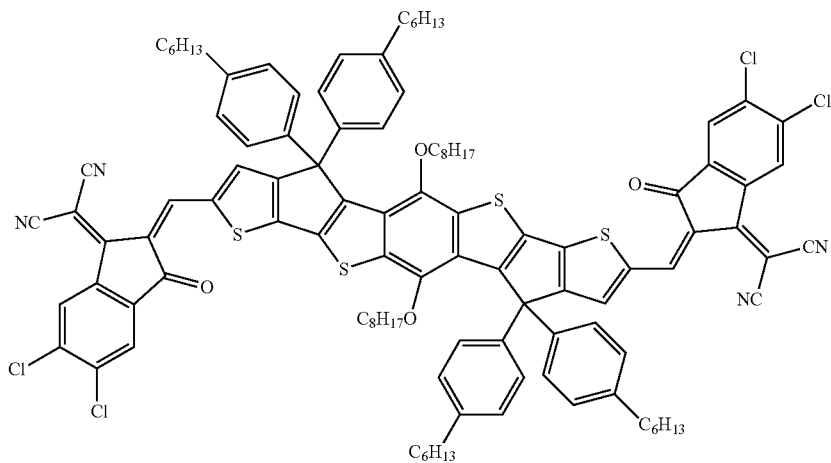

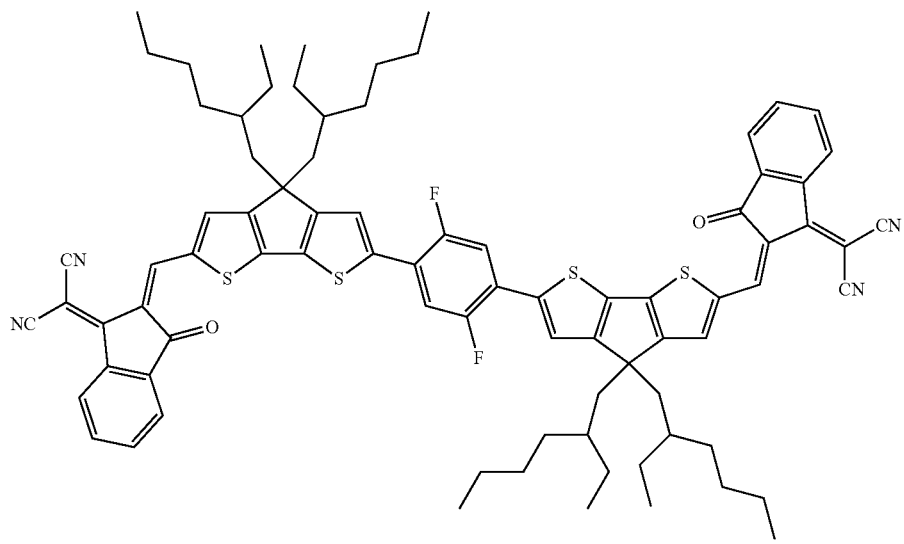
N30
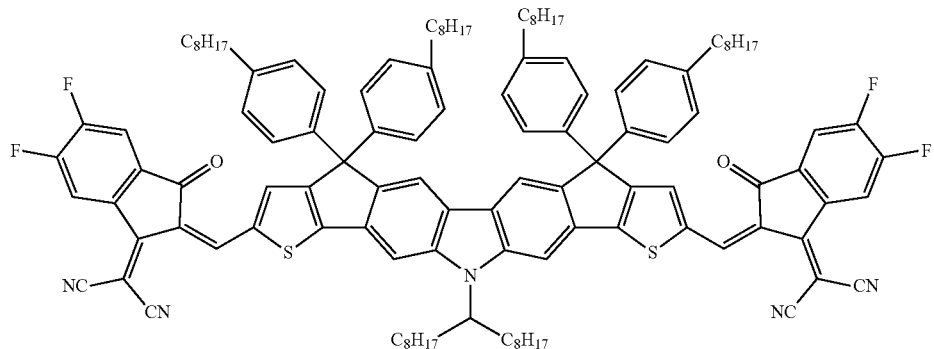
N31
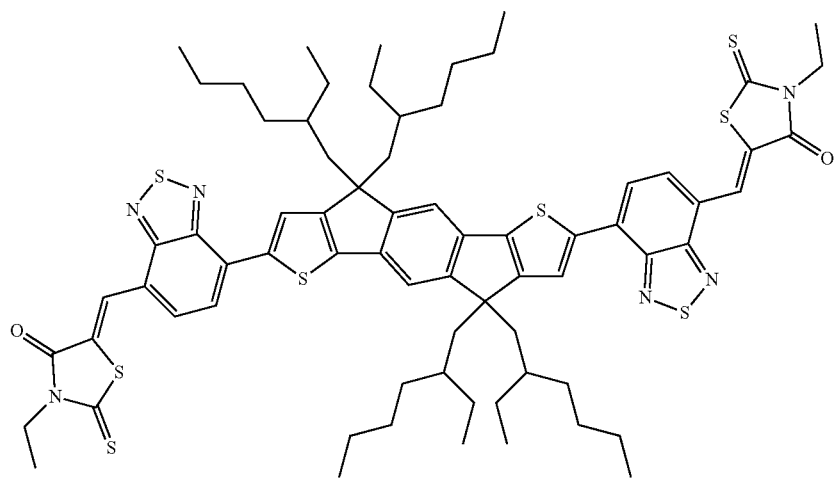
N32

-continued

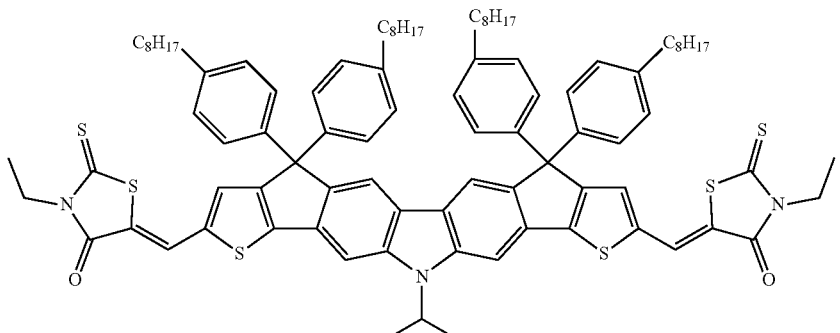
N33

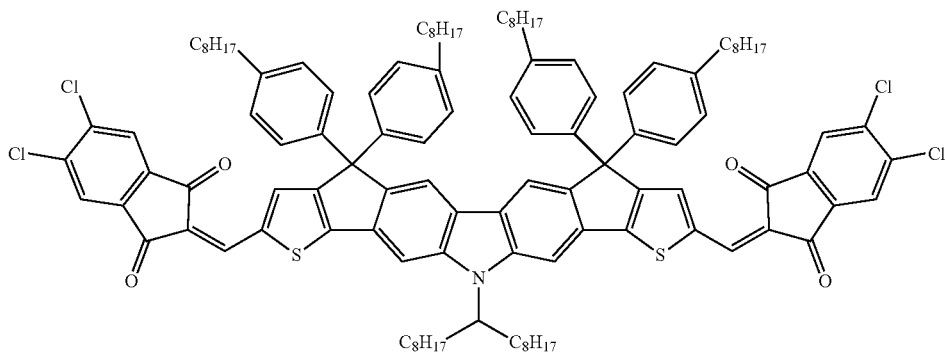
N34

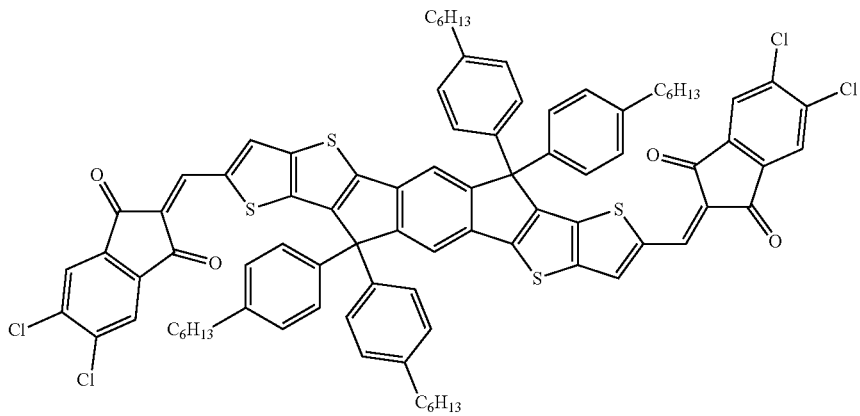
N35

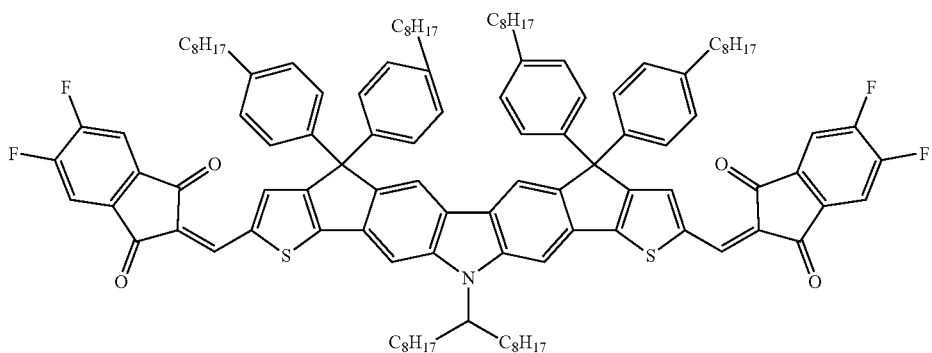
N36

Figure 1C:
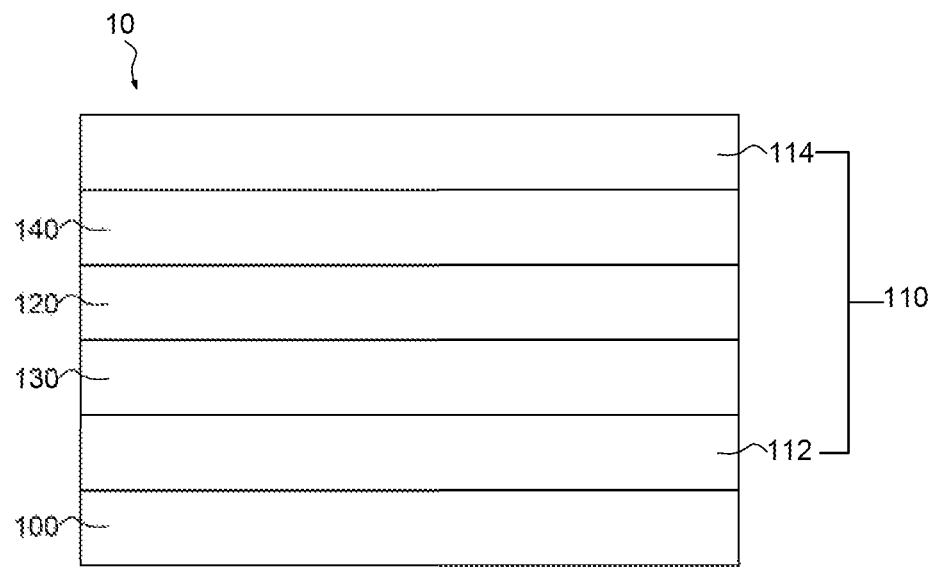

In a further embodiment, please refer to FIG. 1C. The arrangement of the respective components of the organic photoelectric component 10 is the same as those of the first embodiment. The organic photoelectric component 10 further includes a first carrier transporting layer 130 and a second carrier transporting layer 140. The first carrier transporting layer 130 is arranged between the first electrode 112 and the active layer 120 while the second carrier transporting layer 140 is disposed between the second electrode 114 and the active layer 120.

Figure 1D:
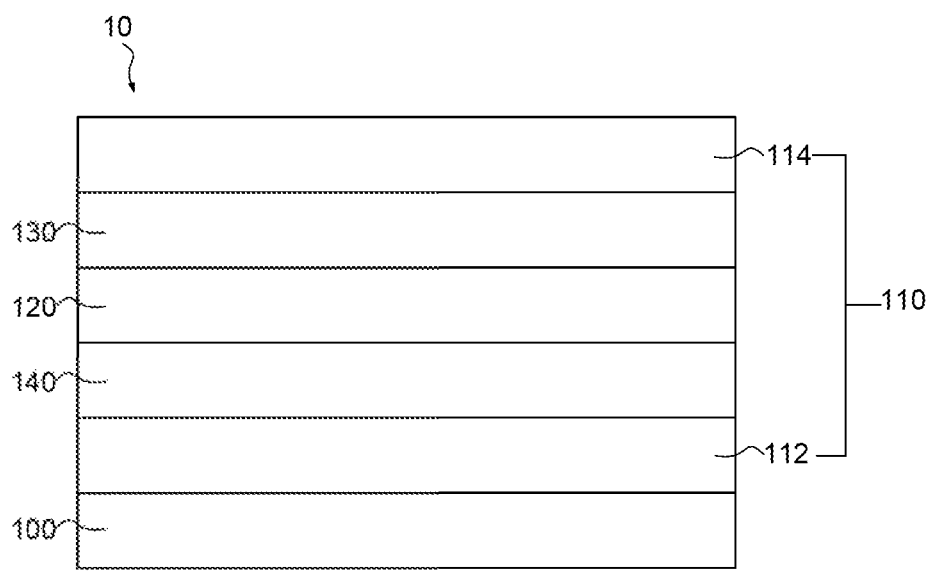

In a fourth embodiment, please refer to FIG. 1D. The respective components of the organic photoelectric component 10 of this embodiment are arranged the same as those of the first embodiment. The organic photoelectric component 10 further includes a first carrier transporting layer 130 arranged between the second electrode 114 and the active layer 120, and a second carrier transporting layer 140 disposed between the first electrode 112 and the active layer 120.

Figure 1E:
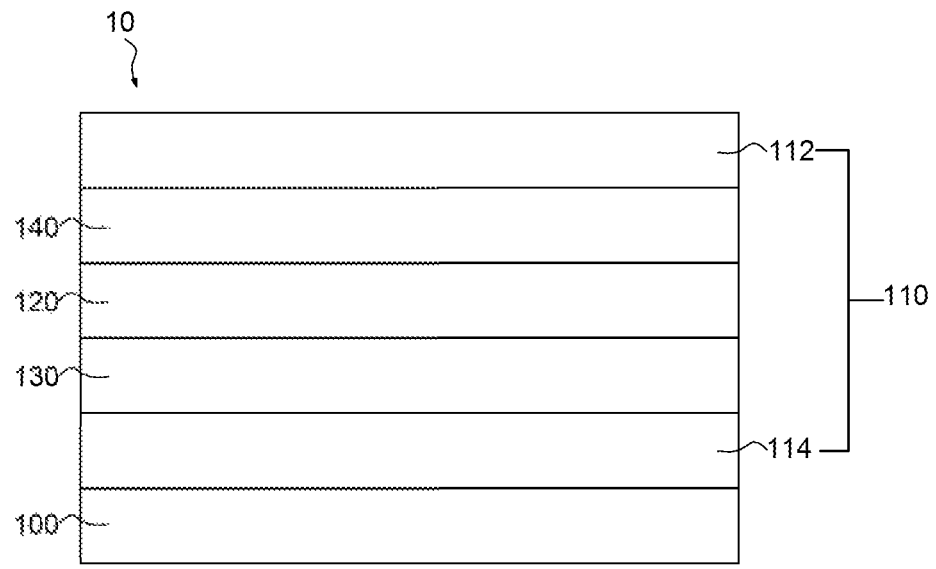

In a fifth embodiment shown in FIG. 1E, the respective components of the organic photoelectric component 10 of this embodiment are arranged the same as those of the second embodiment. The organic photoelectric component 10 further includes a first carrier transporting layer 130 arranged between the second electrode 114 and the active layer 120, and a second carrier transporting layer 140 disposed between the first electrode 112 and the active layer 120.

CsF, and $CsCO_3$, and amines such as primary amines, secondary amines, and tertiary amines.

Figure 2A:
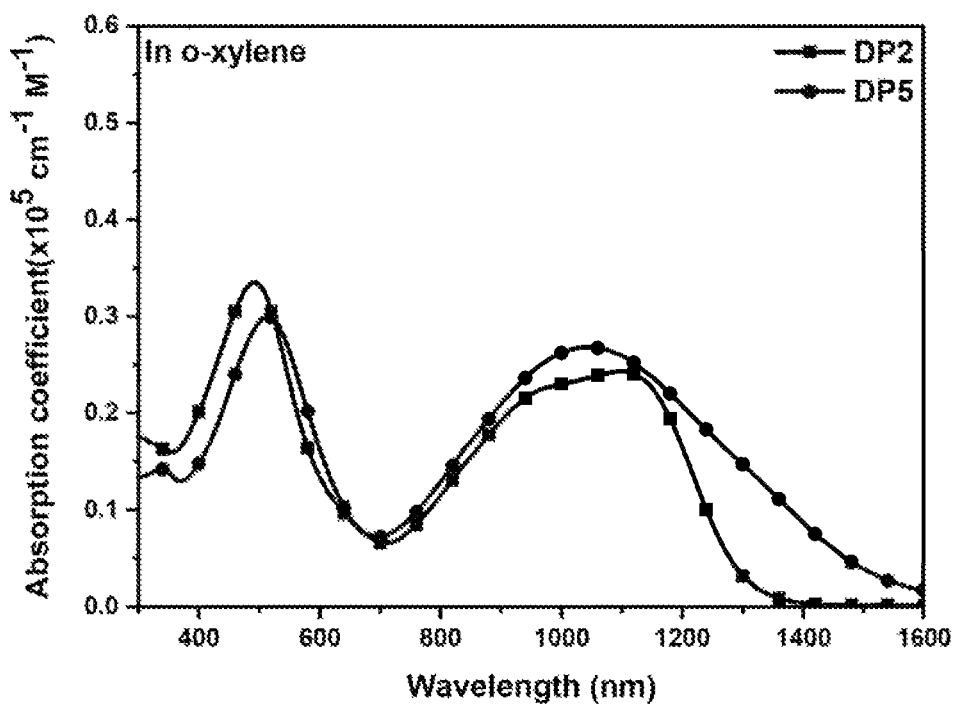
FIG. 2A-2B are light absorption spectra of a solution and a thin-film form of an embodiment of an organic semiconductor compound according to the present invention.
Figure 2B:
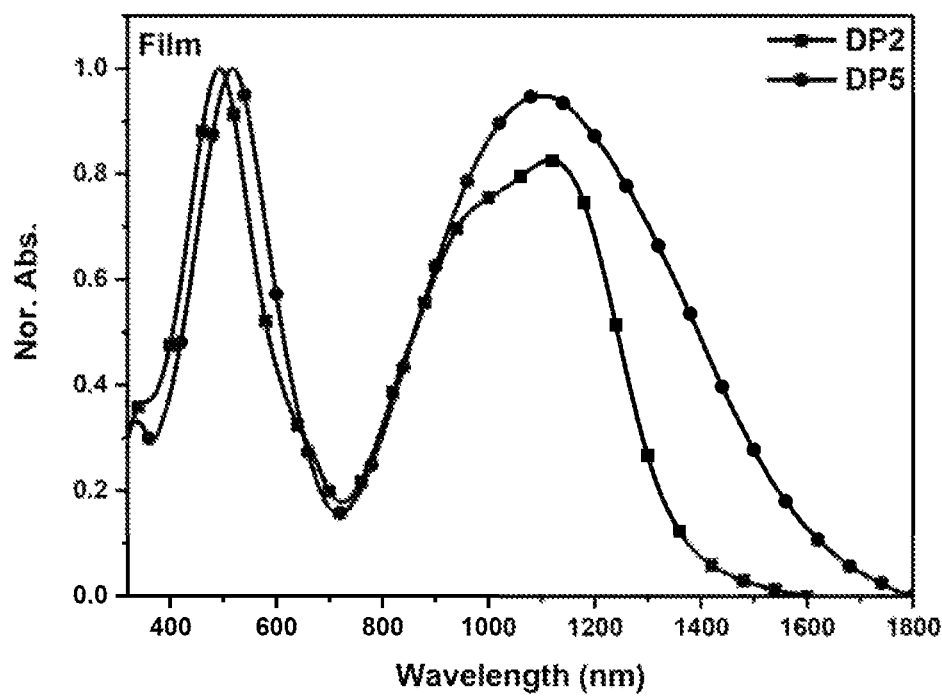
Figure 3A:
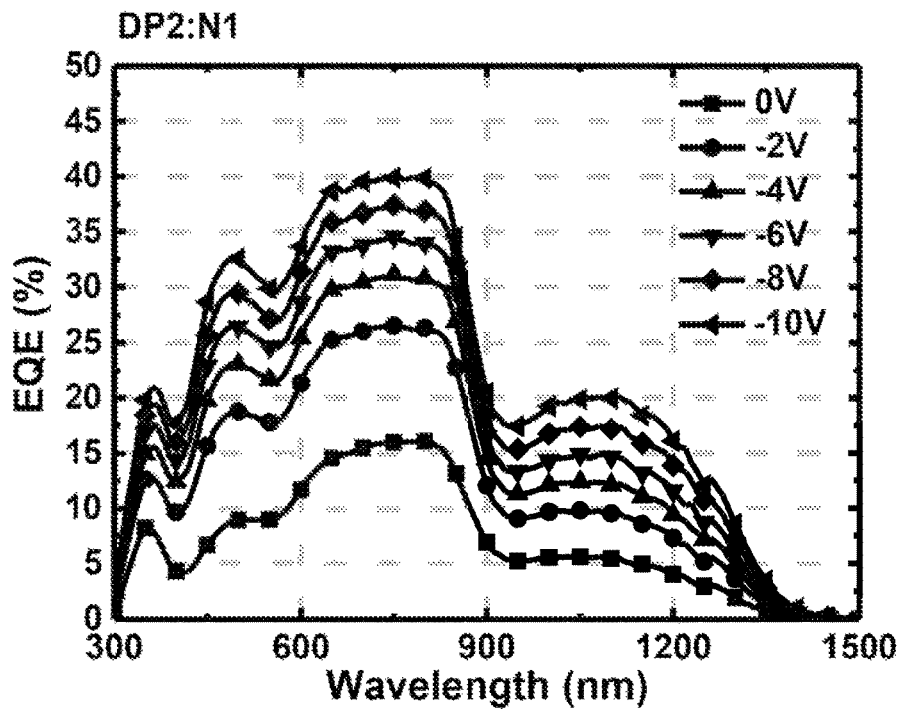
FIG. 3A-3B are experimental results of an embodiment of an organic photoelectric component according to the present invention.
Figure 3B:
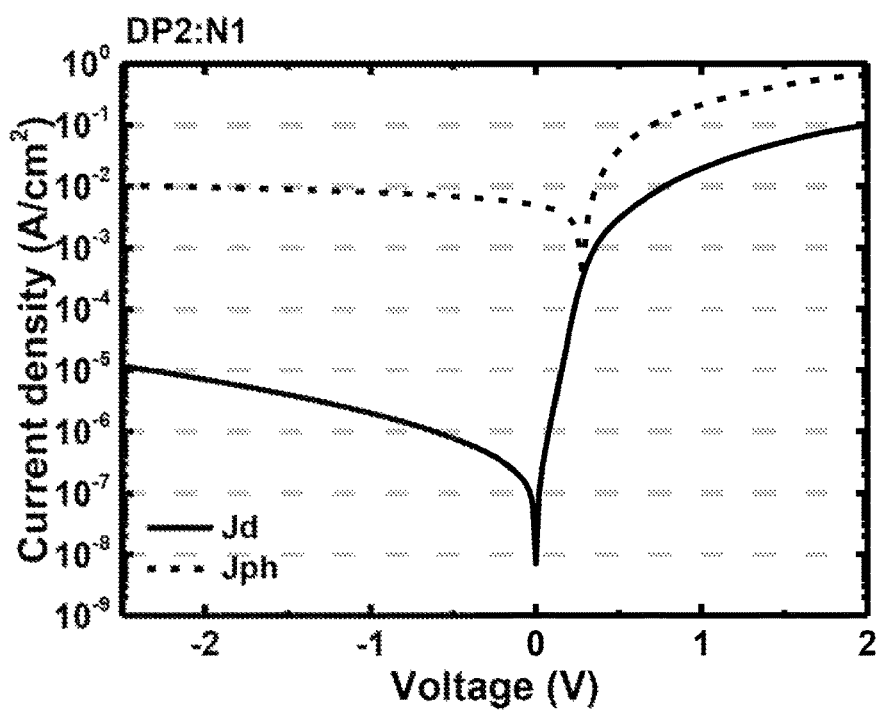
Figure 4A:
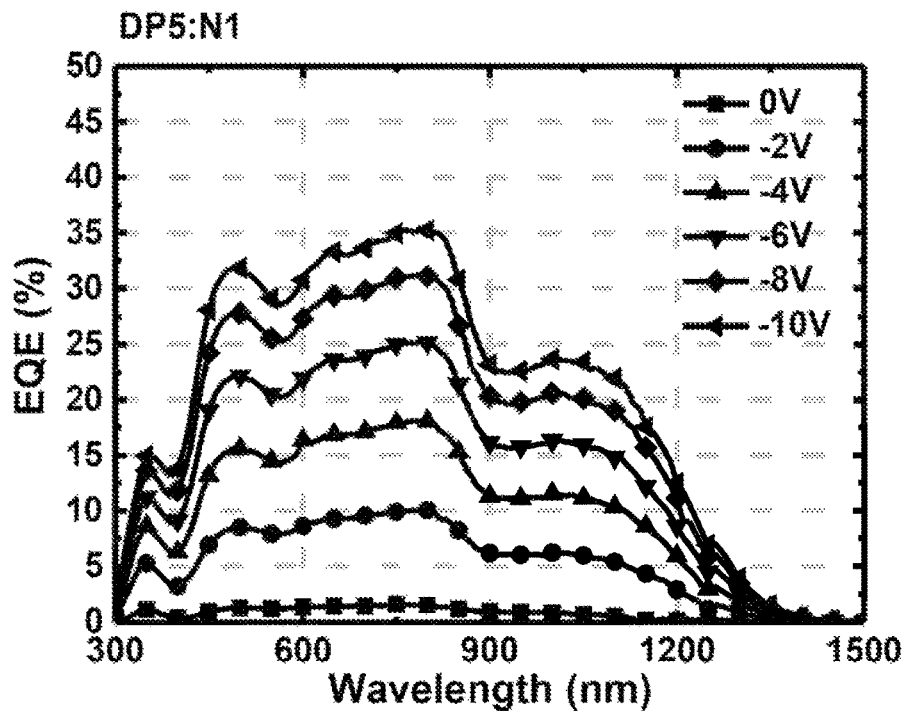
FIG. 4A-4B are experimental results of an embodiment of an organic photoelectric component according to the present invention.
Figure 4B:
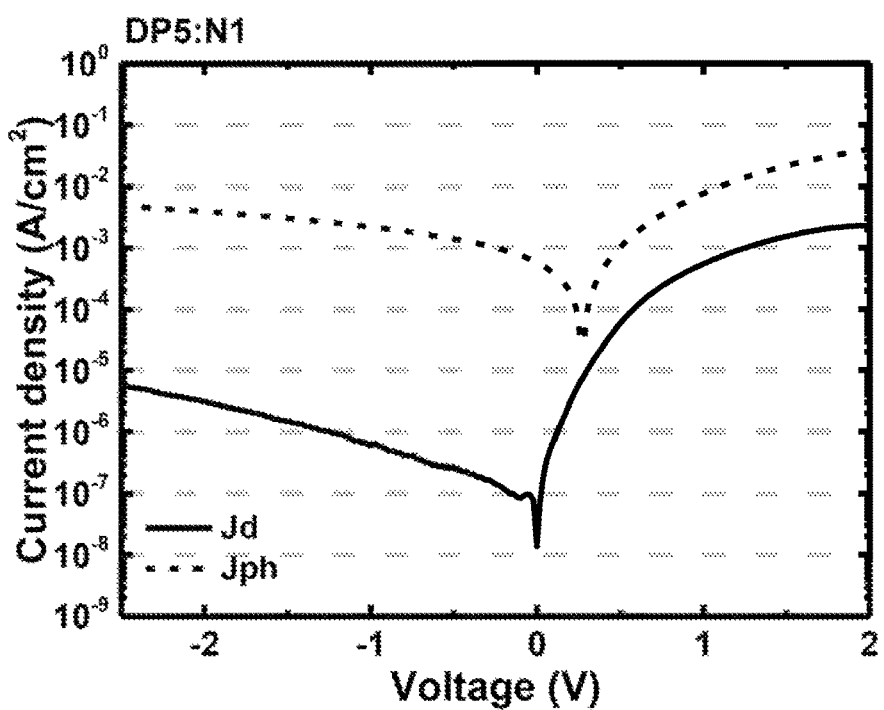

In order to learn performance improvement of the organic photoelectric component resulted from the present organic semiconducting compounds, test properties and performance of the organic photoelectric components containing the present organic semiconducting compounds. The followings are test results Absorption Spectrum of the Respective Materials Use an UV-VIS spectrophotometer to detect absorption spectrum of samples. The sample is dissolved in o-xylene and then the absorption spectrum of solution phase is measured. A thin film sample is prepared by using a sample with a concentration of 10 mg/mL and glass as substrate. The sample is coated on the glass by spin coating to form a thin film. Then measure absorption spectrum of the solid thin film. The absorption spectrum of the respective samples is shown in FIG. 2A and FIG. 2B and the measurement results are shown in Table 2.

TABLE 2 measurement of absorption spectrum and test results of electrochemical properties of the respective samples

| material | $\lambda_{soln}^{max}$ (nm) | $\lambda_{film}^{max}$ (nm) | $\lambda_{film}^{onset}$ (nm) | $\varepsilon$ ($10^5$ $cm^{-1}M^{-1}$) | $E_g^{opt}$ (eV) | HOMO (eV) | LUMO (eV) | solubility |
|---|---|---|---|---|---|---|---|---|
| DP2 | 1108 | 1128 | 1358 | 0.243 | 0.91 | −5.05 | −4.14 | ○ |
| DP5 | 1054 | 1118 | 1619 | 0.268 | 0.77 | −4.68 | −3.91 | ○ |
| PCBOTQ | 532 | 564 | 816 | — | 1.52 | −5.16 | −3.64 | X |
| PTTQ(BO) | — | 1145 | 1426 | — | 0.87 | −4.87 | −4.00 | X |

Figure 1F:
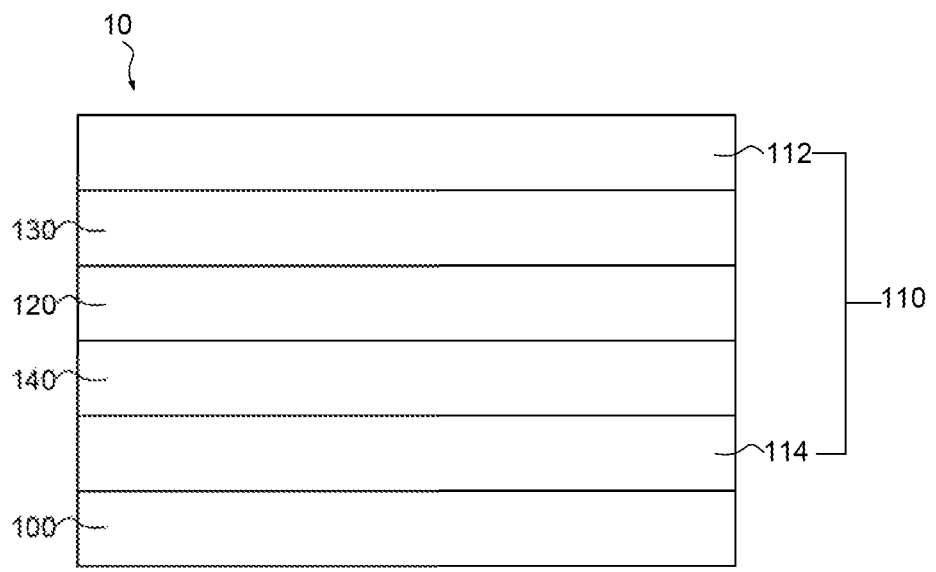

In a sixth embodiment shown in FIG. 1F, the arrangement of the respective components of the organic photoelectric component 10 is the same as those of the second embodiment. The organic photoelectric component 10 further includes a first carrier transporting layer 130 and a second carrier transporting layer 140. The first carrier transporting layer 130 is arranged between the first electrode 112 and the active layer 120 while the second carrier transporting layer 140 is disposed between the second electrode 114 and the active layer 120.

In the third to sixth embodiments mentioned above, the first carrier transporting layer 130 is selected from the followings: conjugated polymer electrolytes such as PEDOT:PSS, polyacids such as polyacrylate, conjugated polymers such as Poly[bis(4-phenyl)(2,4,6-triMethylphenyl)amine] (PTAA), insulating polymer such as Nafion film, Polyethylenimine and Polystyrene sulfonates, polymer doped with metal oxides including MoOx, NiOx, WOx, SnOx, organic small molecule compounds such as N, N'-diphenyl-N, N'-bis-(1-naphthyl) (1,1'-biphenyl)-4,4' diamine (NPB), N, N'-diphenyl-N, N'-(3-aminomethyl phenyl)-1,1'-biphenyl-4,4'-diamine (TPD), or combinations thereof.

In the third to sixth embodiments mentioned above, the second carrier transporting layer 140 is selected from the followings, conjugated polymer electrolytes such as polyethylenimine, conjugated polymer such as poly[3-(6-trimethylammoniumhexyl) thiophene], poly[9,9-bis(2-ethylhexyl)fluorene]-h-poly[3-(6-trimethylammoniumhexyl) thiophene], or poly[(9,9-bis(3'-(N,N-dimethylamino)propyl)-2, 7-fluorene)-alt-2,7-(9,9-dioctylfluorene)], organic small molecule compound such as Tris(8-hydroxyquinoline) aluminum(III) ($Alq_3$), 4,7-diphenyl-1,10-phenanthroline, metal oxides such as ZnOx, aluminum-doped zinc oxide (AZO), TiOx and their nanoparticles, salts such as LiF, NaF, PCBOTQ of the comparison sample 1 is from J. Phys. Chem. C 2012, 116, 8379-8386 while PTTQ(BO) of the comparison sample 2 is from J. Mater. Chem. C, 2020, 8, 10098-10103. In this embodiment, DP2 and DP5 are dissolved in environmentally friendly o-xylene and the processed while halogenated solvents are used for processing of PCBOTQ and PTTQ(BO). Compared with solvents containing halogens used in conventional techniques, the organic semiconductors of the present invention have less impact on the environment during processing. In absorption range of the test material in the thin-film form, polymers designed by the present invention have red-shifted to over 1100 nm. Moreover, an absorption onset value of the thin-film is in the region over 1350 nm while that of the comparison sample PCBOTQ is only 816 nm, which is much smaller than the absorption range of the present invention. As shown in FIG. 2A and FIG. 2B, the polymers designed by the present invention used in OPDs have external quantum efficiency (EQE) response at the wavelength of 1350 nm or in the wavelength range longer than 1350 nm.

Electrochemical Properties of Materials

Redox potentials of the compounds according to the present invention are recorded by an electrochemical analyzer. 0.1 M tetra-1-butylammonium hexafluorophosphate ($Bu_4NPF_6$) in acetonitrile solution is used as electrolyte while 0.01 M silver nitrate ($AgNO_3$) and 0.1 M TBAP (tetrabutylammonium perchlorate) in acetonitrile solution with silver/silver chloride electrode is used as a reference electrode. Platinum (Pt) is a counter electrode and glass carbon electrode is used as a working electrode. The sample is dissolved in o-xylene and then dropped on the working electrode to form a thin film for measurement. The thin film is scanned at the speed of 50 mV/sec to obtain a cyclic voltammetry (CV) curve. CV curve of ferrocene/ferrocenium (Fc/Fc') is used for internal calibration and then HOMO and LUMO energy level of the sample tested are obtained and calculated by the following equation:

$$HOMO = -|4.71 + E_{ox} - E^{ferroncene}|$$

$$LUMO = HOMO + E_g^{opt}$$

Test results of the respective samples are shown in table 2.

In an embodiment, oxidation of DP2 and DP5 is measured by cyclic voltammetry (CV). The Highest Occupied Molecular Orbital (HOMO) can be learned after calculation ($HOMO = -|4.71 + E^{ox} - E^{ferroncene}|$). Then optical energy gap ($E_g = 1241/\lambda_{onset}$) and Lowest Unoccupied Molecular Orbital (LUMO) (LUMO HOMO+$E_g^{opt}$)) of the material are learned according to absorption onset ($\lambda_{onset}$) of ultraviolet-visible-near infrared (UV-Vis-NIR) absorption spectrum of the material in thin-film form.

Organic Photodetector (OPD) Performance Test

Use glass with sheet resistance and patterned ITO coating as a substrate and treat by ultrasonic vibration in neutral detergent, deionized water, acetone, and isopropanol in turn. The substrate is washed for 15 minutes in each step. The washed substrate is further cleaned by UV-$O_3$ treatment for 15 minutes. Then coat AZO on the ITO substrate by spin coating at speed of 2000 rpm and duration of 40 seconds to form a top coating layer. Bake in the air at 120° C. for 5 minutes. Next prepare an active layer solution (weight ratio of donor polymer to small molecule acceptor=1:1) in o-xylene with a total concentration of 20 mg/mL. In order to dissolve the polymer completely, the active layer solution is stirred on a heating plate at 100° C. for at least 3 hours. Then filter the solution with PTFE (polyfluortetraethylene) membrane filter (pore size 0.45~1.0 μm) and heat the active layer solution again for 1 hour. Place the solution at room temperature and cool down. Next perform coating and control a thickness of the film to be about 100 nm by spin coating speed. Then the composite film is annealed at 100° C. for 5 minutes and placed into an evaporator. Perform vacuum deposition under 3×10$^{-6}$ Torr, deposit a molybdenum trioxide thin film (8 nm) used as the hole transport layer and silver thin film (100 nm) as an outer electrode. Use Keithley™ 2400 source meter to record dark current density ($J_d$, bias of −8 V) under no light. Then measure photocurrent density ($J_{ph}$) of the components in the air at room temperature using a solar simulator. (100 mW cm$^2$ xenon lamp with AM1.5G filter). Standard LED with KG5 filter is used as reference cell for calibration of light intensity to make spectral mismatch become uniform. In order to measure EQE, an external quantum efficiency measurement system with range of 300~1800 nm (bias 0~−10 V) and calibration of the light source is done using silicon (300~1100 nm) and germanium (1100~1800 nm).

An active layer formulation of the DP2 component is DP2:N1=1:1 with total concentration of 20 mg/mL prepared in o-xylene while an active layer formulation of the DP5 component is DP5:N1=1:1 with total concentration of 20 mg/mL prepared in o-xylene. The structure of the above organic photoelectric component is glass/ITO/AZO/ATL/MoO3/Ag.

The current density of the respective samples according to the present invention is shown in FIG. 3A, FIG. 3B, FIG. 4A, and FIG. 4B and the test results are shown in table 3 and table 4.

TABLE 3

Electrical tests of organic photoelectric components containing the present organic semiconducting compounds

| | | | | | | |
|---|---|---|---|---|---|---|
| Wavelength (nm) | 1100 | 1100 | 1100 | 1100 | 1100 | 1100 |
| Active layer | PCBOTQ: PC$_{71}$BM | PTTQ(BO): PC$_{71}$BM | PTZBTTT-BDT: PC$_{61}$BM | P4: PC$_{61}$BM | DP2: N1 | DP5: N1 |
| Thickness (nm) | 80-90 | 300 | ~70 | 385 | 100 | 100 |
| Band gap(eV) | 1.52 | 0.86 | 1.10 | 0.85 | 0.91 | 0.77 |
| Structure | Conventional | Inverted | Conventional | Inverted | Inverted | Inverted |
| ETL | LiF | ZnO | PFN | PEIE | AZO | AZO |
| HTL | PEDOT | MoO$_3$ | PEDOT: PSS | MoO$_3$ | MoO$_3$ | MoO$_3$ |
| Solvents for process | CB | CB | o-DCB | CB, CF, DIO | o-xylene | o-xylene |
| $J_d$ (A/cm$^2$) | — | 10$^{-4}$ @ −2 V | 10$^{-6}$ @ −2 V | 10$^{-5}$ @ −1.5 V | 10$^{-6}$ @ −2 V | 10$^{-6}$ @ −2 V |
| EQE | No response | ~17%@ −2 V | No response | ~7% @ 0 V | 20.0% @ −10 V | 21.5% @ −10 V |
| Ref. | J. Phys. Chem. C 2012, 116, 8379-8386. | J. Mater. Chem. C, 2020, 8, 10098-10103 | J. Phys. Chem. C 2013, 117, 6537-6543 | Polym. Chem., 2017, 8, 2922-2930 | This work | This work |

In this embodiment, the polymer in combination with non-fullerene small molecules is used as an active layer and test results in previous work are shown in table 3. An organic photoelectric component prepared by the active layer of DP2:N1 at 1100 nm is with EQE response of 20.0% and dark current density of 10$^{-6}$/cm$^2$ while an organic photoelectric component prepared by the active layer of DP5:N1 is with EQE response of 21.5% and dark current density of 10$^{-6}$ A/cm$^2$. Compared with the techniques available now, the organic photoelectric component with DP2:N1 and DP5:N1 according to the present invention has excellent performance on the EQE response and the dark current density. Moreover, the polymers of the present invention are more soluble in non-halogen solvents compared with materials available now. Thus, the non-halogen solvents (environmentally friendly solvent) can be used for coating process. No additive is added, and this is beneficial to stability of the components as expected.

TABLE 4

Electrical tests of organic photoelectric components containing the present organic semiconducting compounds

| Wavelength (nm) | 700 | 700 | 700 | 700 | 700 | 700 |
|---|---|---|---|---|---|---|
| Active layer | PCBOTQ: PC$_{71}$BM | PTTQ(BO): PC$_{71}$BM | PTZBTTT-BDT: PC$_{61}$BM | P4: PC6BM | DP2: N1 | DP5: N1 |
| Thickness (nm) | 80-90 | 300 | ~70 | 385 | 100 | 100 |
| Band gap(eV) | 1.52 | 0.86 | 1.10 | 0.85 | 0.91 | 0.77 |
| Structure | Conventional | Inverted | Conventional | Inverted | Inverted | Inverted |
| ETL | LiF | ZnO | PFN | PEIE | AZO | AZO |
| HTL | PEDOT | MoO$_3$ | PEDOT:PSS | MoO$_3$ | MoO$_3$ | MoO$_3$ |
| Solvents for process | CB | CB | o-DCB | CB, CF, DIO | o-xylene | o-xylene |
| J$_d$ (A/cm$^2$) | — | 10$^{-4}$ @ −2 V | 10$^{-6}$ @ −2V | 10$^{-5}$ @ −1.5 V | 10$^{-6}$ @ −2 V | 10$^{-6}$ @ −2 V |
| EQE | ~16% @ 0 V | ~7% @ −2 V | ~17% @ 0 V | ~9% @ 0 V | 39.5% @ −10 V | 33.6% @ −10 V |
| Ref. | J. Phys. Chem. C 2012, 116, 8379-8386. | J. Mater. Chem. C, 2020, 8, 10098-10103 | J. Phys. Chem. C 2013, 117, 6537-6543 | Polym. Chem., 2017, 8, 2922-2930 | This work | This work |

In this embodiment, the polymer in combination with non-fullerene small molecules is used as an active layer and test results in previous work are shown in table 4. An organic photoelectric component prepared by the active layer of DP2:N1 at 700 nm is with EQE response of 39.9% and dark current density of 10$^{-6}$ A/cm$^2$ while an organic photoelectric component prepared by the active layer of DP5:N1 is with EQE response of 35.0% and dark current density of 10$^{-6}$ A/cm$^2$. Compared with the techniques available now, the organic photoelectric component according to the present invention has excellent performance on the EQE response and the dark current density. Especially among visible light area and near-infrared area, good response provided satisfies requirements for visible light detector and near infrared photodetector. At the same time, the problem occurs in the technique mentioned in J. Mater. Chem. C, 2020, 8, 10098-10103 that there is an obvious gap at 700 nm and this the wavelength nearby is unable to be detected. Therefore, the organic semiconductor materials and organic photoelectric components manufactured by the same have better performance than the conventional techniques.

What is claimed is:

1. An organic compound of the following formula:

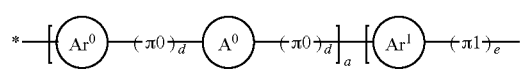

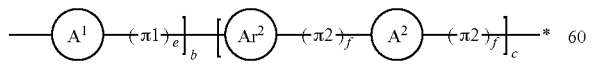

wherein

A$^0$ is an electron withdrawing group;

A$^1$ is electron withdrawing group which is different from A$^0$ and is selected from the following formulae;

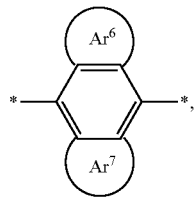

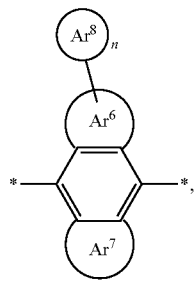

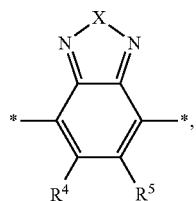

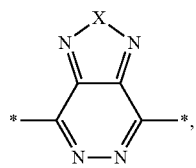
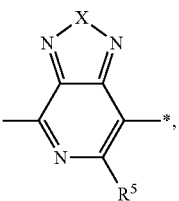

-continued

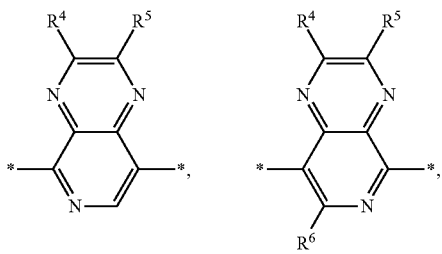

R⁴-R⁶ are selected from the group consisting of the following groups:

halogen, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, C3-C30 keto-substituted alkyl, unsubstituted aromatic group, unsubstituted heterocyclic group, unsubstituted fused ring group, unsubstituted fused heterocyclic group, aromatic group substituted with at least one $R^a$, heterocyclic group substituted with at least one $R^a$, fused ring group substituted with at least one $R^a$, and fused heterocyclic group substituted with at least one $R^a$;

X is selected from the group consisting of O, S, or Se;

$Ar^6$ and $A^7$ are selected from the group consisting of unsubstituted aromatic group, unsubstituted heterocyclic group, unsubstituted fused ring group, unsubstituted fused heterocyclic group, aromatic group substituted with at least one $R^a$, heterocyclic group substituted with at least one $R^a$, fused ring group substituted with at least one $R^a$, and fused heterocyclic group substituted with at least one $R^a$;

$Ar^8$ is selected from the group consisting of hydrogen atom, halogen, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, C3-C30 keto-substituted alkyl, unsubstituted aromatic group, unsubstituted heterocyclic group, unsubstituted fused ring group, unsubstituted fused heterocyclic group, aromatic group substituted with at least one $R^b$, heterocyclic group substituted with at least one $R^b$, fused ring group substituted with at least one $R^b$, and fused heterocyclic group substituted with at least one $R^b$;

$R^a$ and $R^b$ are selected from the group consisting of hydrogen atom, halogen, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl; and h is an integer selected from 1 to 8;

$A^2$ is selected from the group consisting of

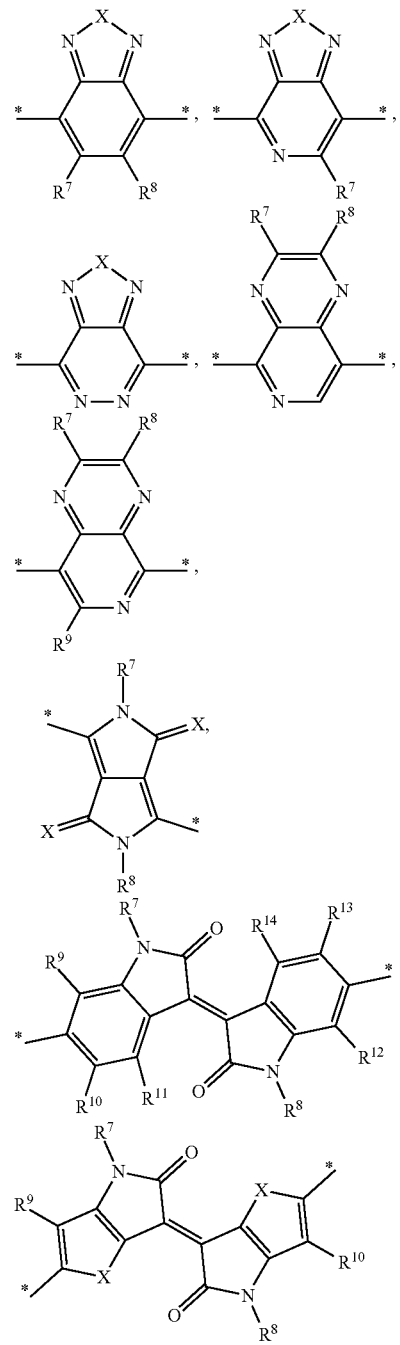

wherein $R^7$-$R^8$ are selected from the group consisting of halogen, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, C3-C30 keto-substituted alkyl, unsubstituted aromatic group, unsubstituted heterocyclic group, unsubstituted fused ring group, unsubstituted fused heterocyclic group, aromatic group substituted with at least one $R^b$, heterocyclic group substituted with at least one $R^b$, fused ring group substituted with at least one R$^b$, and fused heterocyclic group substituted with at least one R$^b$;

R$^9$-R$^{14}$ are selected from the group consisting of hydrogen atom, halogen, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, C3-C30 keto-substituted alkyl, unsubstituted aromatic group, unsubstituted heterocyclic group, unsubstituted fused ring group, unsubstituted fused heterocyclic group, aromatic group substituted with at least one R$^b$, heterocyclic group substituted with at least one R$^b$, fused ring group substituted with at least one R$^b$, and fused heterocyclic group substituted with at least one R$^b$;

wherein R$^b$ is selected from the group consisting of hydrogen atom, halogen, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituent alkyl, C1-C30 nitro-substituent alkyl, C1-C30 hydroxy-substituent alkyl, and C3-C30 keto-substituent alkyl; and X is selected from O, S, or Se, Ar$^0$, A$^1$, Ar$^2$, π0, π1, and π2 are electron donating groups which are independent from one another;

d, e, f are integers independent from one another and selected from 0 to 5; and a, b, c are real numbers, wherein a+b+c=1, 0<a≤1, 0<b≤1 and 0<c≤1.

2. The organic compound according to claim 1, wherein Ar$^0$, Ar$^1$, Ar$^2$, π0, π1 and π2 are selected from the group consisting of

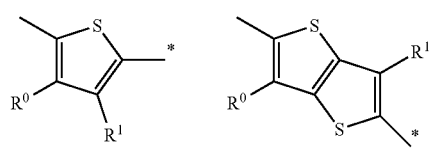

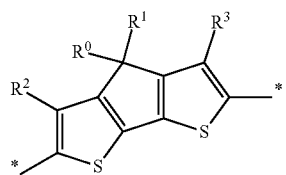

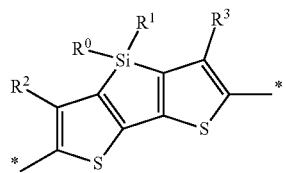

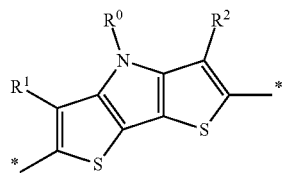

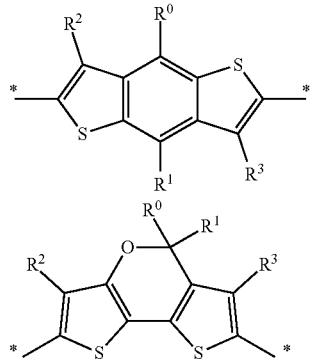

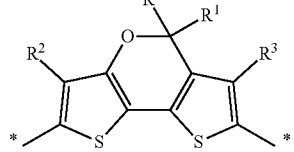

wherein R$^0$-R$^3$ are selected from the group consisting of hydrogen atom, halogens, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, C3-C30 keto-substituted alkyl, unsubstituted aromatic group, unsubstituted heterocyclic group, unsubstituted fused ring group, unsubstituted fused heterocyclic group, aromatic group substituted with at least one R$^a$, heterocyclic group substituted with at least one R$^a$, fused ring group substituted with at least one R$^a$, and fused heterocyclic group substituted with at least one R$^a$; and wherein R$^a$ is selected from the group consisting of hydrogen atom, halogen, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl.

3. The organic compound according to claim 1, wherein A$^0$ is selected from the group consisting of

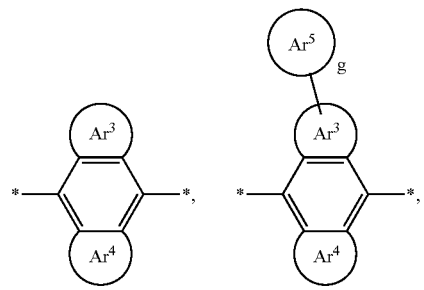

wherein Ar$^3$ and Ar$^4$ are selected from the group consisting of unsubstituted aromatic group, unsubstituted heterocyclic group, unsubstituted fused ring group, unsubstituted fused heterocyclic group, aromatic group substituted with at least one R$^a$, heterocyclic group substituted with at least one R$^a$, fused ring group substituted with at least one R$^a$, and fused heterocyclic group substituted with at least one R$^a$;

Ar$^5$ is selected from the group consisting of the following groups: hydrogen atom, halogen, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, C3-C30 keto-substituted alkyl, unsubstituted aromatic group, unsubstituted heterocyclic group, unsubstituted fused ring group, unsubstituted fused heterocyclic group, aromatic group substituted with at least one $R^b$, heterocyclic group substituted with at least one $R^b$, fused ring group substituted with at least one $R^b$, and fused heterocyclic group substituted with at least one $R^b$;

$R^a$ and $R^b$ are selected from the group consisting of hydrogen atom, halogen, cyano group, C1-C30 linear alkyl, C3-C30 branched alkyl, C1-C30 silyl group, C2-C30 ester group, C1-C30 alkoxy, C1-C30 thioalkyl, C1-C30 haloalkyl, C2-C30 alkene, C2-C30 alkyne, C2-C30 cyano-substituted alkyl, C1-C30 nitro-substituted alkyl, C1-C30 hydroxy-substituted alkyl, and C3-C30 keto-substituted alkyl; wherein g is a positive integer selected from 1 to 8.

4. An organic photoelectric component comprising:
a substrate;
an electrode module disposed on the substrate, which includes a first electrode and a second electrode; and
an active layer disposed between the first electrode and the second electrode, and material for the active layer including at least one organic semiconducting compound according to claim 1;
wherein at least one of the first electrode and the second electrode is transparent or semi-transparent.

5. The organic photoelectric component according to claim 4, wherein the first electrode, the active layer, and the second electrode are disposed on the substrate in turn from bottom to top.

6. The organic photoelectric component according to claim 4, wherein the second electrode, the active layer, and the first electrode are disposed on the substrate in turn from bottom to top.

7. The organic photoelectric component according to claim 4, wherein the material for the active layer further comprises at least one n-type organic semiconducting compound, and an energy gap of the n-type organic semiconducting compound is less than 2 eV.

8. The organic photoelectric component according to claim 7, wherein the at least one n-type organic semiconducting compound is selected form the groups consisting of

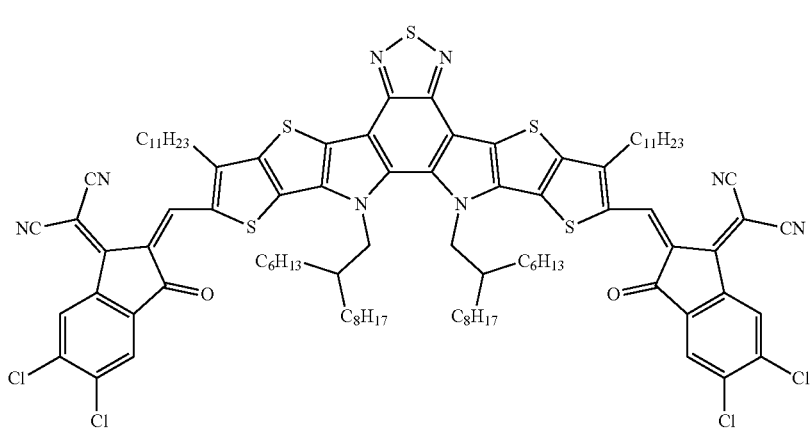

N1

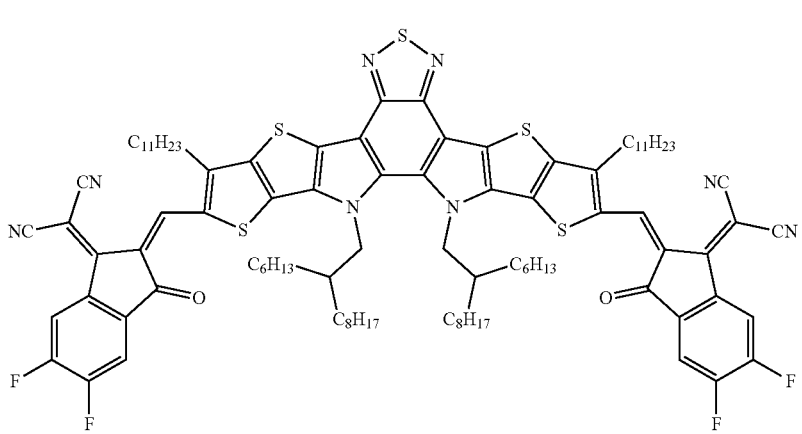

N2

N3
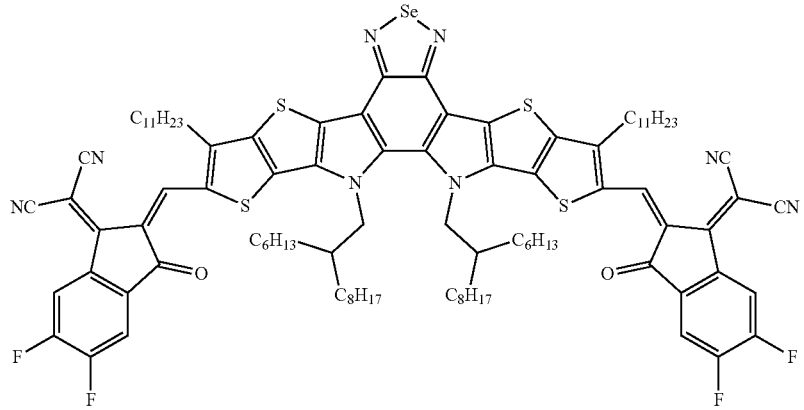
N4
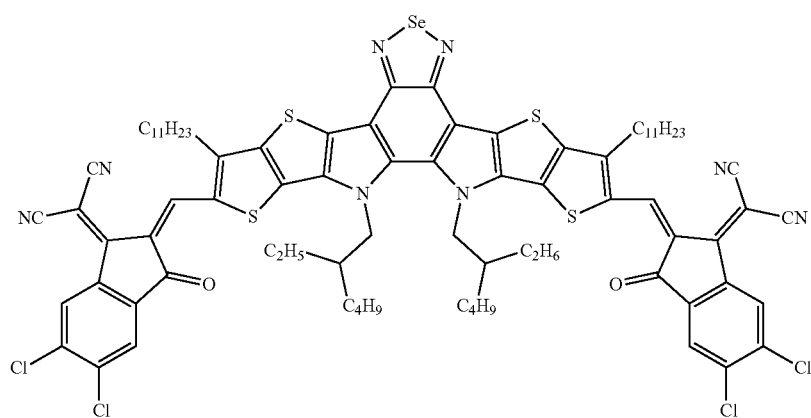
N5
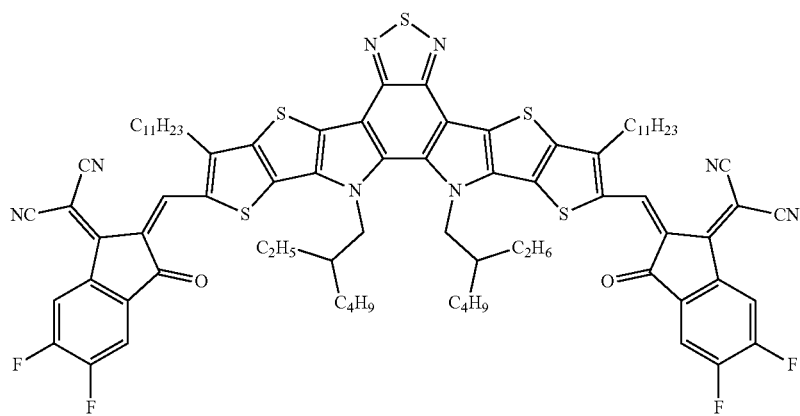
N6
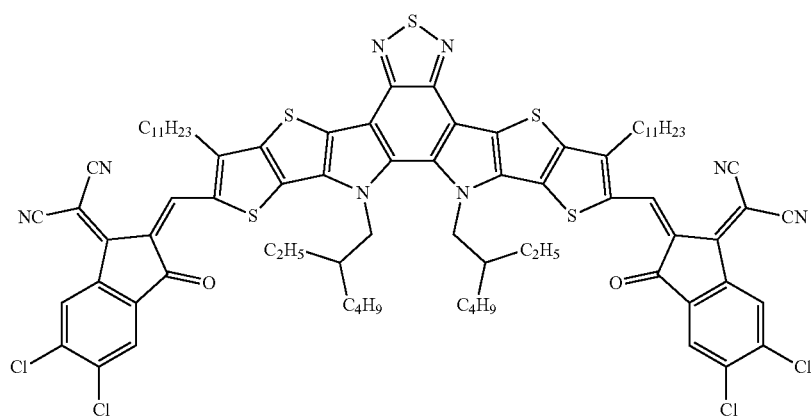

-continued
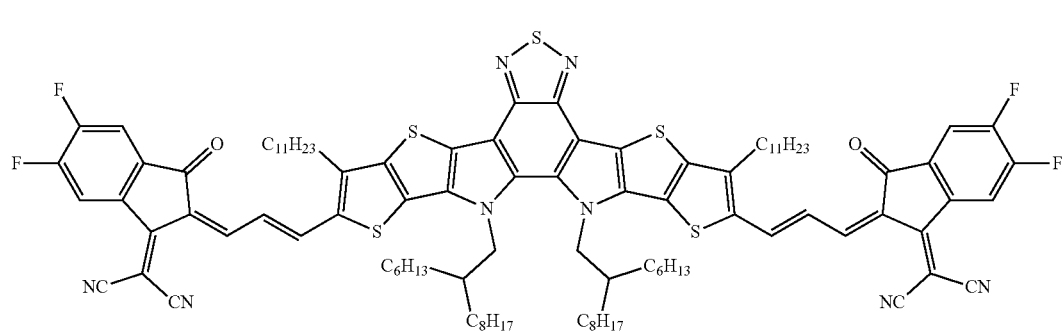
N7
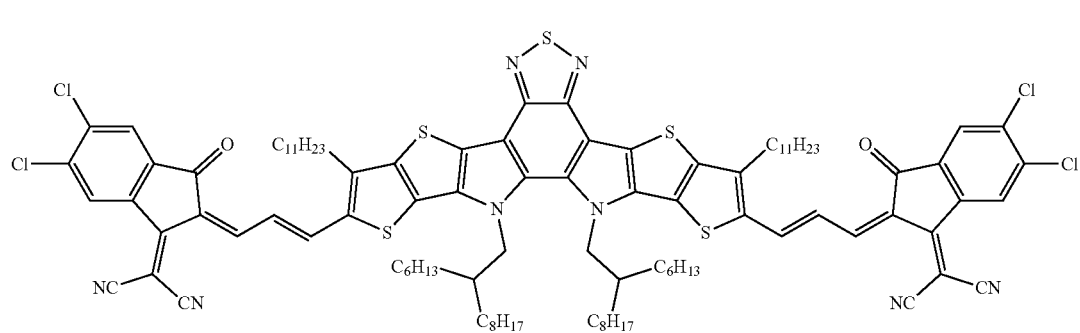
N8
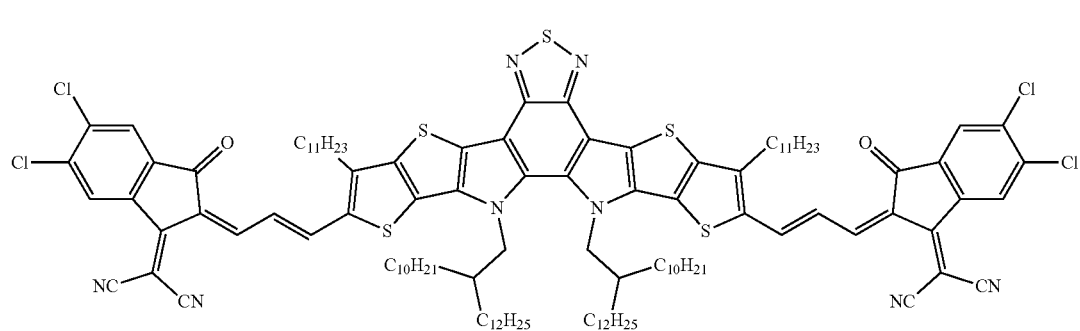
N9
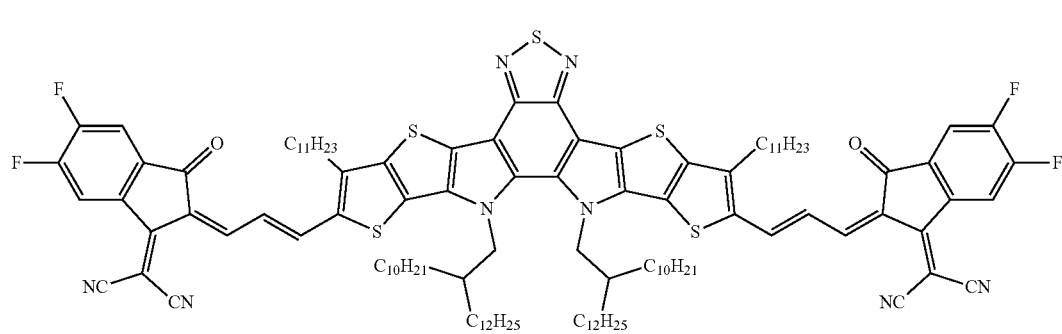
N10

-continued
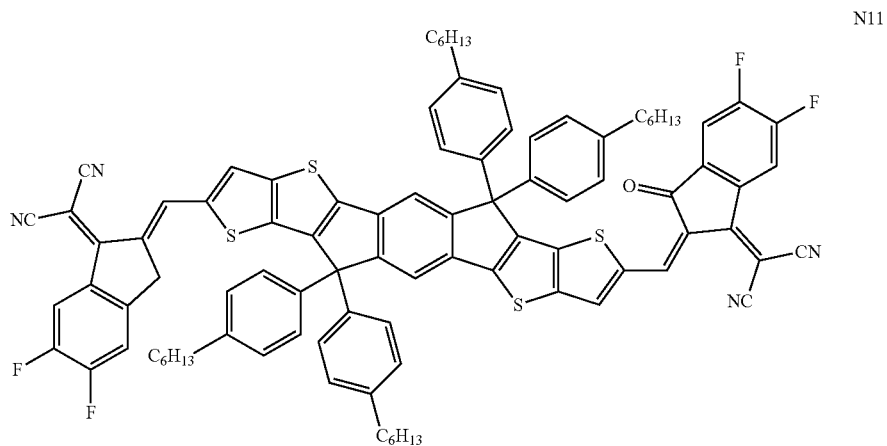
N11
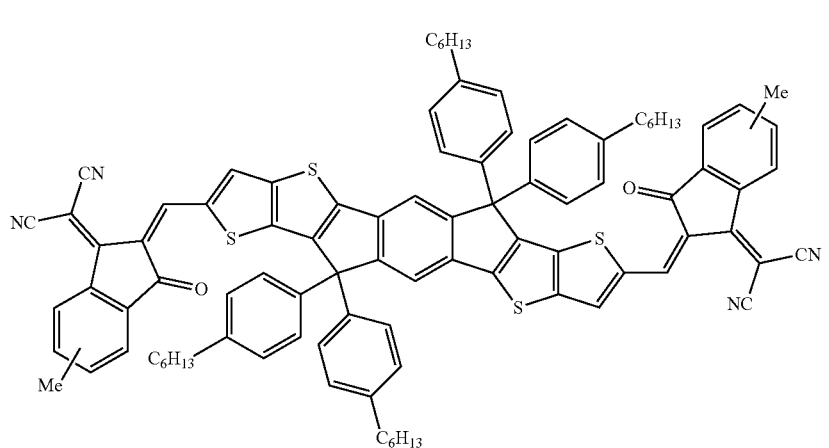
N12
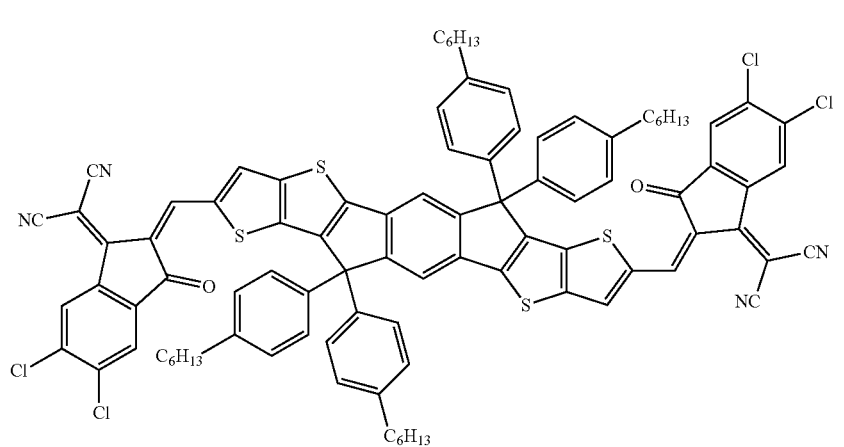
N14

-continued
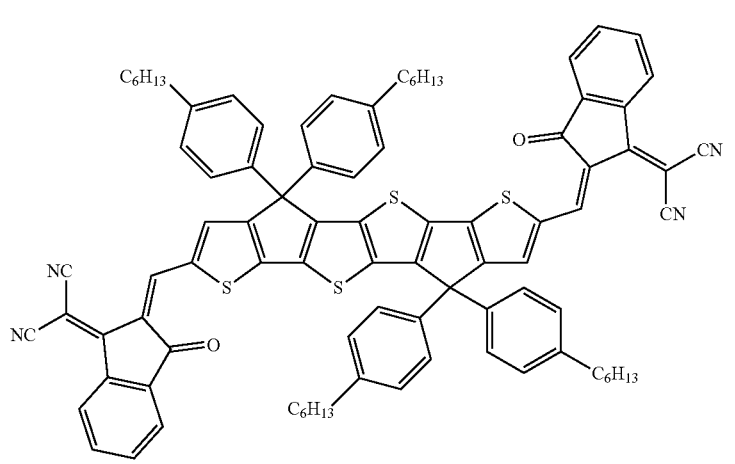
N15
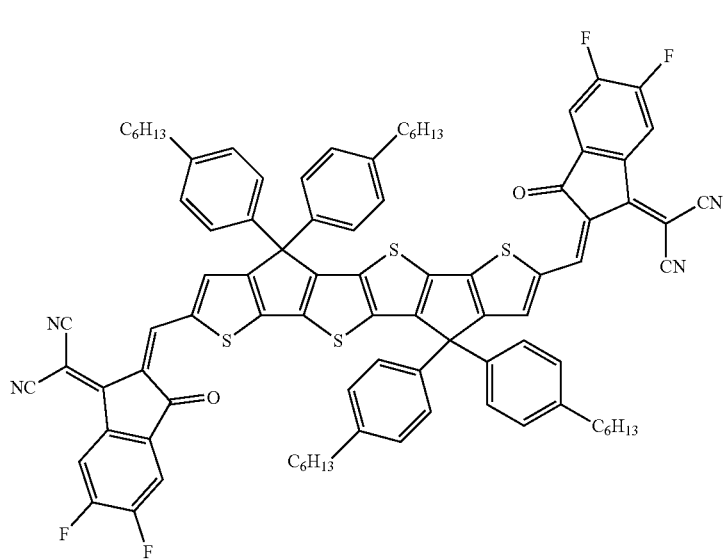
N16
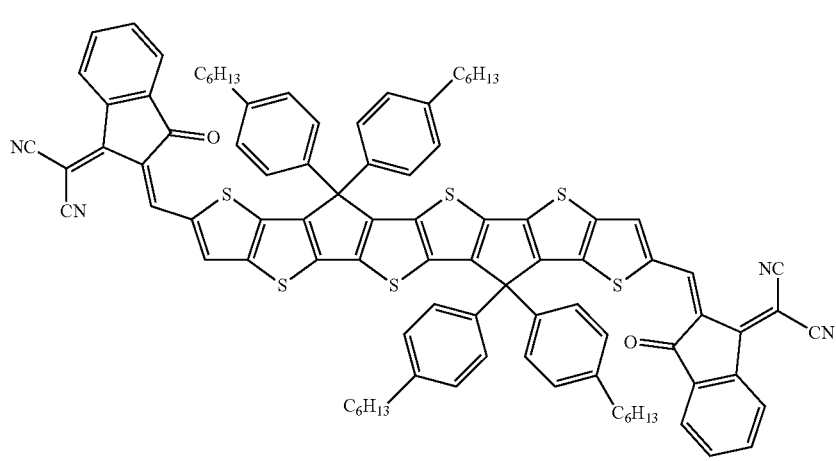
N17

N18
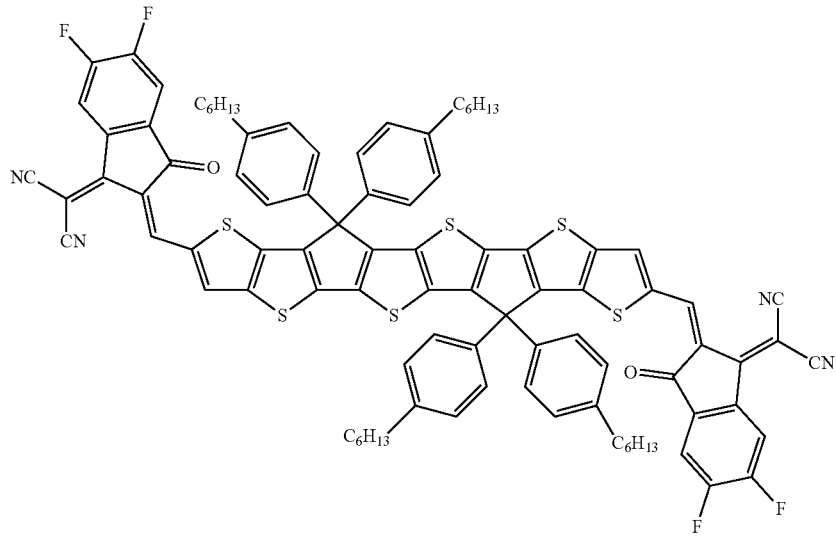
N19
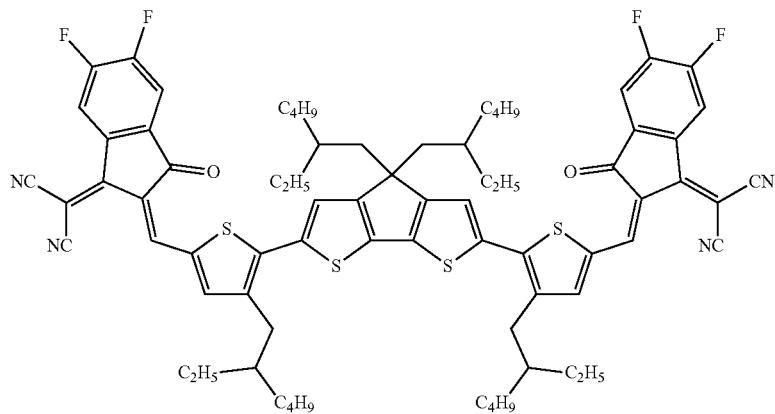
N20
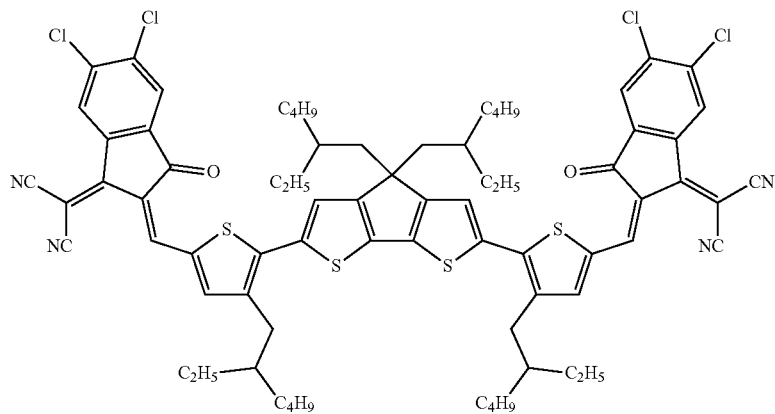

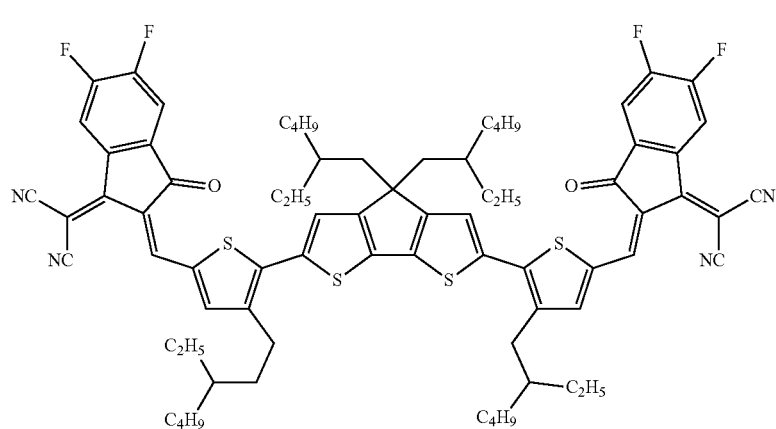
N21
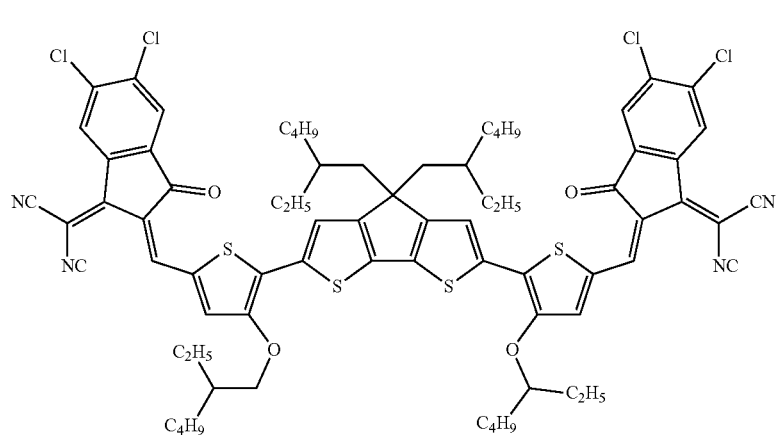
N22
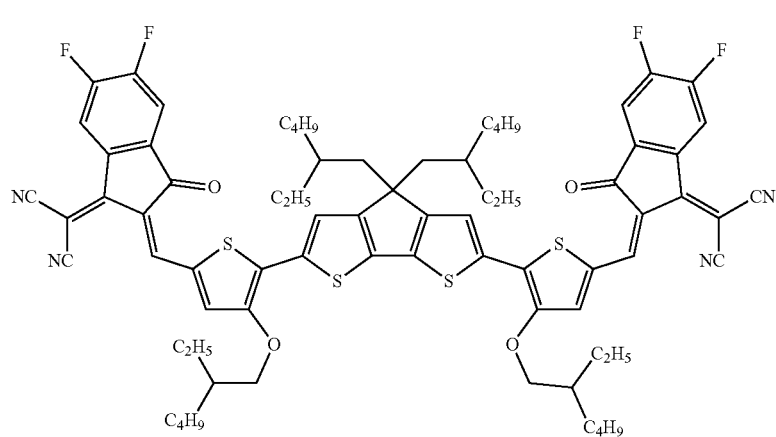
N23

-continued
N24
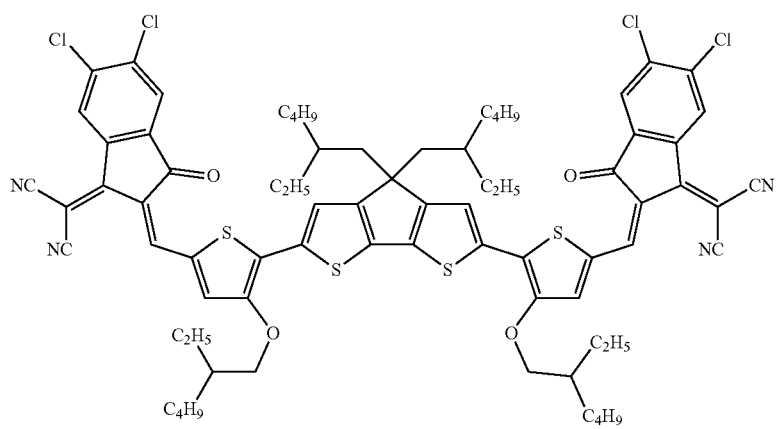
N25
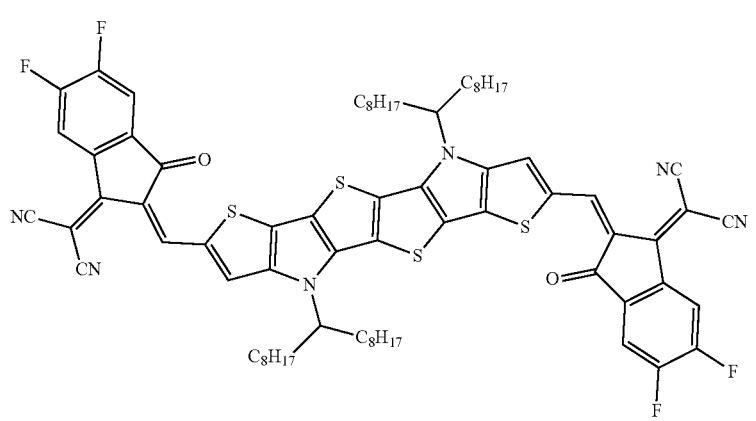
N26
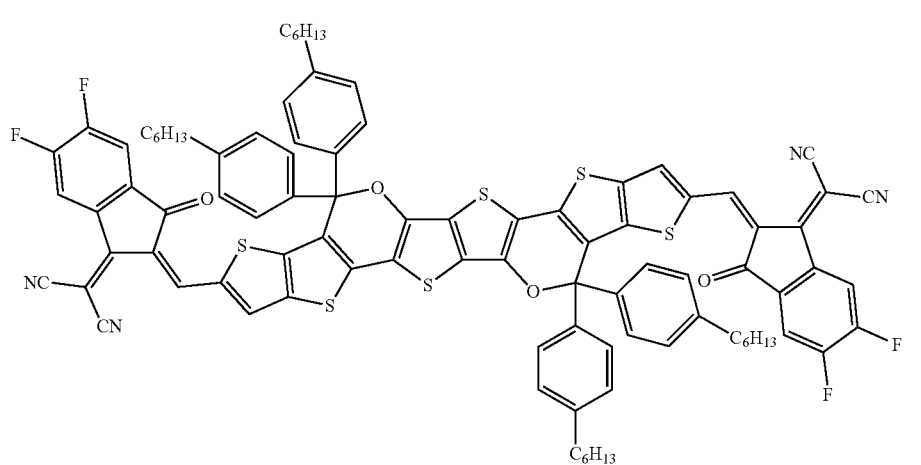
N27
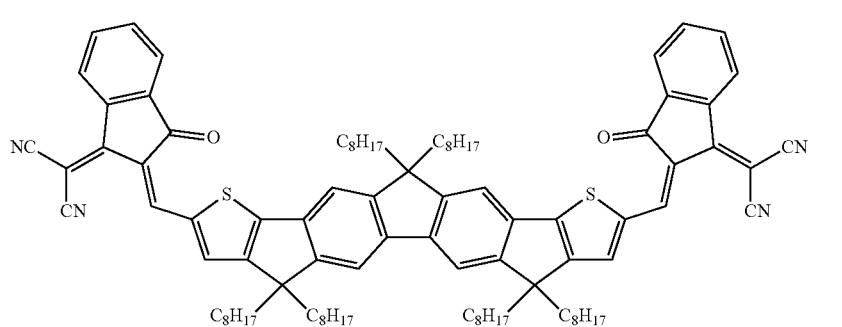

-continued
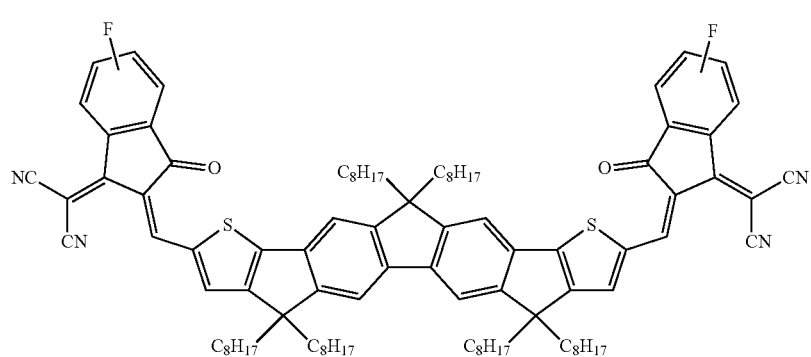
N28
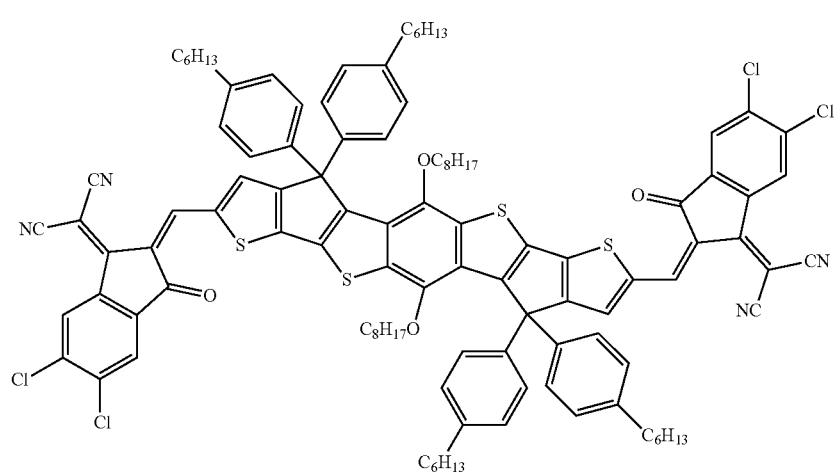
N29
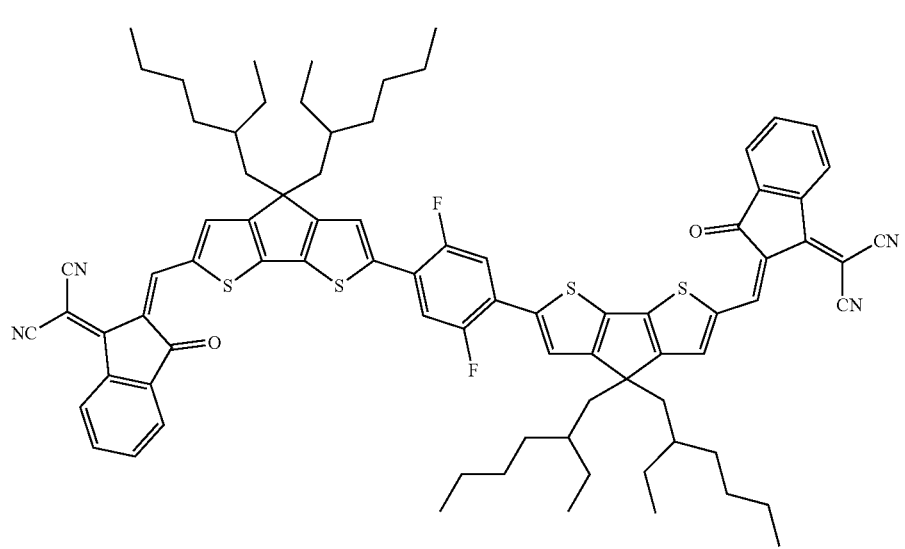
N30

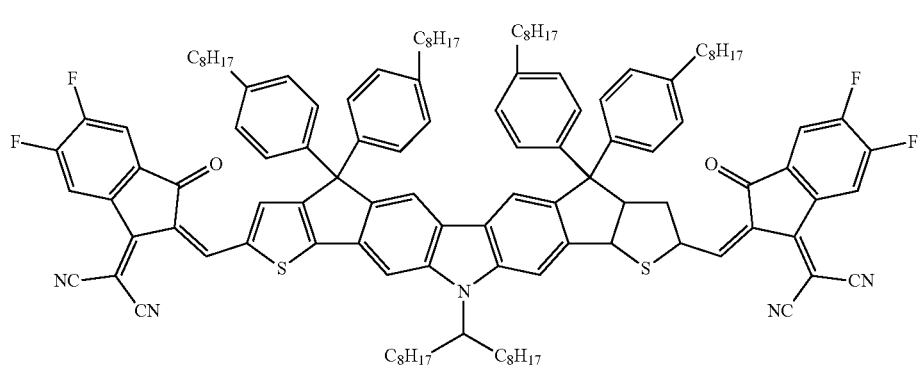
N31
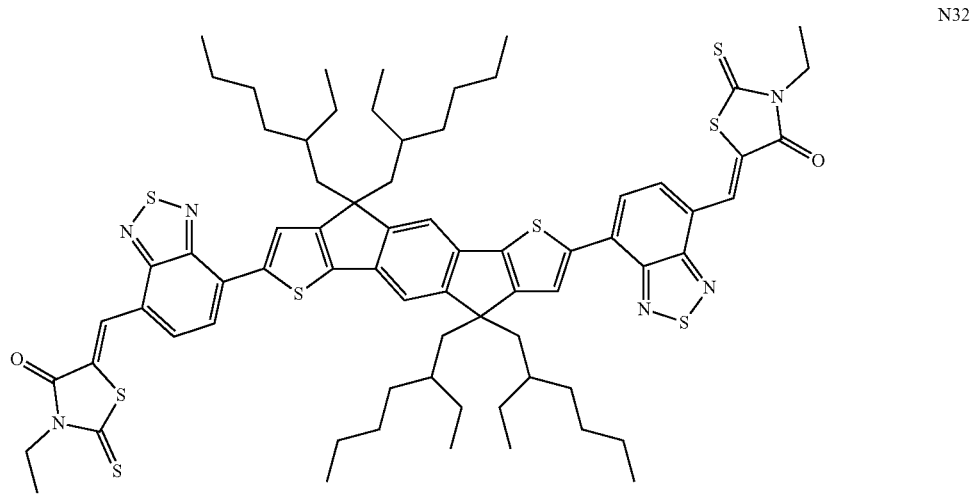
N32
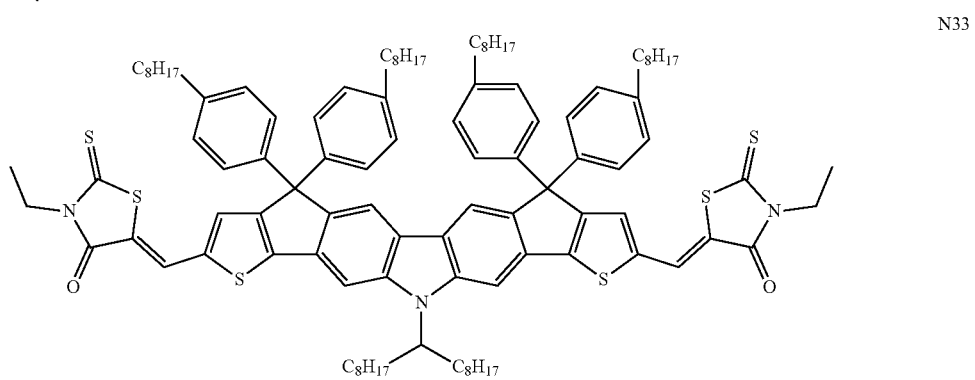
N33
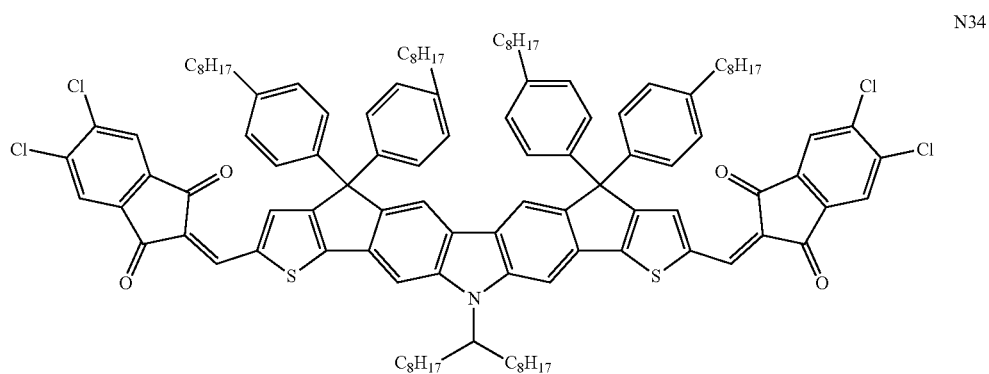
N34

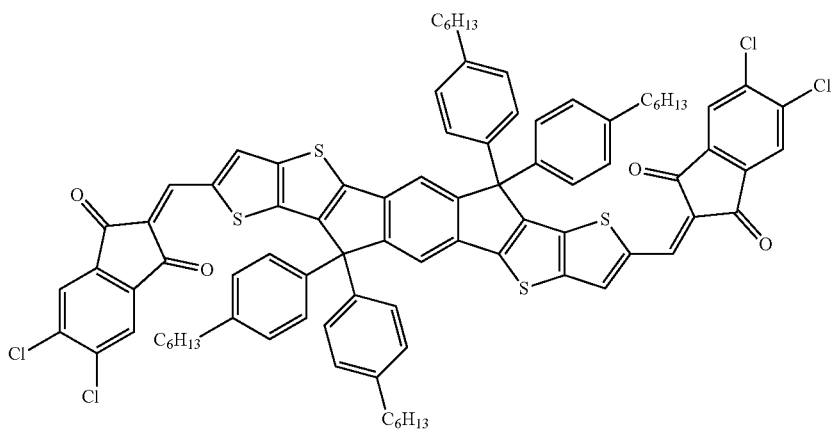

N35

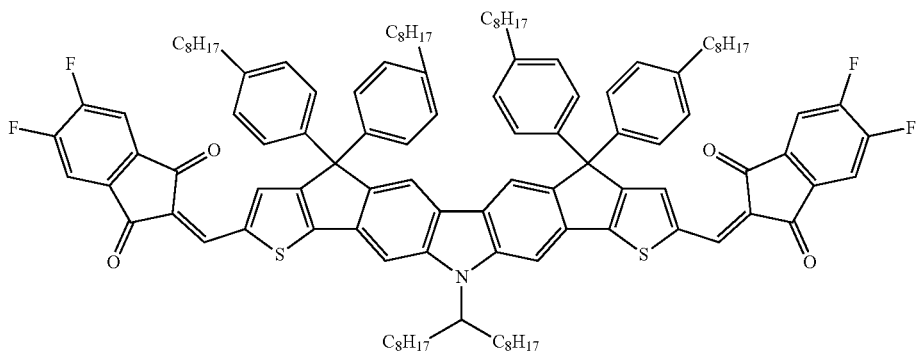

N36

9. The organic photoelectric component according to claim 4, which the organic photoelectric component further comprises
   a first carrier transporting layer disposed between the first electrode and the active layer; and
   a second carrier transporting layer disposed between the second electrode and the active layer.

10. The organic photoelectric component according to claim 4, which the organic photoelectric component further comprises: a first carrier transporting layer disposed between the second electrode and the active layer; and
   a second carrier transporting layer disposed between the first electrode and the active layer.

11. A formulation, comprising
   an organic semiconducting compound according to claim 1;
   an n-type organic semiconducting compound, wherein the energy gap of the n-type semiconducting compound is less than 2 eV; and
   at least one organic solvent,
   wherein the at least one organic solvent is selected from non-halogenated solvent.

12. The formulation according to claim 11, wherein at least one organic solvent is selected from the group consisting of toluene, p-xylene, m-xylene, o-xylene, 1,3,5-trimethylbenzene, 1,2,4-trimethylbenzene, tetrahydrofuran and 2-methyltetrahydrofuran.

* * * * *